United States Patent
Cheng et al.

(10) Patent No.: US 11,299,509 B2
(45) Date of Patent: Apr. 12, 2022

(54) TRIGGER-ACTIVATABLE SUGAR CONJUGATES FOR CANCER-SELECTIVE LABELING AND TARGETING

(71) Applicant: The Board of Trustees of the University of Illinois, Urbana, IL (US)

(72) Inventors: Jianjun Cheng, Champaign, IL (US); Kaimin Cai, Urbana, IL (US); Jin Yu, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 16/485,090

(22) PCT Filed: Feb. 12, 2018

(86) PCT No.: PCT/US2018/017802
§ 371 (c)(1),
(2) Date: Aug. 9, 2019

(87) PCT Pub. No.: WO2018/148650
PCT Pub. Date: Aug. 16, 2018

(65) Prior Publication Data
US 2019/0367550 A1 Dec. 5, 2019

Related U.S. Application Data

(60) Provisional application No. 62/457,597, filed on Feb. 10, 2017.

(51) Int. Cl.
| | | |
|---|---|---|
| *C07H 15/18* | (2006.01) | |
| *A61K 47/55* | (2017.01) | |
| *A61K 47/54* | (2017.01) | |
| *A61K 31/5365* | (2006.01) | |
| *A61K 31/704* | (2006.01) | |
| *A61P 35/00* | (2006.01) | |

(52) U.S. Cl.
CPC ......... *C07H 15/18* (2013.01); *A61K 31/5365* (2013.01); *A61K 31/704* (2013.01); *A61K 47/549* (2017.08); *A61K 47/555* (2017.08); *A61P 35/00* (2018.01)

(58) Field of Classification Search
CPC ...... C07H 15/18; C07H 15/26; A61K 47/555; A61K 47/549; A61K 31/5365; A61K 31/704; A61P 35/00
See application file for complete search history.

(56) References Cited

U.S. PATENT DOCUMENTS

| | | | |
|---|---|---|---|
| 10,550,190 B2* | 2/2020 | Garbaccio | C07K 16/2866 |
| 2014/0031535 A1 | 1/2014 | Jeffrey | |
| 2014/0193437 A1 | 7/2014 | Lin et al. | |
| 2014/0249319 A1 | 9/2014 | Nguyen | |
| 2015/0210728 A1 | 7/2015 | Elewaut et al. | |
| 2015/0258210 A1 | 9/2015 | Van Delft et al. | |
| 2016/0184459 A1 | 6/2016 | Ueki et al. | |
| 2018/0298047 A1* | 10/2018 | Cheng | C07H 15/26 |

FOREIGN PATENT DOCUMENTS

| | | | | |
|---|---|---|---|---|
| WO | WO-0075164 A1 * | 12/2000 | | A61K 48/0041 |
| WO | 2014085275 A1 | 6/2014 | | |
| WO | 2015006555 A3 | 3/2015 | | |
| WO | 2016090157 A1 | 6/2016 | | |
| WO | WO-2016123582 A1 * | 8/2016 | | C07K 9/003 |
| WO | WO-2017/062800 A1 | 4/2017 | | |
| WO | WO-2018/148650 A1 | 8/2018 | | |

OTHER PUBLICATIONS

Etoc, F., "Subcellular control of Rac-GTPase signalling by magnetogenetic manipulation inside living cells." Nature nanotechnology 8.3 (2013): 193.*
Maebashi, M., "Therapeutic evaluation of the effect of biotin on hyperglycemia in patients with non-insulin dependent diabetes mellitus." Journal of Clinical Biochemistry and Nutrition 14.3 (1993): 211-218.*
Stevenson, A., & Lindberg, C. (Eds.), New Oxford American Dictionary 2011 : Oxford University Press. Retrieved Feb. 8, 2021, from https://www.oxfordreference.com/view/10.1093/acref/9780195392883.001.0001/m_en_us1277426.*
Luo, Ji., "Principles of cancer therapy: oncogene and non-oncogene addiction." Cell 136.5 (2009): 823-837.*
Duan, X., "Incorporation of azide sugar analogue decreases tumorigenic potential of breast cancer cells by reducing cancer stem cell population." Science China Chemistry 56.3 (2013): 279-285.*
Prescher, J. A., "Chemical remodelling of cell surfaces in living animals." Nature 430.7002 (2004): 873-877.*
International Search Report and Written Opinion for International Application No. PCT/US18/17802 dated May 18, 2018.
Campbell-Verduyn et al., "Strain-Promoted Copper-Free "Click" Chemistry for 18F Radiolabeling of Bombesin," Angew. Chem. Int. Ed., 50:1117-11120, Sep. 2011.
Canalle et al., "A Comparison of Triazole-forming Bioconjugation Techniques for Constructing Comb-Shaped Peptide-Polymer Bioconjugatesa," Macromol Rapid Commun., 32(2):203-208, Jan. 2011.
Chang et al., "A Strategy for the Selective Imaging of Glycans Using Caged Metabolic Precursors," J Am Chem Soc., 132(28):9516-9518, Jul. 2010.

(Continued)

*Primary Examiner* — John M Mauro
(74) *Attorney, Agent, or Firm* — Haukaas Fortius PLLC; Michael H. Haukaas

(57) ABSTRACT

Disclosed are compounds for the selective labeling of cell-surface sugars in cancer cells. The compounds are activatable by triggers specific to cancer cells, and, when metabolized, label a cancer cell surface sugar with an azide chemical group. Facilitated by a click chemistry reaction, combination of the cell surface-expressed azide with a alkynyl-drug conjugate enables efficient targeted drug delivery to cancer cells with reduced toxicity. Also disclosed are compounds for delivering a drug to an azide-bearing cancer cell, and methods of treating cancer using the compounds.

16 Claims, 19 Drawing Sheets

(56) References Cited

OTHER PUBLICATIONS

Extended Search Report of the European Patent Office dated Dec. 10, 2021 in EP Application No. 18751686.9; 18pgs.
Luchansky et al., "Constructing Azide-Labeled Cell Surfaces Using Polysaccharide Biosynthetic Pathways," Methods Enzymol., 362:249-72, Feb. 2003.
Wang et al., "Selective In Vivo Metabolic Cell-Labeling-Mediated Cancer Targeting," Nat Chem Biol., 13(4):415-424, Apr. 2017.

\* cited by examiner (a)

(b)

(a)

(b)

TRIGGER-ACTIVATABLE SUGAR CONJUGATES FOR CANCER-SELECTIVE LABELING AND TARGETING

RELATED APPLICATIONS

This application is the U.S. National Stage of International Patent Application No. PCT/US2018/017802, filed Feb. 12, 2018, which claims the benefit of priority to U.S. Provisional Patent Application No. 62/457,597, filed Feb. 10, 2017.

GOVERNMENT SUPPORT

This invention was made with government support under DMR Award No. 1309525 awarded by the National Science Foundation and under an R21 Award No. 1 R21 CA198684 A awarded by the National Institutes of Health. The government has certain rights in the invention.

BACKGROUND OF THE INVENTION

Cancer targeted therapy has long been pursued to improve the accumulation of drugs in cancers and minimize their undesired exposure to other parts of the body. The key challenge lies in the identification of unique receptors in cancer tissues and the development of corresponding targeting ligands. Several types of targeting ligands have been developed, and include small molecules, peptides, and aptamers. However, their corresponding receptors are rarely cancer-specific, and the binding affinity between protein receptors and these ligands is relatively low. The most promising targeting ligands developed thus far are monoclonal antibodies (mAb). Advances in this area have made it possible to create mAbs specific to extracellular/cell surface proteins, and several cancer-exclusive proteins have been identified. Despite being the most successful targeting ligands in clinic, mAbs suffer from multiple drawbacks such as high production cost, large size, severe immunogenicity, receptor saturation, and poor solid tumor penetration. In addition, each mAb developed only works well for certain types of cancer because the targeted protein receptors vary from cancer to cancer.

Notably, a common characteristic among all the existing active targeting strategies is that cell surface proteins are regarded as the target. This selection makes sense since proteins provide multiple hydrophobic and charged sites for specific binding with the targeting ligands. However, the number density of cell surface proteins is much lower as compared to sugars and lipids, the other two major components on the cell membrane. Surface-pendant sugars represent a promising target, and are already known to play a vital role in regulating cellular recognition and communication. It was recently discovered that unnatural sugars (e.g., tetraacetyl N-azidoacetylmannosamine ($Ac_4ManAz$)) can be metabolically expressed on the cell surface.[1-11] However, these metabolic labeling processes of unnatural sugars occur in normal cells as well as cancer cells, so there exists a significant challenge in rendering this metabolic labeling process selective or exclusive to cancer cells.

Therefore, there exists a need to develop sugars that can be selectively metabolically expressed on the cell surface of cancer cells. There also exists a need to develop further agents and methods for treating cancer that can take advantage of a selective metabolic labeling process.

SUMMARY OF THE INVENTION

One aspect of the invention provides compositions and methods useful for expressing an azidosugar (e.g., an azido sialic acid; see FIGS. 1 and 2, panel b) on the cell surface of cancer cells. Accordingly, an aspect of the invention is a compound or a pharmaceutically acceptable salt thereof, comprising an optionally substituted N-((azido)acyl) 5-amino-3,5-dideoxy-D-glycero-D-galacto-2-nonulopyranosonic acid moiety or an optionally substituted N-((azido) acyl) 2-amino-2-deoxy-D-galactopyranosyl moiety, a trigger-responsive moiety that is cleaved by a trigger, and a self-immolative linker, wherein the self-immolative linker is covalently bonded to the nonulopyranosonic acid moiety or the galactopyranosyl moiety, and to the trigger-responsive moiety.

In some embodiments, such a compound is represented by formula (I), formula (II), formula (IIa), or a pharmaceutically acceptable salt of any of them:

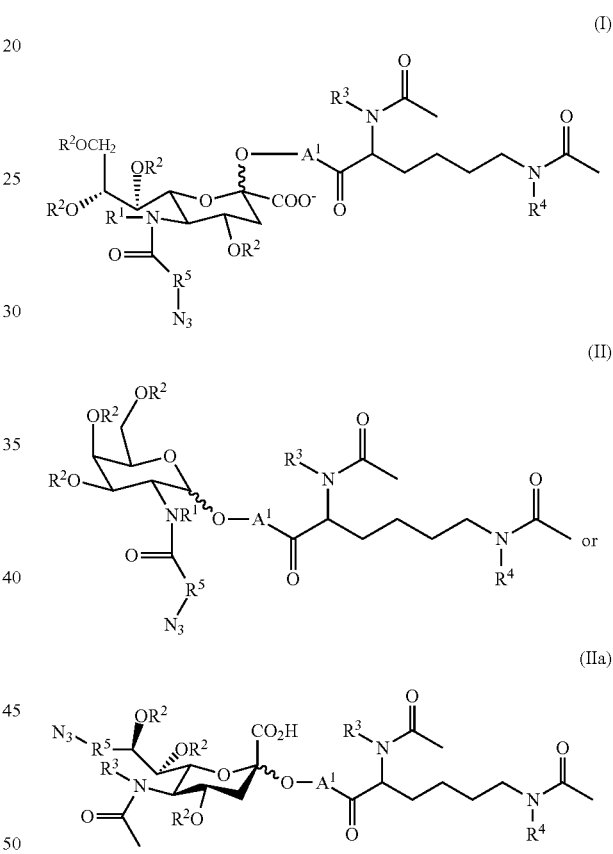

wherein:

$R^1$ represents H or tri(($C_1$-$C_6$)alkyl)silyl;

$R^2$, independently for each occurrence, represents H, —C(O)(($C_1$-$C_6$)alkyl), galactosyl, N-acetylgalactosamino, mannosyl, N-acetylmannosamino, glucosyl, N-acetylglucosamino, maltosyl, or fructosyl;

$R^3$ and $R^4$, independently for each occurrence, represent H, tri(($C_1$-$C_6$)alkyl)silyl, or —C(O)(($C_1$-$C_6$)alkyl);

$R^5$ represents ($C_1$-$C_6$)alkylene; and $A^1$ represents the self-immolative linker.

In some embodiments, such a compound is represented by formula (V) or formula (VI) or a pharmaceutically acceptable salt of either of them:

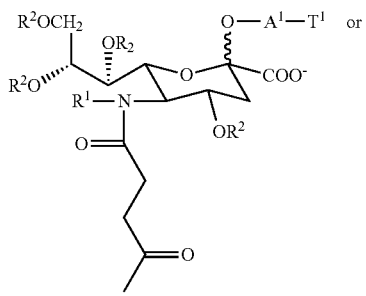
(V)

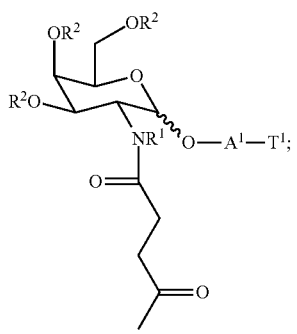
(VI)

wherein:
R¹ represents H or tri((C₁-C₆)alkyl)silyl;
R², independently for each occurrence, represents H, —C(O)((C₁-C₆)alkyl), galactosyl, N-acetylgalactosamino, mannosyl, N-acetylmannosamino, glucosyl, N-acetylglucosamino, maltosyl, or fructosyl;
A¹ represents the self-immolative linker; and
T¹ represents the trigger-responsive moiety.

In other aspects, the invention provides a compound represented by formula (VII) or a pharmaceutically acceptable salt thereof:

K-Pol-Pep-A²-D     (VII);

wherein:
K represents an optionally substituted cycloalkynyl, heterocycloalkynyl, or alkynyl moiety;
Pol represents a polymeric moiety;
Pep represents an amino acid or oligopeptide sequence;
A² represents a self-immolative linker selected from the group consisting of

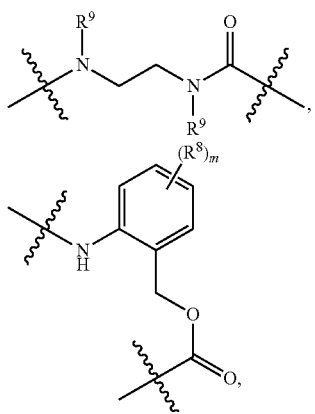

-continued

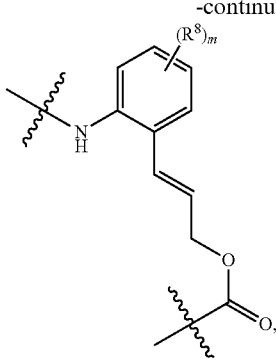

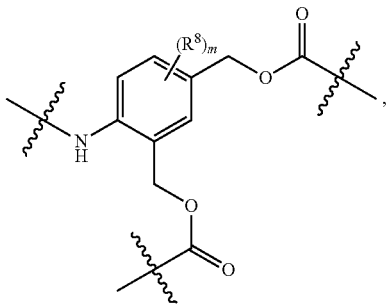

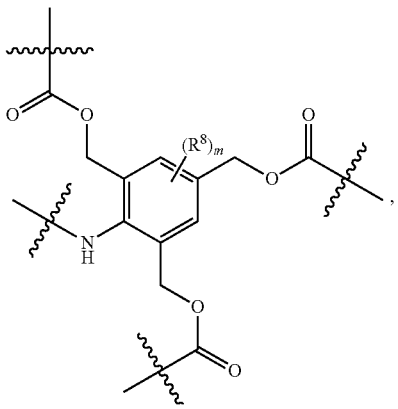

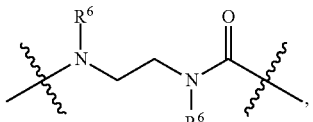

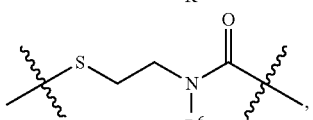

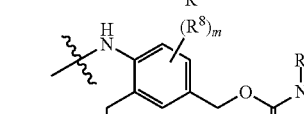

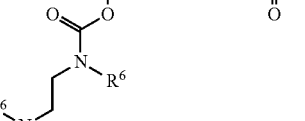, and

-continued

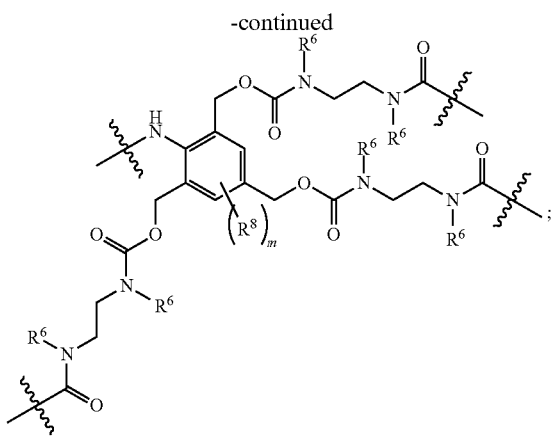

wherein
$R^6$ represents H, tri(($C_1$-$C_6$)alkyl)silyl, or —C(O)(($C_1$-$C_6$)alkyl);
$R^7$ represents H, ($C_1$-$C_6$)alkyl, or heterocycloalkyl;
$R^8$ represents H, halo, —C(O)$_2$H, ($C_1$-$C_6$)alkoxy, di(($C_1$-$C_6$)alkyl)amino, —NO$_2$, —O(CH$_2$CH$_2$O)$_q$CH$_3$;
$R^9$ represents H or ($C_1$-$C_6$)alkyl;
m is 1, 2, 3, 4, or 5;
q is 1 or 2; and
D represents a pharmacophore;
wherein:
the polymeric moiety is a polyalkylene glycol or polyalkylene imide; and
the amino acid or oligopeptide sequence comprises an amide bond that is cleaved by an enzyme (i) overexpressed in a malignant cell relative to a counterpart healthy cell or (ii) expressed in a malignant cell that is not expressed in a counterpart healthy cell.

In other aspects, the invention provides a compound represented by formula (IX) or a pharmaceutically acceptable salt thereof:

wherein:
K represents an optionally substituted cycloalkynyl, heterocycloalkynyl, or alkynyl moiety;
Pol represents a polymeric moiety;
$L^1$ represents a linker comprising a moiety selected from the group consisting of amido, ester, maleimido, imino, sulfide, and disulfide; and
D represents a pharmacophore;
wherein:
the polymeric moiety is a polyalkylene glycol or polyalkylene imide.

In other aspects, the invention provides a compound represented by formula (IX) or a pharmaceutically acceptable salt thereof:

wherein:
K represents an optionally substituted cycloalkynyl, heterocycloalkynyl, or alkynyl moiety;
Pol represents a polymeric moiety;
$L^2$ is absent or represents a trigger-responsive moiety; and
D represents a pharmacophore;
wherein:
the polymeric moiety is a polyalkylene glycol or polyalkylene imide.

In other aspects, the invention provides a pharmaceutical composition, comprising a compound of the invention (e.g., a compound of formula (I), formula (II), formula (IIa), formula (V), formula (VI), formula (VII), formula (IX), and formula (XI)), and a pharmaceutically acceptable excipient or carrier.

In other aspects, the invention relates to methods of expressing an azidosugar (e.g., an azido sialic acid) in a malignant tissue in a mammal, comprising administering to a mammal with malignant tissue an effective amount of a compound comprising an optionally substituted N-((azido)acyl) 5-amino-3,5-dideoxy-D-glycero-D-galacto-2-nonulopyranosonic acid moiety or an optionally substituted N-((azido)acyl) 2-amino-2-deoxy-D-galactopyranosyl, a trigger-responsive moiety that is cleaved by a trigger, and a self-immolative linker (e.g., a compound of formula (I), a compound of formula (II), formula (IIa), a compound of formula (V), and a compound of formula (VI)).

In other aspects, the invention relates to methods of treating cancer, comprising administering to a subject in need thereof an effective amount of a compound comprising an optionally substituted N-((azido)acyl) 5-amino-3,5-dideoxy-D-glycero-D-galacto-2-nonulopyranosonic acid moiety or an optionally substituted N-((azido)acyl) 2-amino-2-deoxy-D-galactopyranosyl, a trigger-responsive moiety that is cleaved by a trigger, and a self-immolative linker (e.g., a compound of formula (I), a compound of formula (II), a compound of formula (IIa), a compound of formula (V), and a compound of formula (VI)).

In other aspects, the invention relates to methods of treating cancer, comprising administering to a subject in need thereof an effective amount of a compound of formula (VII), a compound of formula (IX), or a compound of formula (XI).

DETAILED DESCRIPTION

Cancer targeted therapy has long been pursued to improve the accumulation of drugs in cancers and minimize their undesired exposure to other parts of the body. However, existing cancer-targeting technologies are not satisfactory for therapeutic applications. Though most existing cancer-targeting strategies utilize cancer cell surface proteins as the target, herein cancer cell surface sugars were explored as a therapeutic target, in part because of their higher cell-surface density. Metabolic glycoengineering processes of unnatural sugars provides a facile method to introduce chemical groups onto a cell surface, which enables in-depth studies of otherwise elusive cellular biology questions such as cell internalization, cell fusion, and cell targeting. Disclosed herein are compounds and methods that facilitate controlled labeling of cancer cell-surface sugars, and further therapeutic compositions and methods that take advantage of such cancer-targeting capability.

Figure 1:
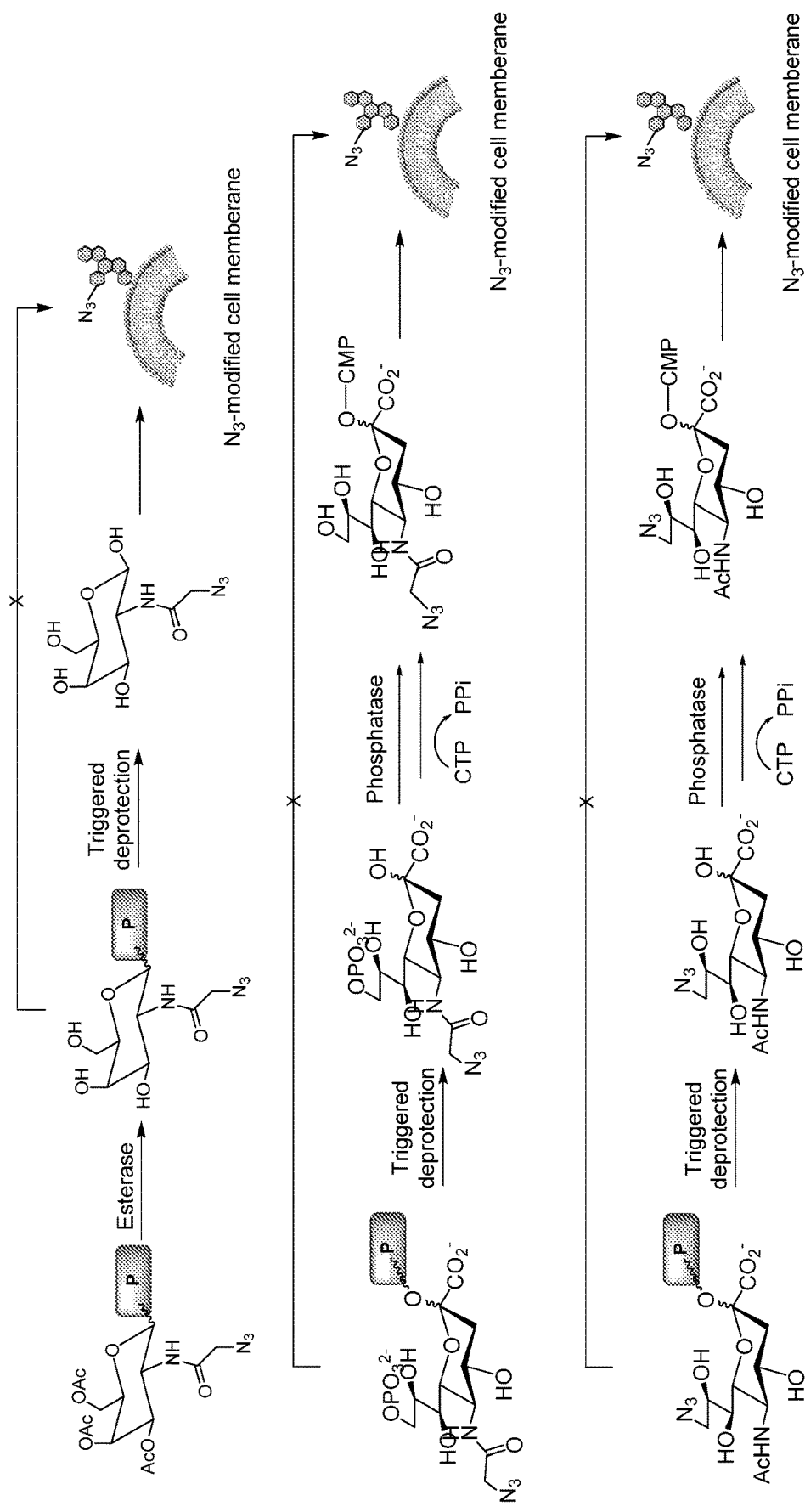
FIG. 1 is a scheme depicting the trigger-activated labeling process of dormant Ac$_3$GalNAz derivatives and dormant neuraminic acid derivatives. P represents a protecting group.

The principles underlying this invention demonstrate that the metabolic labeling capability of azido-sugars can be controlled from the structure perspective. The metabolic labeling process of dormant Ac$_3$GalNAz derivatives and dormant neuraminic acid derivatives are shown in FIG. 1. Ac$_4$GalNAz is hydrolyzed by unspecific esterases upon entering the cells, followed by the phosphorylation and the ring-opening isomerization. Phosphoenolpyruvic acid (PEP) then attacks the newly-formed carbonyl group to form sialic acid which is then (1) deprived of the phosphate group, (2) conjugated to protein, and finally (3) expressed on the cell surface in the form of glycoprotein. It can be anticipated that the ring-opening isomerization step is essential for the successful metabolic labeling and that the exposure of the hydroxyl group at C1 site (1-OH) is necessary for the successful ring-opening isomerization. The inventors surprisingly discovered that modifying the C1 site of Ac$_4$GalNAz by forming a glycosidic bond that would survive the cellular esterases prevents the ring-opening isomerization step, thus blocking the whole metabolic labeling process. This strategy can also be applied to the neuraminic acid derivatives disclosed herein. By designing a trigger-responsive glycosidic (ether) bond that can expose the 1-OH in the presence of certain triggers, the metabolic labeling process can be controlled. Cancer selective chemical labeling can potentially be achieved by using neuraminic acid derivatives and galactosamine derivatives that are responsive to specific cancer-associated triggers. Exemplary cancer-associated triggers can include redox dysregulation, elevated oxidant level, and overexpressed enzymes.

Compounds of the Invention

Sugar Derivative Compounds

An aspect of the invention relates to a compound or a pharmaceutically acceptable salt thereof, comprising:

an optionally substituted N-((azido)acyl) 5-amino-3,5-dideoxy-D-glycero-D-galacto-2-nonulopyranosonic acid moiety or an optionally substituted N-((azido)acyl) 2-amino-2-deoxy-D-galactopyranosyl;

a trigger-responsive moiety that is cleaved by a trigger; and a self-immolative linker;

wherein the self-immolative linker is covalently bonded to the nonulopyranosonic acid moiety or the galactopyranosyl moiety, and to the trigger-responsive moiety.

In certain embodiments, the trigger is heightened, overexpressed, or otherwise enhanced in a cancerous tissue relative to a healthy tissue.

In certain embodiments, the trigger is cellular peroxide.

In certain such embodiments, the trigger-responsive moiety comprises a boronic acid group, a dialkyl boronate group, a diaryl boronate group, a di(aralkyl)boronate group, a borolane group, or a dioxaborolane group. Exemplary embodiments are shown below:

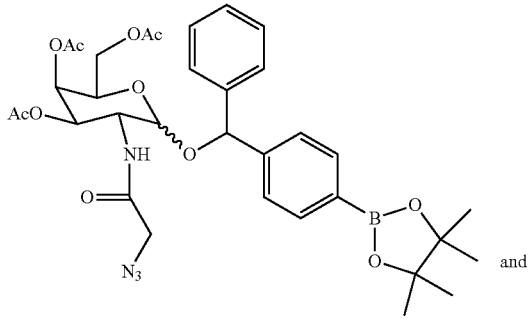

and

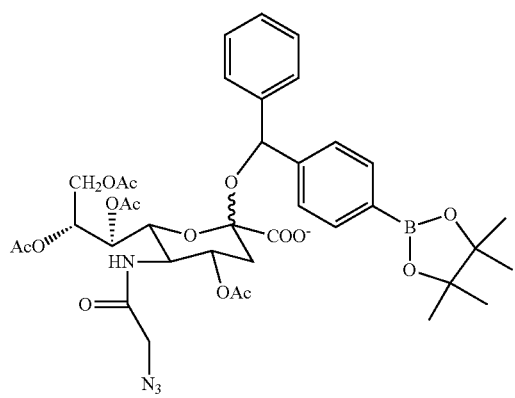

In certain such embodiments, upon cleavage of the trigger-responsive moiety by cellular peroxide the self-immolative linker disassembles, thereby releasing an optionally substituted N-((azido)acyl) 5-amino-3,5-dideoxy-D-glycero-D-galacto-2-nonulopyranosonic acid or an optionally substituted N-((azido)acyl) 2-amino-2-deoxy-D-galactopyranoside.

In alternative embodiments, the trigger is hypoxia.

In certain such embodiments, the trigger-responsive moiety comprises a 2-nitroimidazole moiety or an azo group, such as azobenzene. Exemplary embodiments are shown below:

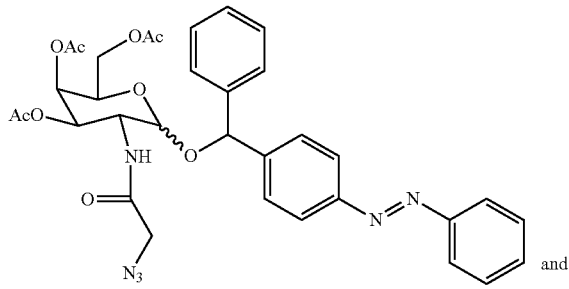

and

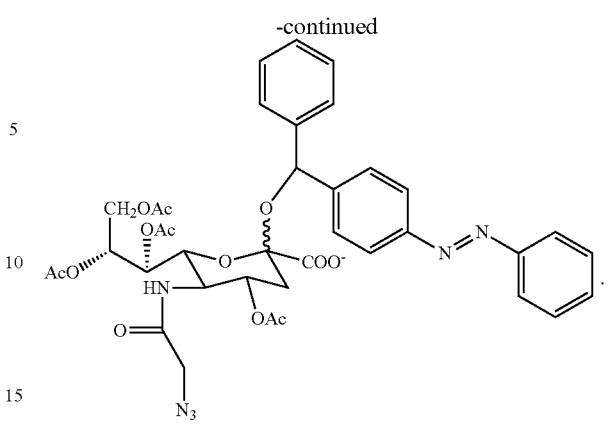

In certain such embodiments, upon cleavage of the trigger-responsive moiety under hypoxic conditions the self-immolative linker disassembles, thereby releasing an optionally substituted N-((azido)acyl) 5-amino-3,5-dideoxy-D-glycero-D-galacto-2-nonulopyranosonic acid or an optionally substituted N-((azido)acyl) 2-amino-2-deoxy-D-galactopyranoside.

In alternative embodiments, the trigger is a sulfhydryl- or thiolate-containing compound, such as glutathione.

In certain such embodiments, the trigger-responsive moiety comprises a disulfide bond. Exemplary embodiments are shown below:

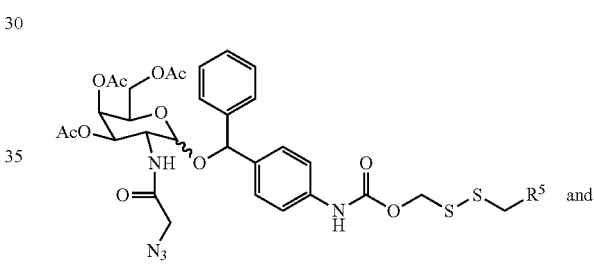

wherein $R^5$ represents $(C_1-C_6)$alkyl.

In certain such embodiments, upon cleavage of the disulfide bond by a sulfhydryl- or thiolate-containing compound the self-immolative linker disassembles, thereby releasing an optionally substituted N-((azido)acyl) 5-amino-3,5-dideoxy-D-glycero-D-galacto-2-nonulopyranosonic acid or an optionally substituted N-((azido)acyl) 2-amino-2-deoxy-D-galactopyranoside.

In alternative embodiments, the trigger is NAD(P)H dehydrogenase (quinone 1) (NQO1).

In certain such embodiments, the trigger-responsive moiety comprises an optionally substituted quinone, covalently bound to an optionally substituted propionic acid or propionic amide moiety. Exemplary embodiments are shown below:

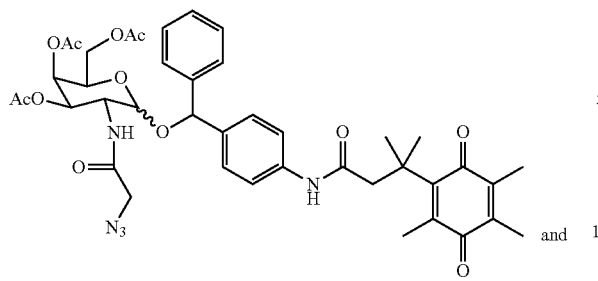

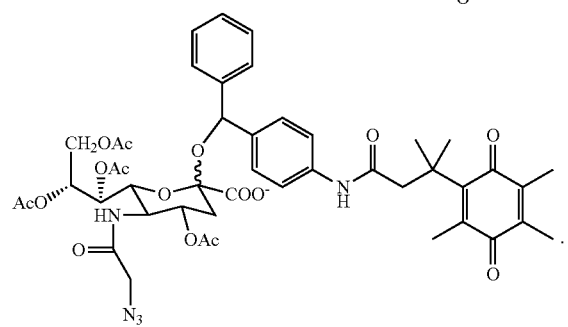

In certain such embodiments, upon cleavage of the optionally substituted quinone, covalently bound to an optionally substituted propionic acid or propionic amide moiety by NAD(P)H dehydrogenase (quinone 1) (NQO1) the self-immolative linker disassembles, thereby releasing an optionally substituted N-((azido)acyl) 5-amino-3,5-dideoxy-D-glycero-D-galacto-2-nonulopyranosonic acid or an optionally substituted N-((azido)acyl) 2-amino-2-deoxy-D-galactopyranoside.

In certain embodiments, the trigger is a cathepsin enzyme.

In certain embodiments, the trigger is a matrix metalloproteinase enzyme.

In certain embodiments, the trigger is an amino acid or oligopeptide sequence comprising an amide bond that is a cleaved by a matrix metalloproteinase enzyme. In certain such embodiments, the trigger-responsive moiety is an amino acid or oligopeptide sequence comprising an amide bond that is a cleaved by a cathepsin enzyme.

In further embodiments, the trigger-responsive group comprises an acid-sensitive moiety, such as an imine, acetal, ketal, or carbamate. Exemplary trigger-responsive groups are depicted in the embodiments shown below:

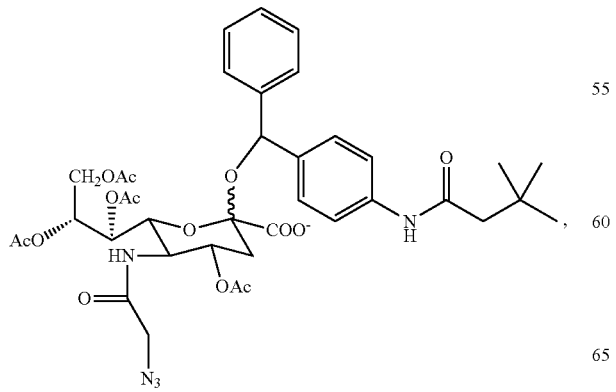

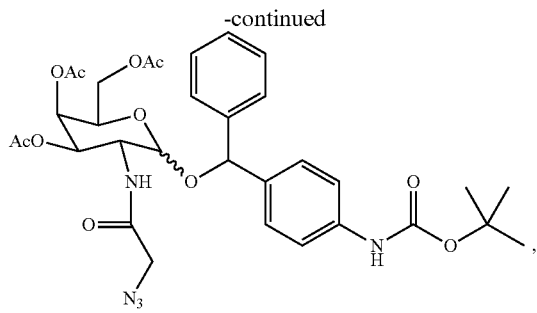

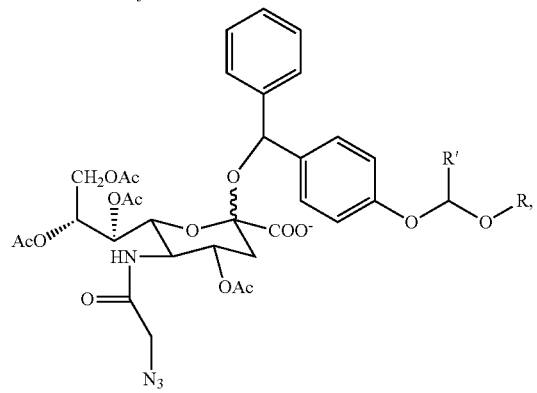

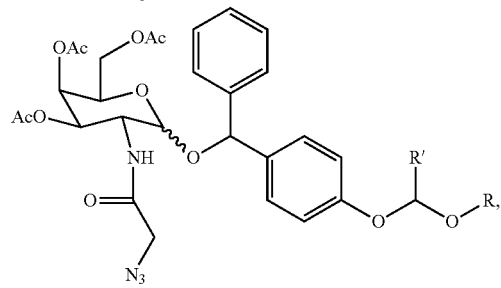

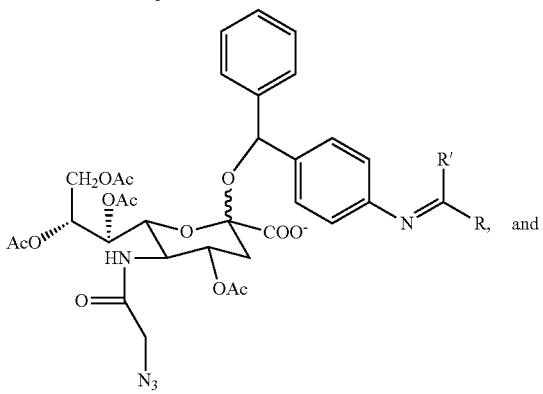

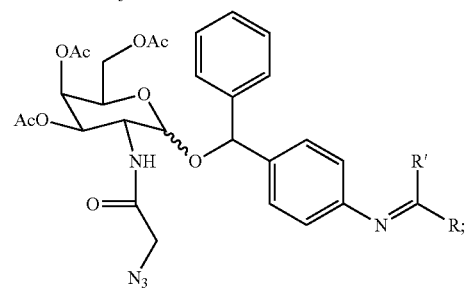

wherein:
R represents H or $(C_1-C_6)$alkyl; and
R' represents H, $(C_1-C_6)$alkyl, or aryl.

In certain such embodiments, the amino acid or oligopeptide sequence comprising an amide bond comprises Phe-Lys, Val-Lys, Ala-Lys, Val-Cit, Phe-Cit, Leu-Cit, Ile-Cit, Trp-Cit, Phe-Arg(NO₂), Phe-Arg(Ts), or Lys-Gly-Arg-Arg. Cit represents citrulline, and Ts represents a tosylate protecting group.

In certain embodiments, the amino acid or oligopeptide sequence is a substituted lysine amide.

In certain such embodiments, upon cleavage of the amide bond by the cathepsin enzyme the self-immolative linker disassembles, thereby releasing an optionally substituted N-((azido)acyl) 5-amino-3,5-dideoxy-D-glycero-D-galacto-2-nonulopyranosonic acid or an optionally substituted N-((azido)acyl) 2-amino-2-deoxy-D-galactopyranoside.

In certain embodiments, the cathepsin enzyme is cathepsin L.

In certain embodiments, the compound is represented by formula (I), formula (II) or formula (IIa), or a pharmaceutically acceptable salt of any of them:

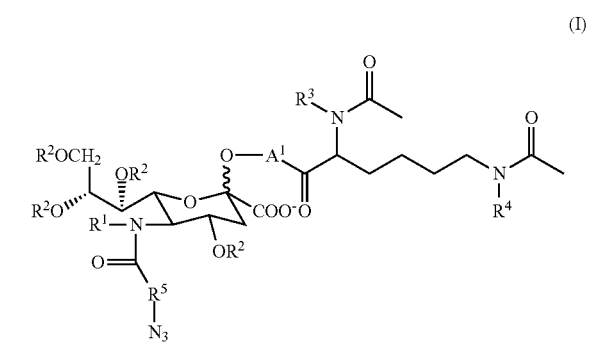

(I)

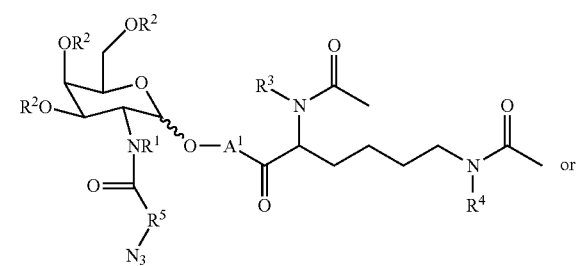

(II)

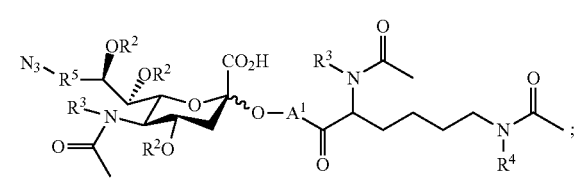

(IIa)

wherein:
R¹ represents H or tri((C₁-C₆)alkyl)silyl;
R², independently for each occurrence, represents H, —C(O)((C₁-C₆)alkyl), galactosyl, N-acetylgalactosamino, mannosyl, N-acetylmannosamino, glucosyl, N-acetylglucosamino, maltosyl, or fructosyl;
R³ and R⁴, independently for each occurrence, represent H, tri((C₁-C₆)alkyl)silyl, or —C(O)((C₁-C₆)alkyl);
R⁵ represents (C₁-C₆)alkylene; and
A¹ represents the self-immolative linker.

The variables in formula (I), (II), and (IIa) may be further selected as described below.

In certain embodiments of the compounds disclosed herein, R¹ represents H.

In certain embodiments of the compounds disclosed herein, R², independently for each occurrence, represents H or —C(O)CH₃.

In certain embodiments of the compounds disclosed herein, all occurrences of R² are identical.

In certain embodiments, R³ and R⁴ are H.

In certain embodiments, the compound is represented by formula (I) or a pharmaceutically acceptable salt thereof:

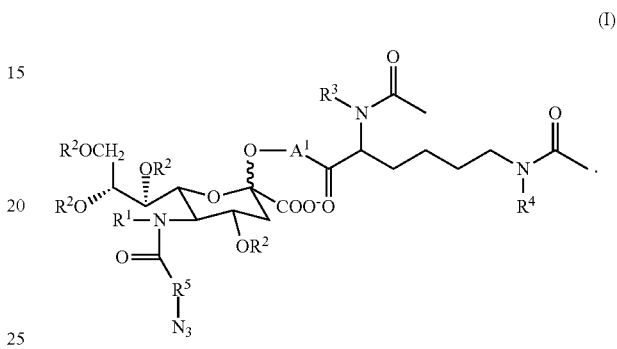

(I)

In certain embodiments, the compound is represented by formula (II) or a pharmaceutically acceptable salt thereof:

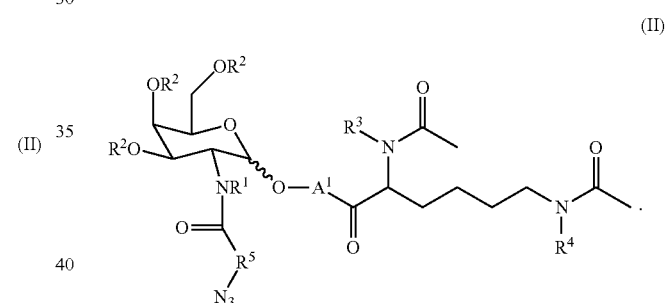

(II)

In certain embodiments, the compound is represented by formula (IIa) or a pharmaceutically acceptable salt thereof:

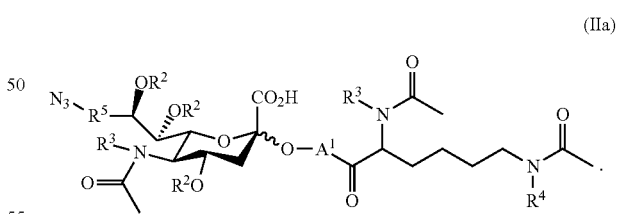

(IIa)

The compounds disclosed herein include a self-immolative linker that spaces and covalently links together the nonulopyranosonic acid moiety or the galactopyranosyl moiety and the trigger-responsive moiety.

In some embodiments, the self-immolative linker is a bifunctional chemical moiety, capable of covalently linking together two spaced chemical moieties (i.e., the nonulopyranosonic acid moiety or the galactopyranosyl moiety and the trigger-responsive moiety) into a normally stable tripartite molecule. In some embodiments, the self-immolative linker enables the release of one of the spaced chemical moieties from the tripartite molecule by means of trigger-induced cleavage (e.g., enzymatic cleavage); and such cleavage, can spontaneously cleave from the remainder of the molecule to release the other of the spaced chemical moieties (e.g., the nonulopyranosonic acid moiety or the galactopyranosyl moiety).

In certain embodiments of the compounds disclosed herein:

$A^1$ represents a group —$X^1$—$Y^1$—;

$X^1$ represents a bond or —C(O)—; and $Y^1$ represents a bond or optionally substituted —(($C_1$)alkylene)-arylene- or —(($C_1$)alkylene)-heteroarylene-.

In certain such embodiments of the compounds disclosed herein, $Y^1$ represents optionally substituted —(($C_1$)alkylene)-arylene-.

In certain such embodiments of the compounds disclosed herein, the self-immolative linker is selected from the group consisting of:

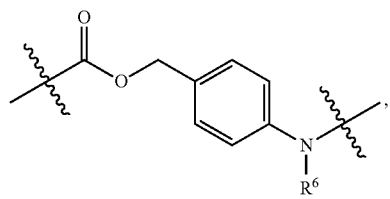

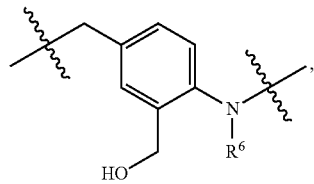

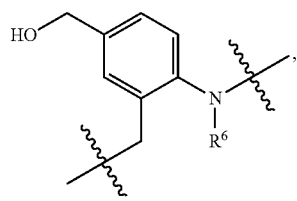

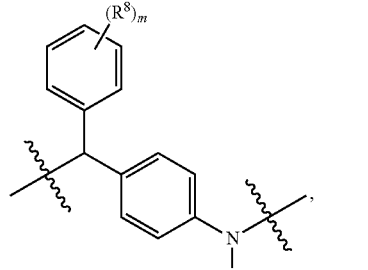

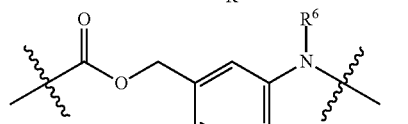

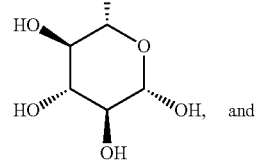

-continued

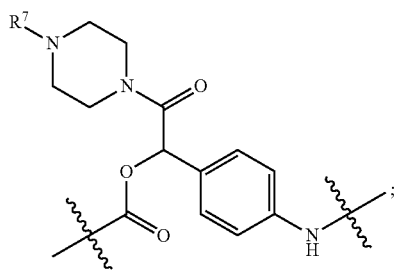

wherein $R^6$ represents H, tri(($C_1$-$C_6$)alkyl)silyl, or —C(O)(($C_1$-$C_6$)alkyl);

$R^7$ represents H, ($C_1$-$C_6$)alkyl, or heterocycloalkyl;

$R^8$ represents H, halo, —C(O)$_2$H, ($C_1$-$C_6$)alkoxy, di(($C_1$-$C_6$)alkyl)amino, —NO$_2$, —O(CH$_2$CH$_2$O)$_q$CH$_3$;

m is 1, 2, 3, 4, or 5; and q is 1 or 2.

In certain such embodiments, $R^8$ is H.

In certain embodiments, the self-immolative linker is

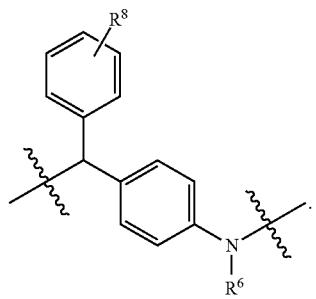

In certain such embodiments, the self-immolative linker is

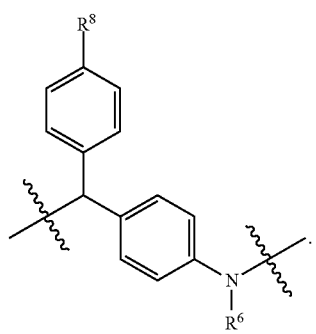

In further such embodiments, $R^8$ is H.

In certain embodiments, the compound for expressing an azidosugar (e.g., an azido sialic acid) on the cell surface of cancer cells is represented by formula (III) or a pharmaceutically acceptable salt thereof:

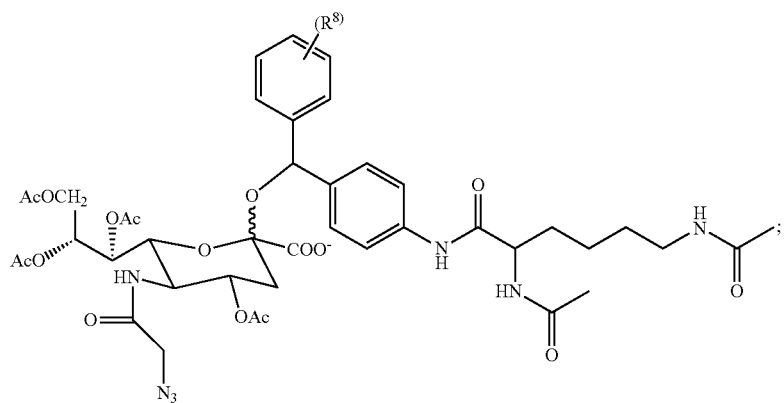

(III)

wherein $R^8$ represents H, halo, —C(O)$_2$H, (C$_1$-C$_6$)alkoxy, di((C$_1$-C$_6$)alkyl)amino, —NO$_2$, —O(CH$_2$CH$_2$O)$_q$CH$_3$;
m is 1, 2, 3, 4, or 5; and
q is an integer from 1 to 5000.

In further embodiments, the compound is represented by formula (III') or a pharmaceutically acceptable salt thereof:

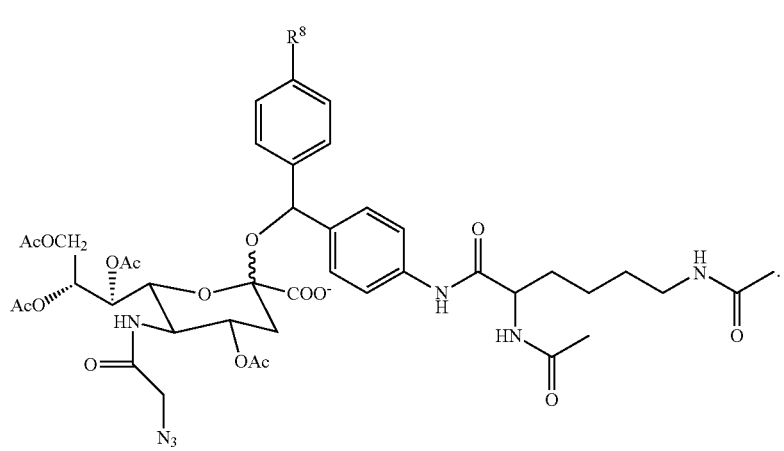

(III')

In some embodiments, the compound for expressing an azidosugar (e.g., an azido sialic acid) on the cell surface of cancer cells is represented by formula (IV) or a pharmaceutically acceptable salt thereof:

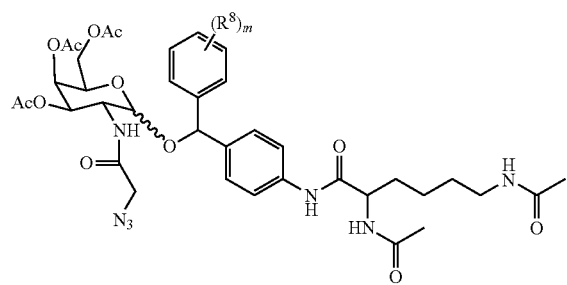

(IV)

-continued

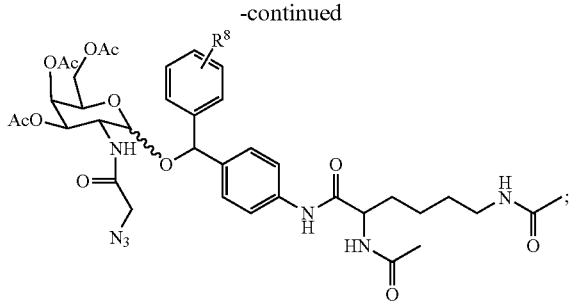

wherein $R^8$ represents H, halo, —C(O)$_2$H, (C$_1$-C$_6$)alkoxy, di((C$_1$-C$_6$)alkyl)amino, —NO$_2$, —O(CH$_2$CH$_2$O)$_q$CH$_3$;
m is 1, 2, 3, 4, or 5; and
q is 1 or 2.

In some embodiments, the compound is represented by formula (IV') or a pharmaceutically acceptable salt thereof:

(IV')

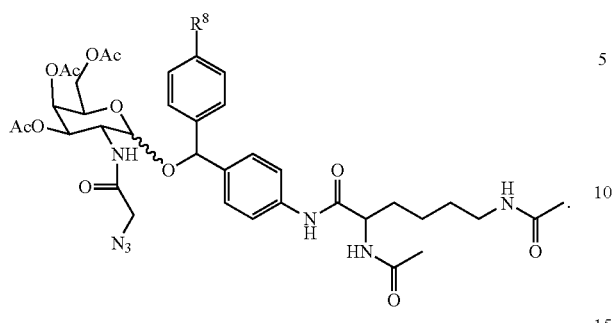

In further such embodiments, $R^8$ is H.

In some embodiments of the compounds disclosed herein, the compound further comprises a sugar linker comprising one or more sugar moieties, wherein (i) said sugar linker covalently links the self-immolative linker to the anomeric carbon of the N-((azido)acyl) 5-amino-3,5-dideoxy-D-glycero-D-galacto-2-nonulopyranosonic acid moiety or the anomeric carbon of the N-((azido)acyl) 2-amino-2-deoxy-D-galactopyranosyl moiety, or (ii) $A^1$ further comprises said sugar linker. In some embodiments, the self-immolative linker enables the release of one of the spaced chemical moieties from the molecule by means of trigger-induced cleavage (e.g., enzymatic cleavage); and such cleavage, can spontaneously cleave from the remainder of the molecule to release another of the spaced chemical moieties (e.g., the nonulopyranosonic acid moiety or the galactopyranosyl moiety). In some embodiments, the released chemical moiety comprises the sugar linker covalently bonded to the nonulopyranosonic acid moiety and to one or more sugar moieties. In some embodiments, the released chemical moiety comprises the sugar linker covalently bonded to the galactopyranosyl moiety and to one or more sugar moieties.

In some embodiments of the compounds disclosed herein, the one or more sugar moieties are selected from the group consisting of galactosyl, N-acetylgalactosamino, mannosyl, N-acetylmannosamino, neuraminic acid, glucosyl, N-acetylglucosamino, maltosyl, and fructosyl.

In some such embodiments of the compounds disclosed herein, the self-immolative linker is selected from the group consisting of:

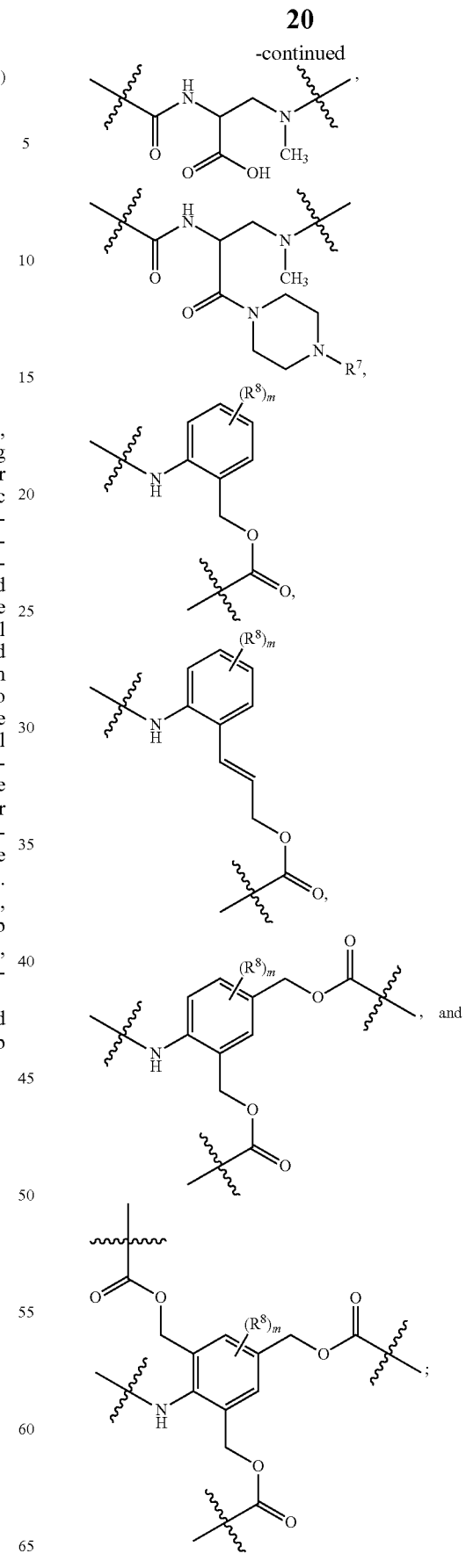

wherein

R⁶ represents H, tri((C₁-C₆)alkyl)silyl, or —C(O)((C₁-C₆)alkyl);

R⁷ represents H, (C₁-C₆)alkyl, or heterocycloalkyl;

R⁸ represents H, halo, —C(O)₂H, (C₁-C₆)alkoxy, di((C₁-C₆)alkyl)amino, —NO₂, —O(CH₂CH₂O)$_q$CH₃;

R⁹ represents H or (C₁-C₆)alkyl;

m is 1, 2, 3, 4, or 5;

n is 1 or 2; and q is 1 or 2.

In some embodiments, the compound is represented by formula (V) or formula (VI) or a pharmaceutically acceptable salt of either of them:

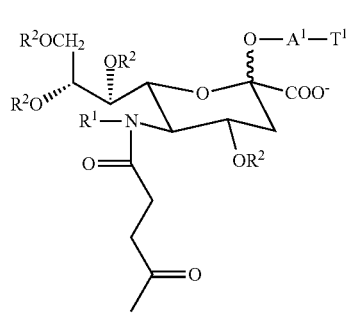
(V)

or

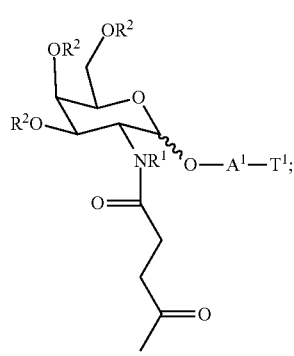
(VI)

wherein:

R¹ represents H or tri((C₁-C₆)alkyl)silyl;

R², independently for each occurrence, represents H, —C(O)((C₁-C₆)alkyl, galactosyl, N-acetylgalactosamino, mannosyl, N-acetylmannosamino, glucosyl, N-acetylglucosamino, maltosyl, or fructosyl;

A¹ represents the self-immolative linker; and

T¹ represents the trigger-responsive moiety.

The variables in formula (V) and (VI) may be further selected as described above and below.

In some embodiments, the compound is represented by formula (V) or a pharmaceutically acceptable salt thereof:

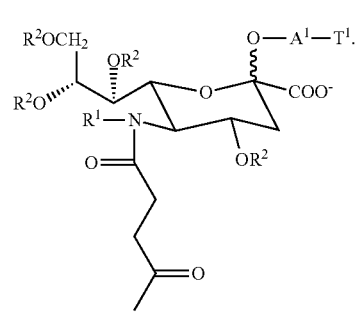
(V)

In some embodiments, the compound is represented by formula (VI) or a pharmaceutically acceptable salt thereof:

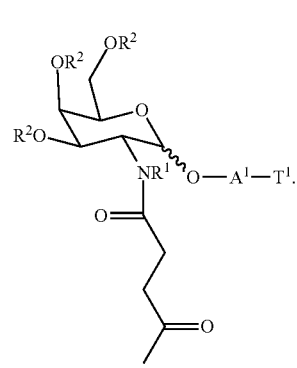
(VI)

Pharmacophore Derivatives

In other aspects, the invention relates to compounds that can deliver therapeutic agents selectively to cells that express an azidosugar (e.g., an azido sialic acid) on their cell surface. Accordingly, in certain embodiments, the invention relates to a compound of formula (VII):

$$K\text{-Pol-Pep-}A^2\text{-D} \qquad (VII);$$

wherein:

K represents an optionally substituted cycloalkynyl, heterocycloalkynyl, or alkynyl moiety;

Pol represents a polymeric moiety;

Pep represents an amino acid or oligopeptide sequence;

A² represents a self-immolative linker; and

D represents a pharmacophore;

wherein:

the polymeric moiety is a polyalkylene glycol or polyalkylene imide; and the amino acid or oligopeptide sequence comprises an amide bond that is cleaved by an enzyme (i) overexpressed in a malignant cell relative to a counterpart healthy cell or (ii) expressed in a malignant cell that is not expressed in a counterpart healthy cell.

In certain embodiments, upon cleavage of the amide bond by the enzyme, the self-immolative linker disassembles, thereby releasing the pharmacophore.

In certain embodiments, the enzyme is a cathepsin enzyme. For example, the enzyme can be cathepsin B.

In certain embodiments, Pep represents optionally substituted Val-Cit.

In certain embodiments, the compound of formula (VII) is represented by formula (VIII):

(VIII)

[Structure VIII shown]

wherein:
R¹, R², and R³, independently for each occurrence, represent H, tri((C₁-C₆)alkyl)silyl, or —C(O)((C₁-C₆)alkyl).
In certain embodiments, R¹, R², and R³ are H.
The variables in formulas (VII) and (VIII) may be further selected as described above and below.
In certain embodiments of the compounds disclosed herein, K comprises an optionally substituted heterocycloalkynyl or cycloalkynyl. In certain embodiments, K comprises an optionally substituted dibenzocyclooctyne (DBCO) moiety.
In certain embodiments, Pol represents a polyethylene glycol or polypropylene glycol moiety.
In certain embodiments, Pol represents from 0 to 5000 repeat units of polyethylene glycol or polypropylene glycol.
In certain embodiments, Pol represents from 0 to 5000 repeat units of polyethylene glycol.
In certain embodiments, Pol represents from 10 to 30 repeat units of polyethylene glycol or polypropylene glycol.
In certain embodiments, Pol represents from 10 to 30 repeat units of polyethylene glycol, or from 4 to 30 repeat units of polyethylene glycol, or from 15 to 25 repeat units of polyethylene glycol.
In certain embodiments of the compounds disclosed herein,
A² represents a group —Y²—X²—;
X² represents a bond or —C(O)₂—;
Y² represents a bond or optionally substituted -arylene-((C₁)alkylene)- or -heteroarylene-((C₁)alkylene)-; and
X² and Y² do not both represent a bond.
In certain embodiments, Y² represents optionally substituted -arylene-((C₁)alkylene)-.
In certain such embodiments, the self-immolative linker is selected from the group consisting of:

[Several self-immolative linker structures shown]

wherein
R⁶ represents H, tri((C₁-C₆)alkyl)silyl, or —C(O)((C₁-C₆)alkyl);
R⁷ represents H, (C₁-C₆)alkyl, or heterocycloalkyl;
R⁸ represents H, halo, —C(O)₂H, (C₁-C₆)alkoxy, di((C₁-C₆)alkyl)amino, —NO₂, —O(CH₂CH₂O)$_q$CH₃;
m is 1, 2, 3, 4, or 5; and
q is 1 or 2.
In certain such embodiments, R⁸ is H.
In certain embodiments, the self-immolative linker is

[Structure shown]

In some embodiments of the compounds disclosed herein, the compound further comprises a sugar linker comprising one or more sugar moieties, wherein A² further comprises said sugar linker. In some embodiments, the self-immolative linker disassembles, thereby releasing the pharmacophore.

In some embodiments of the compounds disclosed herein, the one or more sugar moieties are selected from the group consisting of galactosyl, N-acetylgalactosamino, mannosyl, N-acetylmannosamino, neuraminic acid, glucosyl, N-acetylglucosamino, maltosyl, or fructosyl.

In alternative embodiments, the self-immolative linker is selected from the group consisting of:

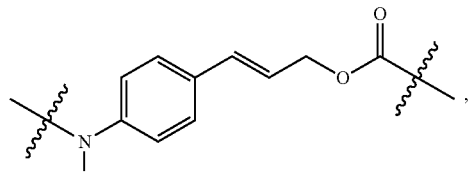

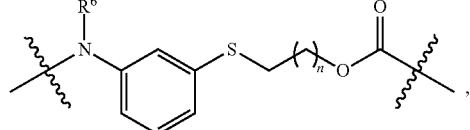

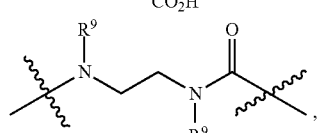

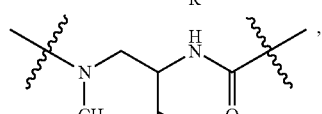

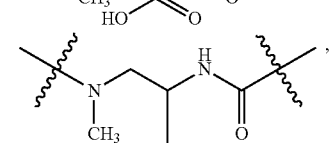

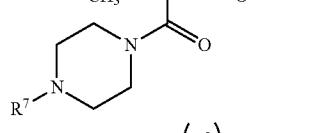

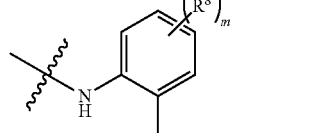

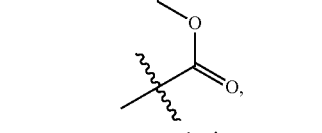

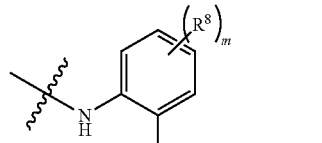

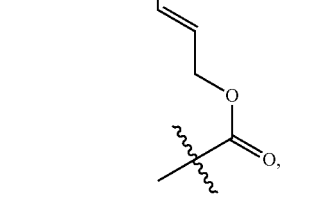

-continued

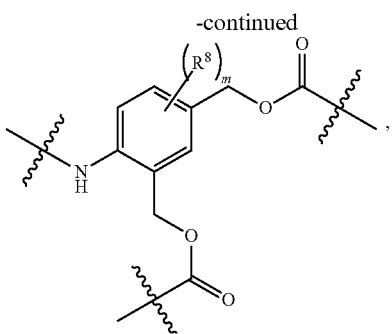

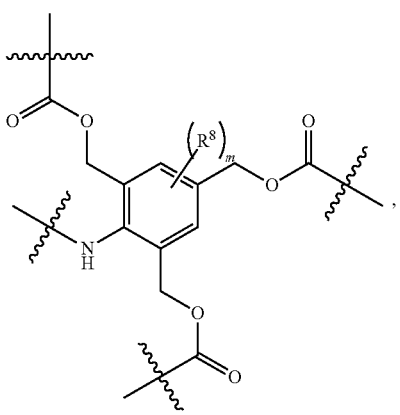

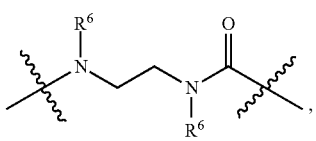

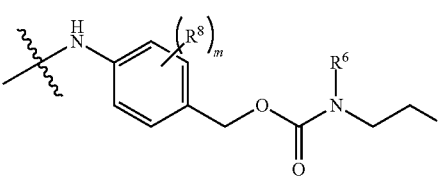

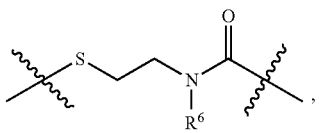

, and

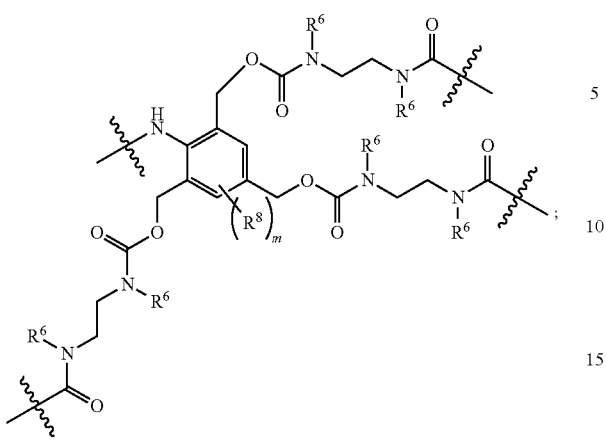
wherein
$R^6$ represents H, tri(($C_1$-$C_6$)alkyl)silyl, or —C(O)(($C_1$-$C_6$)alkyl);
$R^7$ represents H, ($C_1$-$C_6$)alkyl, or heterocycloalkyl;
$R^8$ represents H, halo, —C(O)$_2$H, ($C_1$-$C_6$)alkoxy, di(($C_1$-$C_6$)alkyl)amino, —NO$_2$, —O(CH$_2$CH$_2$O)$_q$CH$_3$;
$R^9$ represents H or ($C_1$-$C_6$)alkyl;
m is 1, 2, 3, 4, or 5;
n is 1 or 2; and
q is 1 or 2.
In some embodiments, the self-immolative linker is selected from the group consisting of:
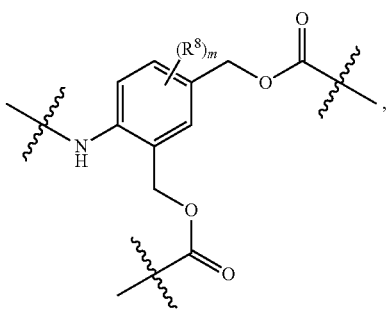
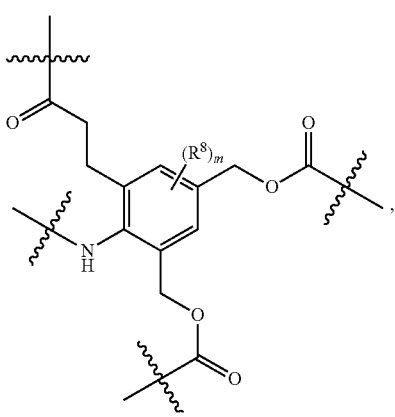
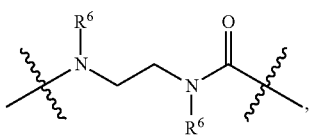
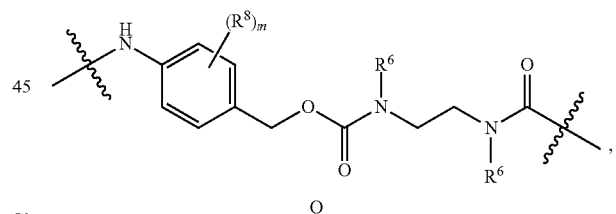
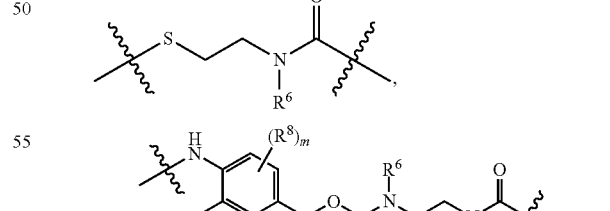
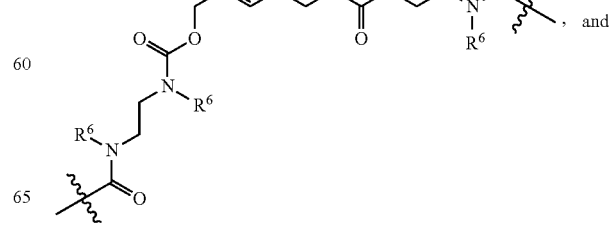

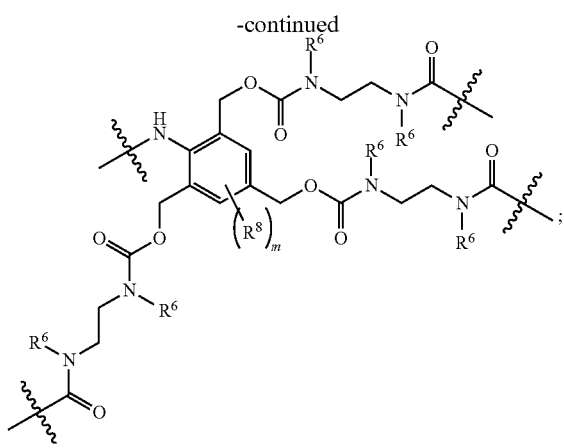

wherein
R⁶ represents H, tri(($C_1$-$C_6$)alkyl)silyl, or —C(O)(($C_1$-$C_6$)alkyl);
R⁷ represents H, ($C_1$-$C_6$)alkyl, or heterocycloalkyl;
R⁸ represents H, halo, —C(O)₂H, ($C_1$-$C_6$)alkoxy, di(($C_1$-$C_6$)alkyl)amino, —NO₂, —O(CH₂CH₂O)$_q$CH₃;
R⁹ represents H or ($C_1$-$C_6$)alkyl;
m is 1, 2, 3, 4, or 5; and
q is 1 or 2.

In certain embodiments, the disclosure relates to a compound of formula (IX) or a pharmaceutically acceptable salt thereof:

$$K\text{-Pol-}L^1\text{-D} \qquad (IX);$$

wherein:
K represents an optionally substituted cycloalkynyl, heterocycloalkynyl, or alkynyl moiety;
Pol represents a polymeric moiety;
L¹ represents a linker comprising a moiety selected from the group consisting of amido, ester, maleimido, imino, sulfide, disulfide, hydrazono, and oximo;
and
D represents a pharmacophore;
wherein:
the polymeric moiety is a polyalkylene glycol or polyalkylene imide.

The variables in formula (IX) may be further selected as described above and below.

In some embodiments, L¹ represents a linker comprising an amido moiety.

In some embodiments, L¹ represents a linker comprising a moiety selected from the group consisting of:

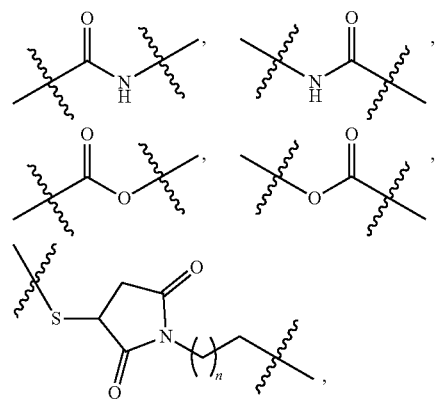

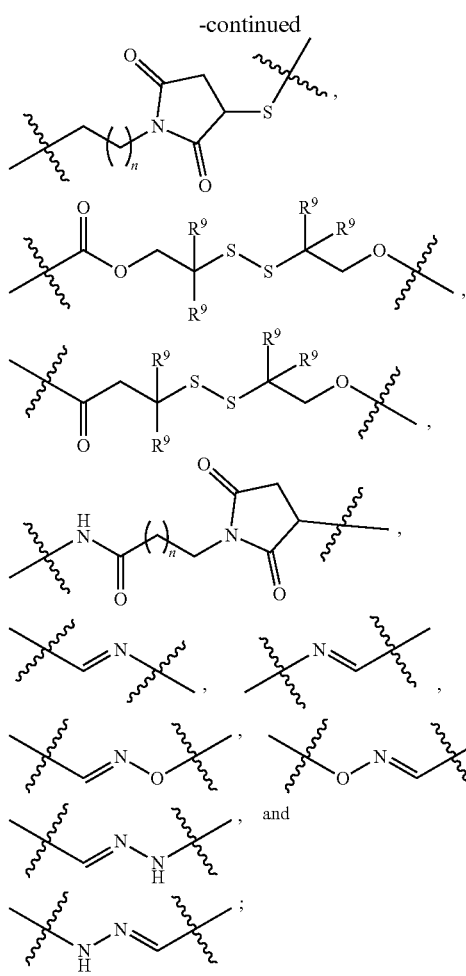

wherein
R⁹ represents H or ($C_1$-$C_6$)alkyl; and
n is 1 or 2.

In some embodiments, the linker is

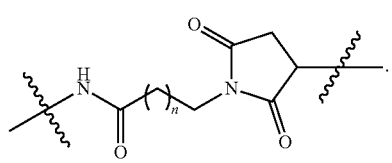

In some embodiments, n is 1.

In some embodiments, the compound of formula (IX) is represented by formula (X):

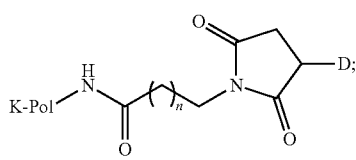

(X)

wherein:
n is 1 or 2.

In some embodiments, the disclosure relates to a compound of formula (XI) or a pharmaceutically acceptable salt thereof:

$$K\text{-Pol-}L^2\text{-D} \qquad (XI);$$

wherein:
K represents an optionally substituted cycloalkynyl, heterocycloalkynyl, or alkynyl moiety;
Pol represents a polymeric moiety;
$L^2$ is absent or represents a trigger-responsive moiety; and
D represents a pharmacophore;
wherein:
the polymeric moiety is a polyalkylene glycol or polyalkylene imide.

The variables in formula (XI) may be further selected as described above and below.

In certain embodiments, the trigger is heightened, overexpressed, or otherwise enhanced in a cancerous tissue relative to a healthy tissue.

In certain embodiments, the trigger is cellular peroxide.

In certain such embodiments, the trigger-responsive moiety comprises a boronic acid group, a dialkyl boronate group, a diaryl boronate group, a di(aralkyl)boronate group, a borolane group, or a dioxaborolane group.

In certain such embodiments, upon cleavage of the trigger-responsive moiety by cellular peroxide the compound disassembles, thereby releasing the pharmacophore.

In alternative embodiments, the trigger is hypoxia.

In certain such embodiments, the trigger-responsive moiety comprises a 2-nitroimidazole moiety or an azo group, such as azobenzene.

In certain such embodiments, upon cleavage of the trigger-responsive moiety under hypoxic conditions the compound disassembles, thereby releasing the pharmacophore.

In alternative embodiments, the trigger is a sulfhydryl- or thiolate-containing compound, such as glutathione.

In certain such embodiments, the trigger-responsive moiety comprises a disulfide bond.

In certain such embodiments, upon cleavage of the disulfide bond by a sulfhydryl- or thiolate-containing compound the compound disassembles, thereby releasing the pharmacophore.

In alternative embodiments, the trigger is NAD(P)H dehydrogenase (quinone 1) (NQO1).

In certain such embodiments, the trigger-responsive moiety comprises an optionally substituted quinone, covalently bound to an optionally substituted propionic acid or propionic amide moiety.

In certain such embodiments, upon cleavage of the optionally substituted quinone, covalently bound to an optionally substituted propionic acid or propionic amide moiety by NAD(P)H dehydrogenase (quinone 1) (NQO1) the compound disassembles, thereby releasing the pharmacophore.

In certain embodiments, the trigger is a cathepsin enzyme.

In certain such embodiments, the trigger-responsive moiety is an amino acid or oligopeptide sequence comprising an amide bond that is a cleaved by a cathepsin enzyme.

In further embodiments, the trigger-responsive group comprises an acid-sensitive moiety, such as an imine, acetal, ketal, or carbamate.

In certain such embodiments, the amino acid or oligopeptide sequence comprising an amide bond comprises Phe-Lys, Val-Lys, Ala-Lys, Val-Cit, Phe-Cit, Leu-Cit, Ile-Cit, Trp-Cit, Phe-Arg(NO$_2$), Phe-Arg(Ts), or Lys-Gly-Arg-Arg. Cit represents citrulline, and Ts represents a tosylate protecting group.

In certain embodiments, the amino acid or oligopeptide sequence is a substituted lysine amide.

In certain such embodiments, upon cleavage of the amide bond by the cathepsin enzyme compound disassembles, thereby releasing the pharmacophore.

In certain embodiments, the cathepsin enzyme is cathepsin L.

In certain embodiments, the pharmacophore of the compound of formula (VII), formula (VIII), formula (IX), formula (X), or formula (XI) is an antispasmodic agent, anesthetic agent, anti-inflammatory agent such as a nonsteroidal anti-inflammatory (NSAID) agent, anti-cancer therapeutic agent, calcium channel blocker, antibiotic agent, immunosuppressant, antiviral agent, anti-proliferative agent, antimicrobial agent, nerve-growth inducing agent, or smooth muscle relaxant.

In certain embodiments, the pharmacophore is an anti-cancer therapeutic agent.

In certain embodiments, the anti-cancer therapeutic agent is actinomycin-D, altretamine, aminoglutethimide, amsacrine, anastrozole, asparaginase, belactosin A, bicalutamide, bleomycin, bortezomib, buserelin, busulfan, campothecin, camptothecin, capecitabine, carboplatin, carfilzomib, carmustine, chlorambucil, chloroquine, cisplatin, cladribine, clodronate, colchicine, cyclophosphamide, cyproterone, cytarabine, dacarbazine, dactinomycin, daunorubicin, demethoxyviridin, dexamethasone, dichloroacetate, dienestrol, diethylstilbestrol, docetaxel, doxorubicin, epirubicin, epoxomicin, estradiol, estramustine, etoposide, everolimus, exemestane, fellutamide B, filgrastim, fludarabine, fludrocortisone, 5-fluorouracil, floxuridine, fluoxymesterone, flutamide, gemcitabine, genistein, goserelin, hydroxyurea, idarubicin, ifosfamide, imatinib, interferon, irinotecan, ixabepilone, lenalidomide, letrozole, leucovorin, leuprolide, levamisole, lomustine, lonidamine, marizomib, maytansine, mechlorethamine, medroxyprogesterone, megestrol, melphalan, mercaptopurine, mertansine, mesna, metformin, methotrexate, methylprednisolone, mitomycin, mitotane, mitoxantrone, monomethyl auristatin, nilutamide, nocodazole, octreotide, omuralide, oxaliplatin, paclitaxel, pamidronate, pemetrexed, pentostatin, perifosine, plicamycin, pomalidomide, porfimer, prednisone, procarbazine, raltitrexed, rituximab, sorafenib, streptozocin, sunitinib, suramin, tamoxifen, temozolomide, temsirolimus, teniposide, testosterone, thalidomide, thioguanine, thiotepa, titanocene dichloride, topotecan, trastuzumab, tretinoin, vinblastine, vincristine, vindesine, vinorelbine, SN-38, MG-132, PSI, CEP-18770, MLN-2238, MLN-9708, NC-005, YU-101, LU-005, YU-102, NC-001, LU-001, NC-022, PR-957 (LMP7), CPSI (β5), 10 LMP2-sp-ek, BODIPY-NC-001, azido-NC-002, ONX-0912, PS-519, 125I-NIP-L3VS, NC-005-VS, or MV151.

In certain embodiments, the anti-cancer therapeutic agent is doxorubicin.

In certain embodiments, the anti-cancer therapeutic agent is mertansine.

In certain embodiments of the compounds of formula (VII), formula (VIII), formula (IX), formula (X), or formula (XI), D represents a pharmacophore selected from the group consisting of:

33 34
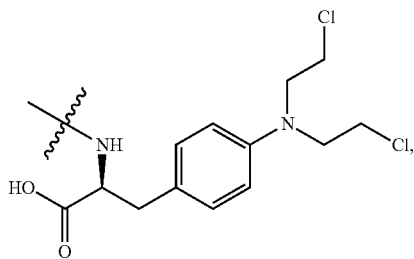
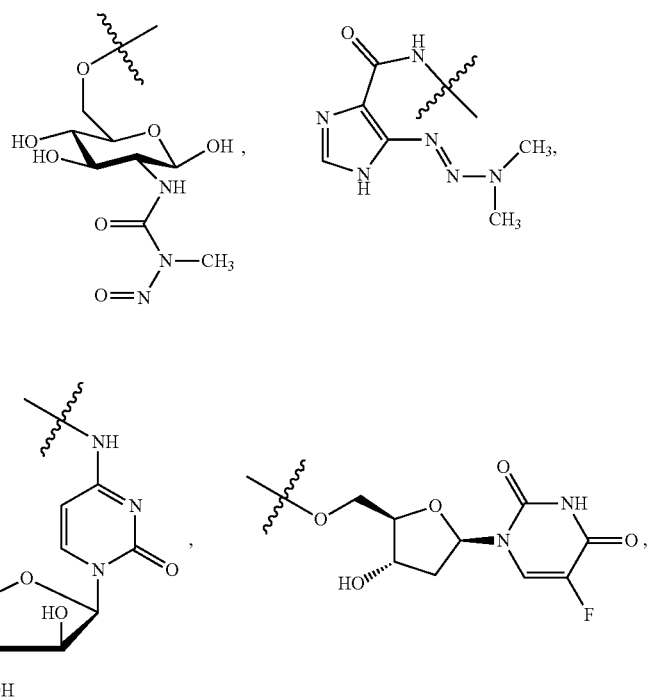
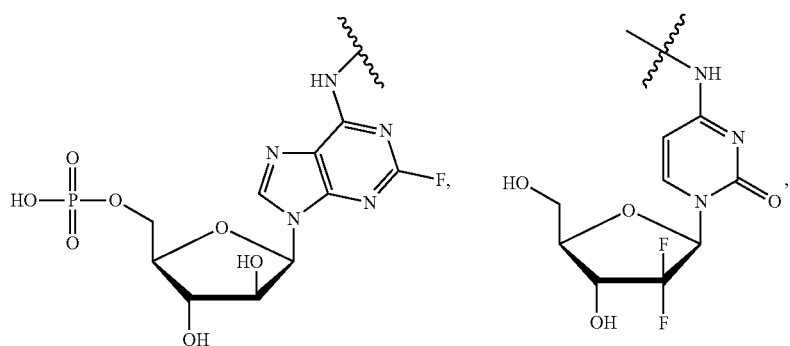
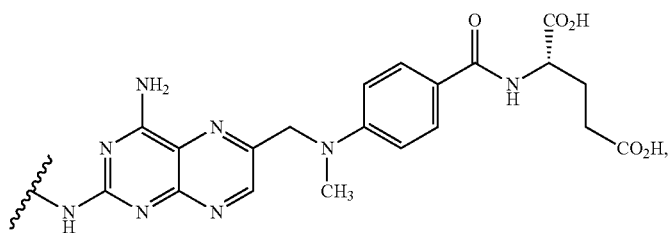
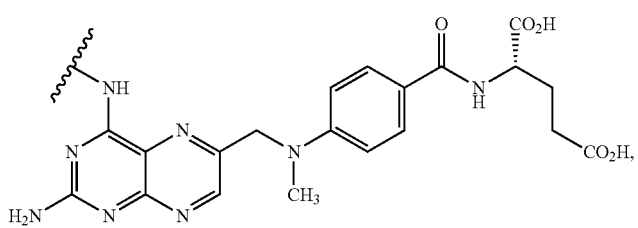

35
-continued
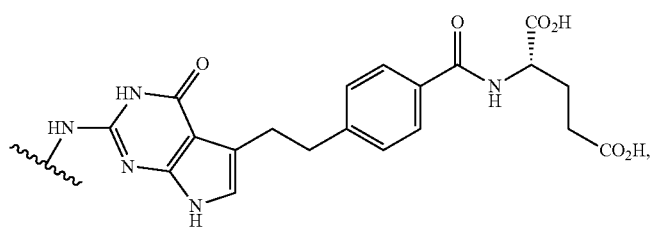
36
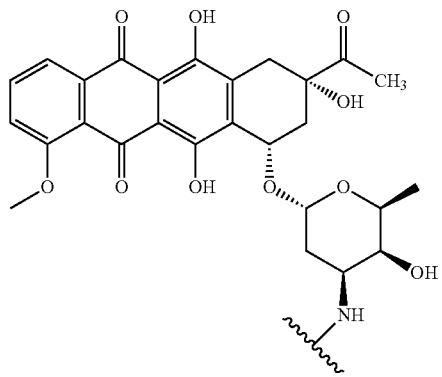
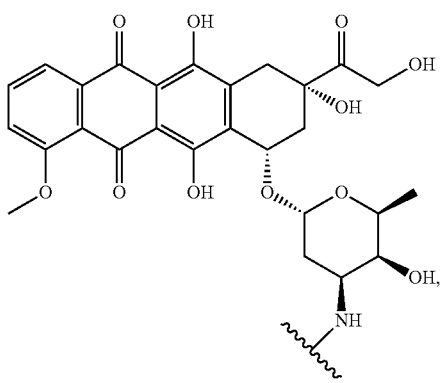
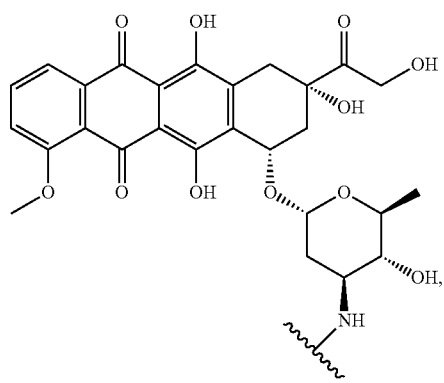
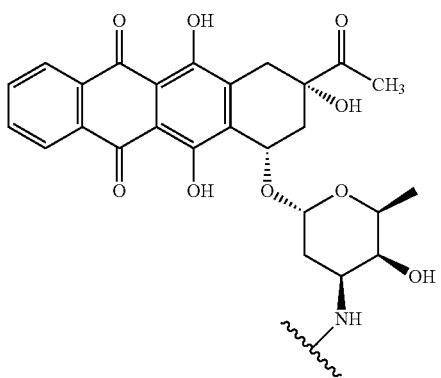
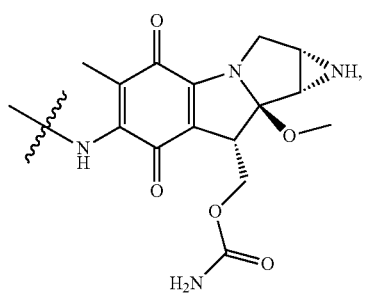
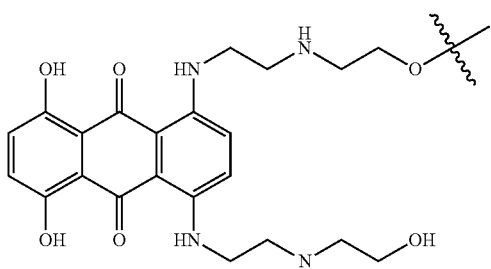
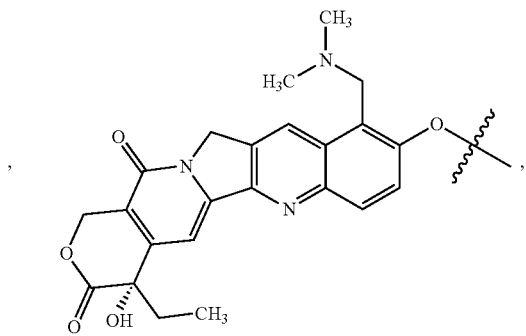

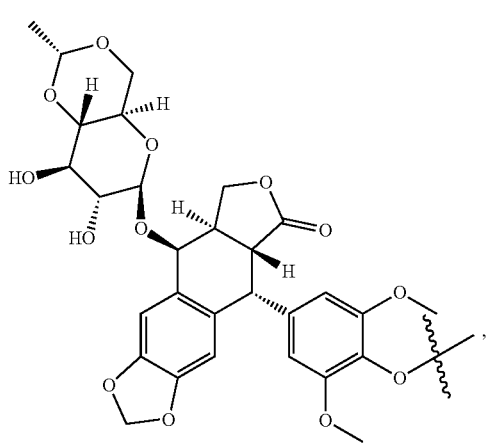
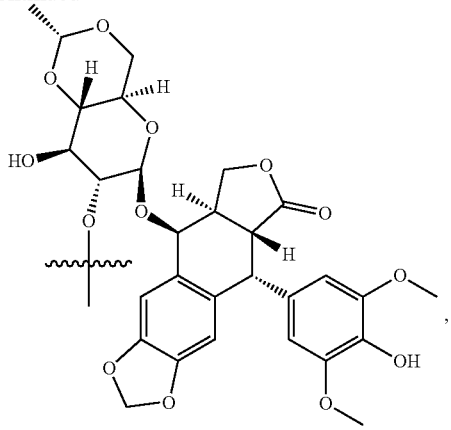
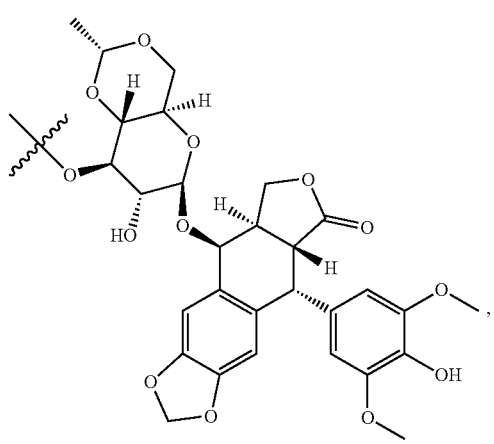
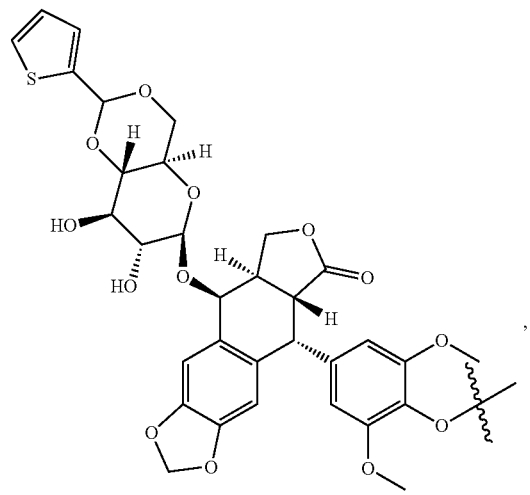
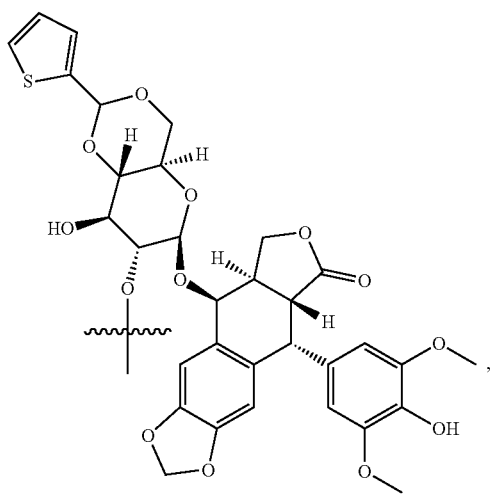
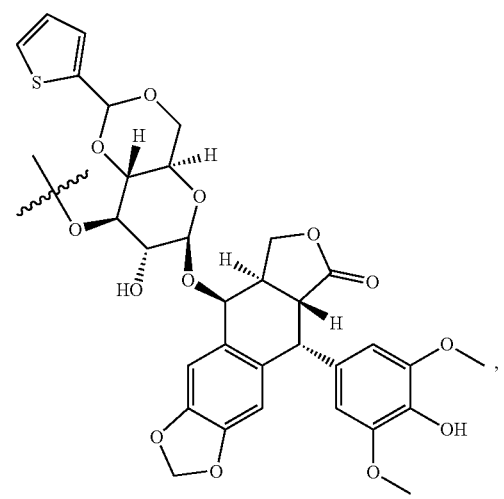

-continued
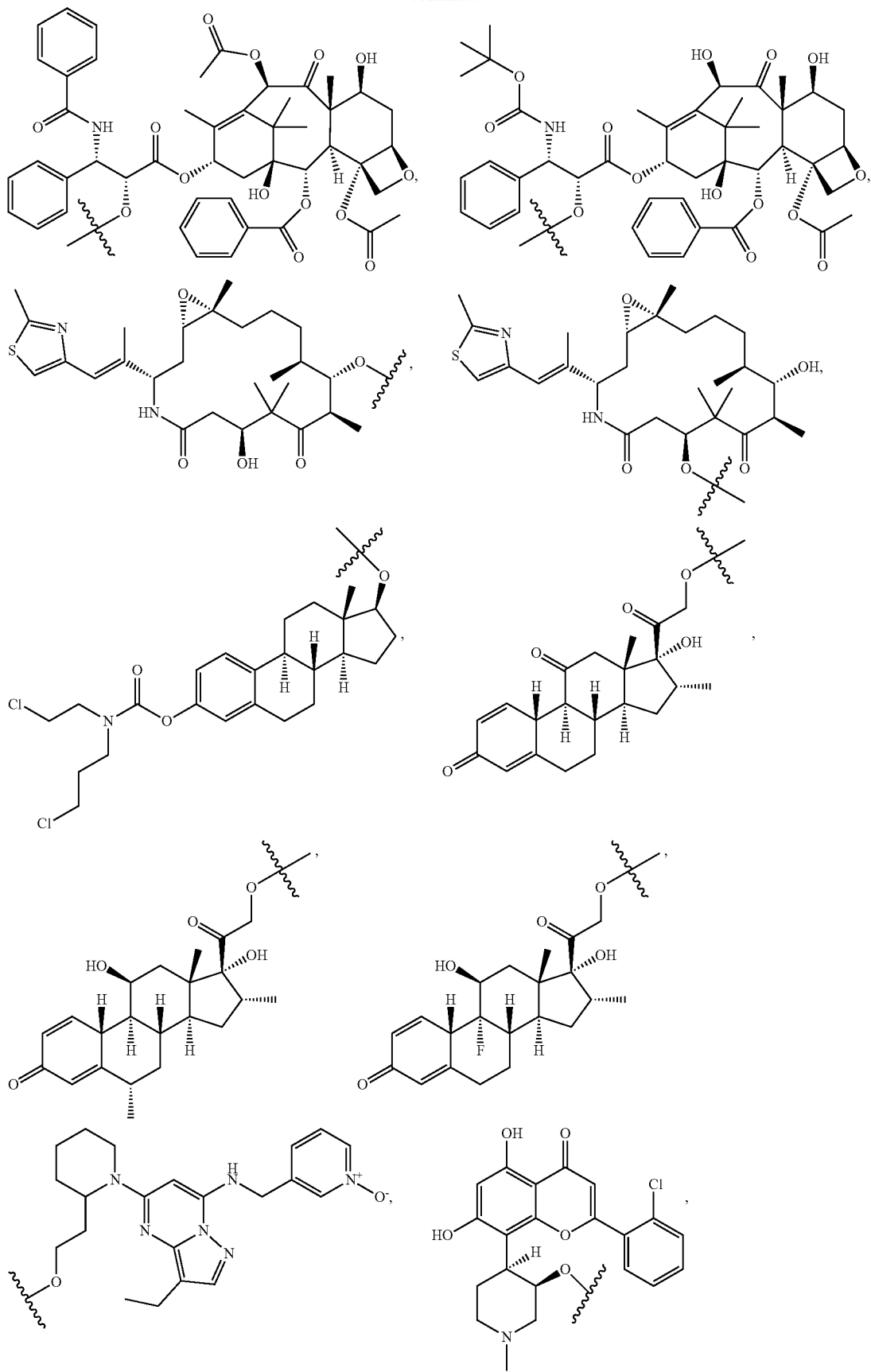

41
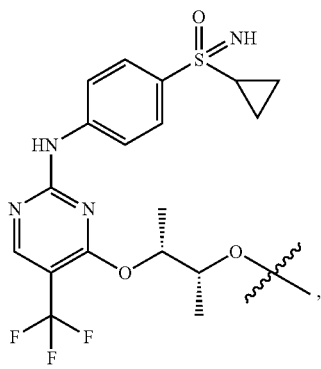
-continued
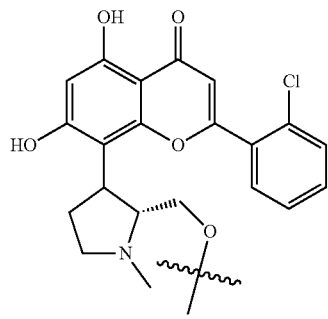
42
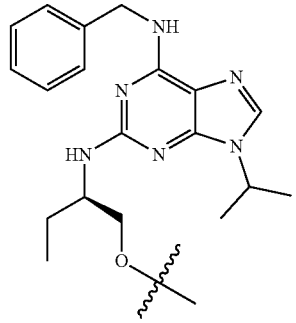
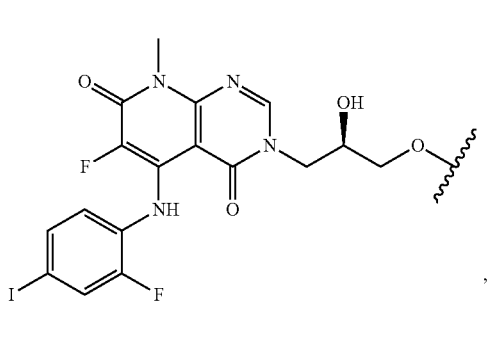
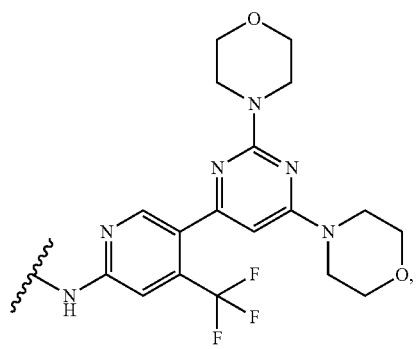
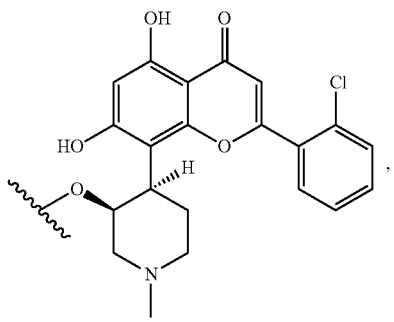
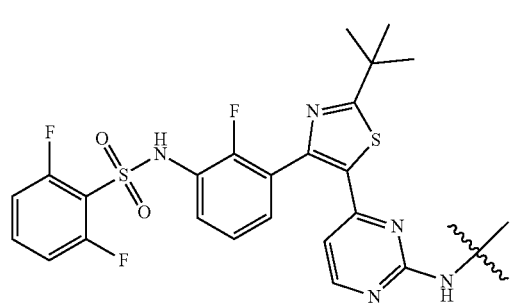
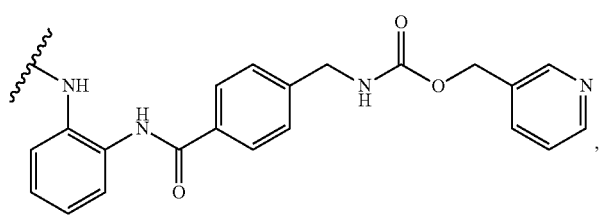
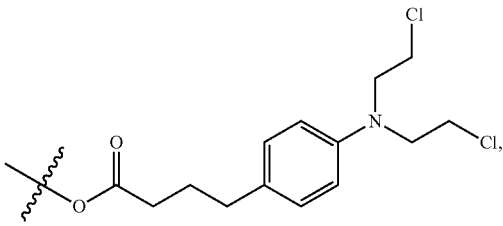
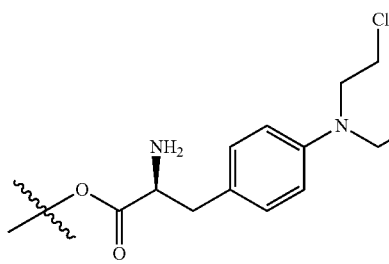
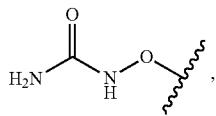

-continued
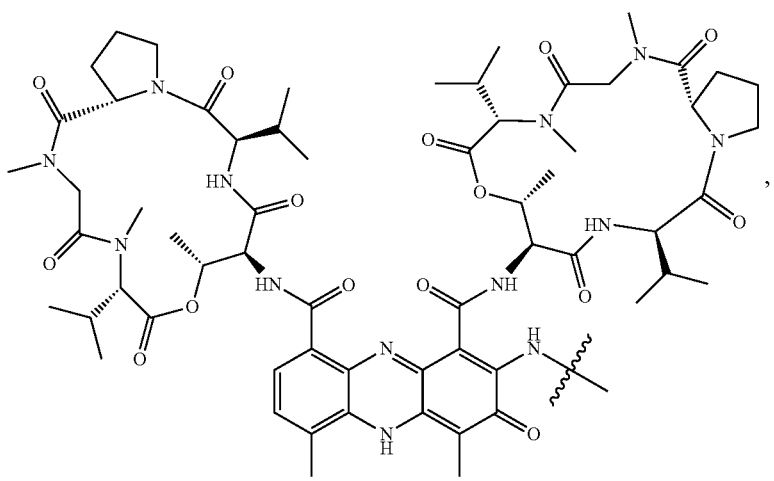
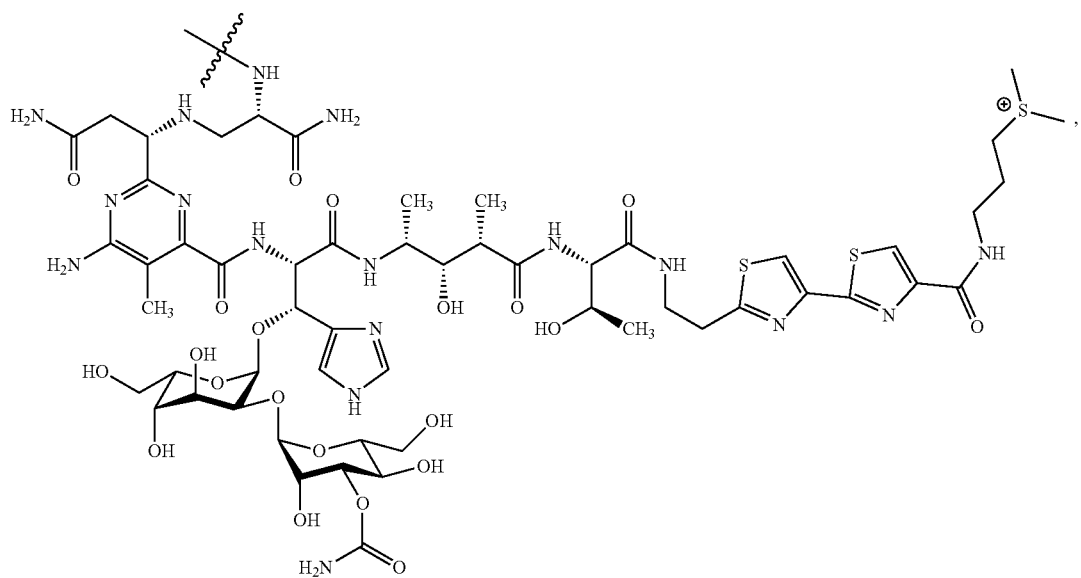
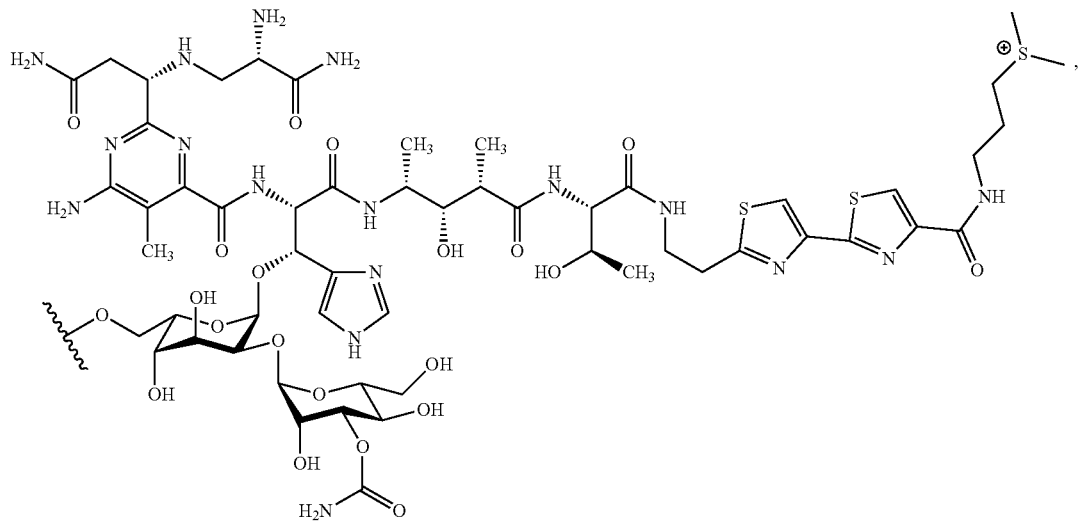

-continued
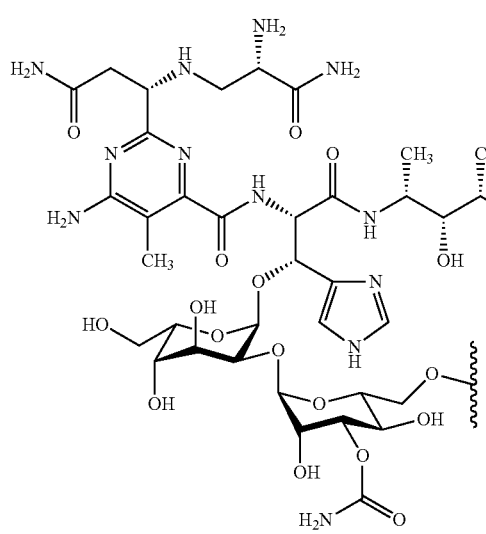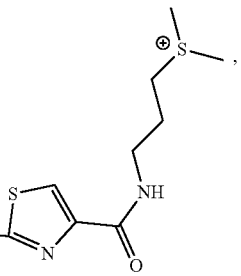
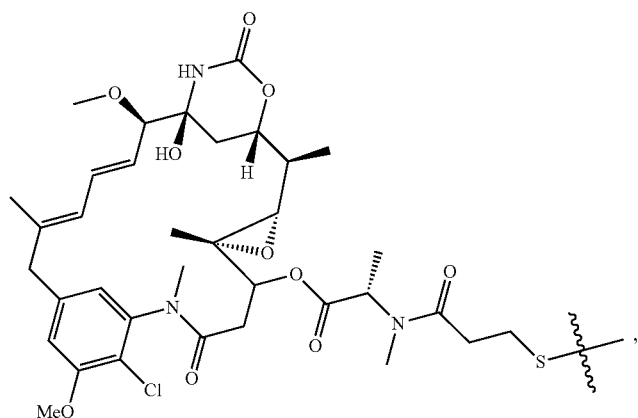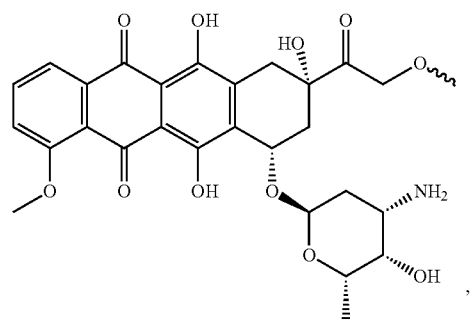
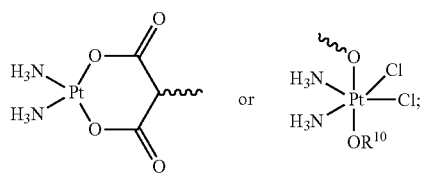
wherein
R[10] is H, C(O)((C$_1$-C$_{18}$)alkyl), C(O)—NH—((C$_1$-C$_{18}$)alkyl) or (C$_1$-C$_{18}$)alkyl.
In alternative embodiments, D represents a pharmacophore selected from the group consisting of:
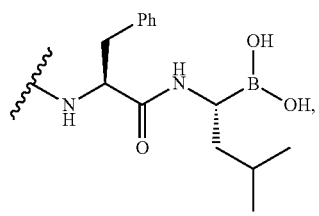
-continued
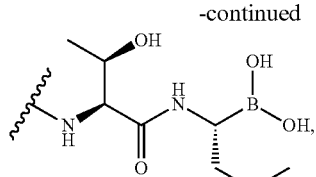
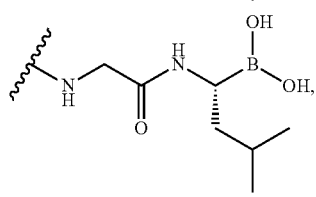

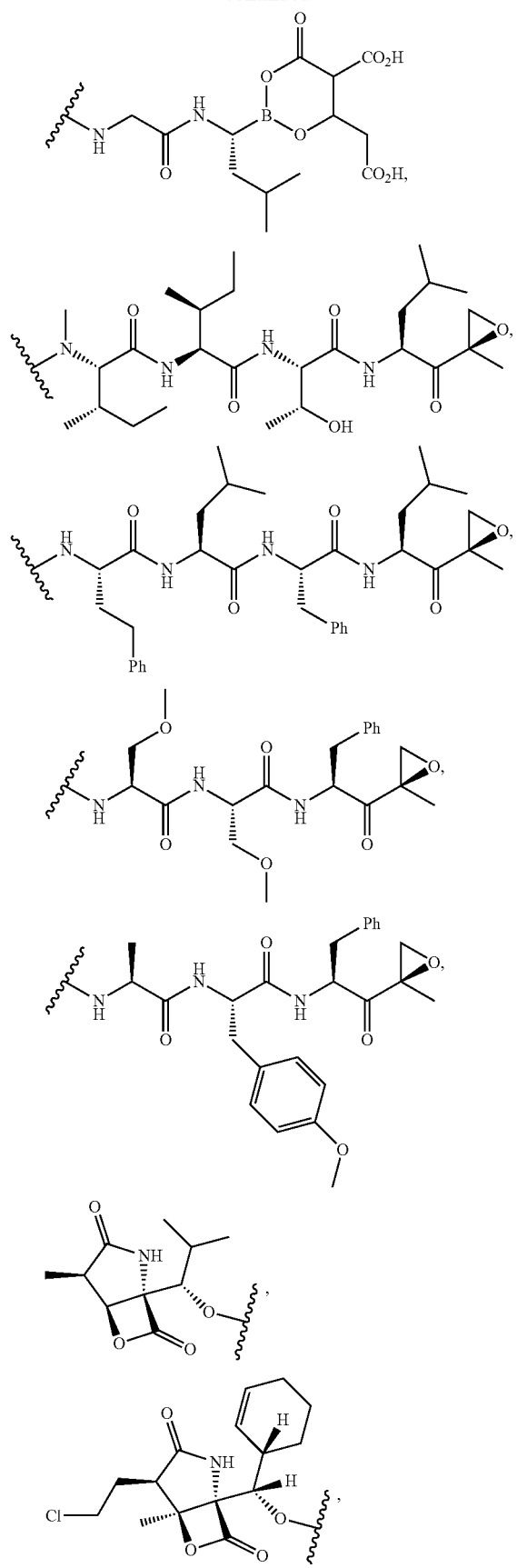
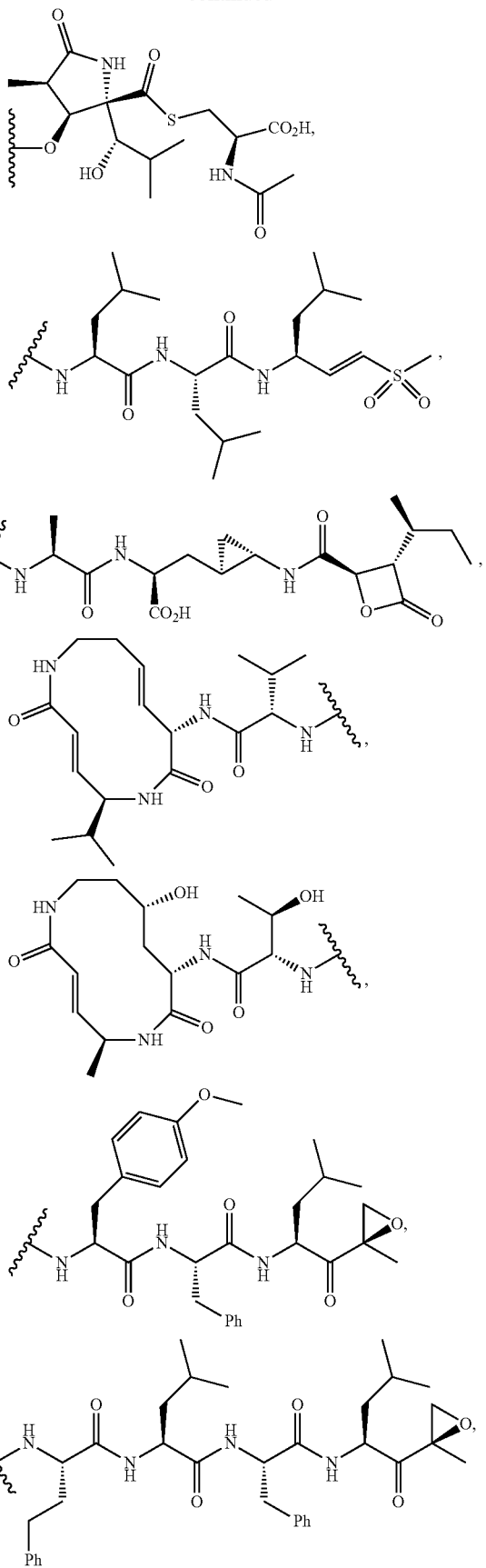

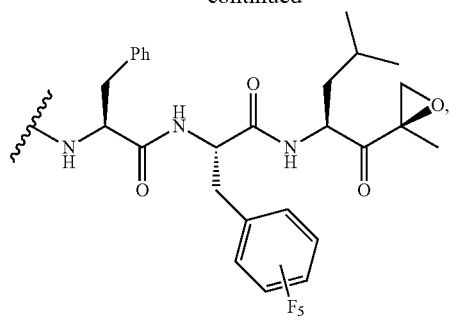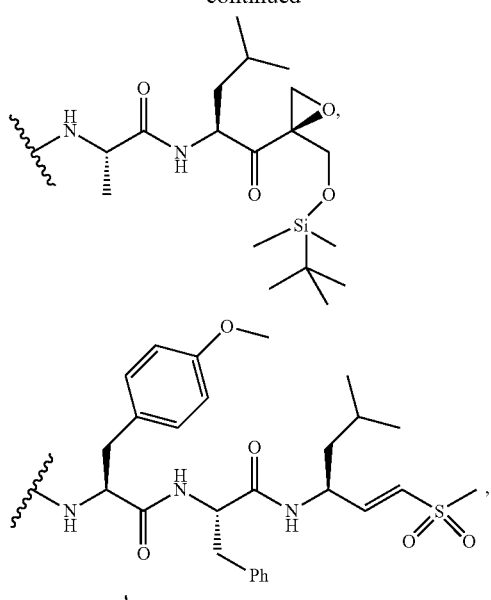
In certain embodiments, the compound of formula (VII) is represented by:

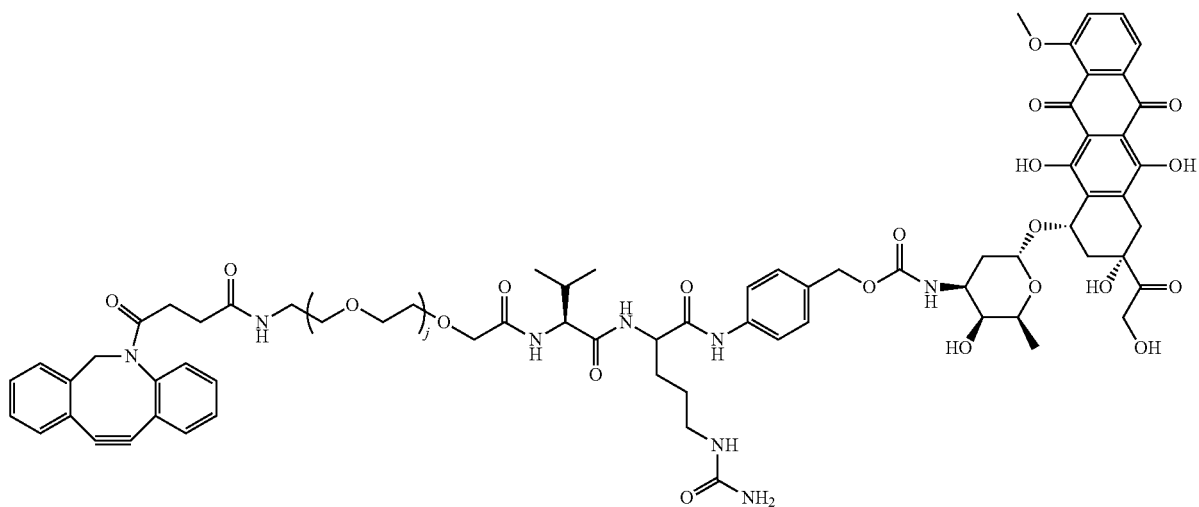
wherein j is an integer from 0-5000.
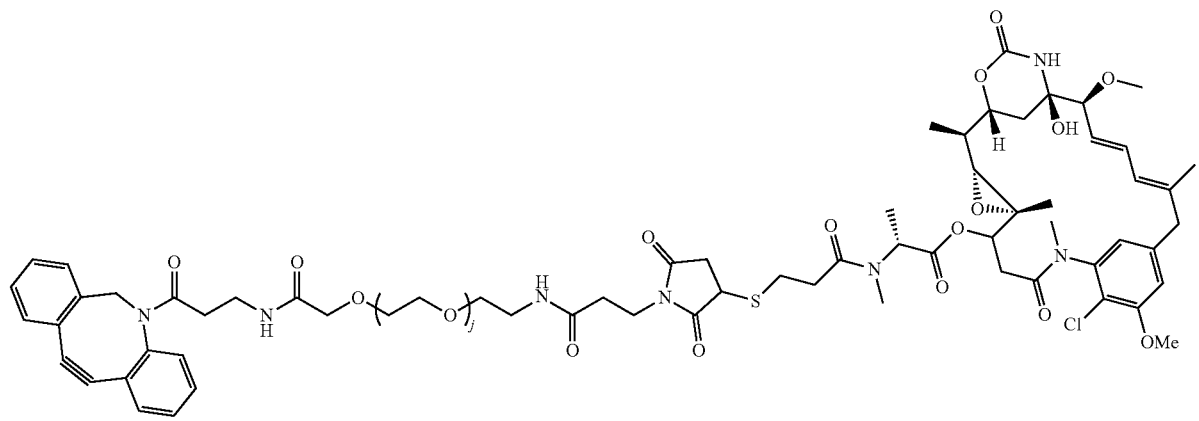
wherein j is an integer from 0-5000.
In other embodiments, the present disclosure provides compounds having the formula:
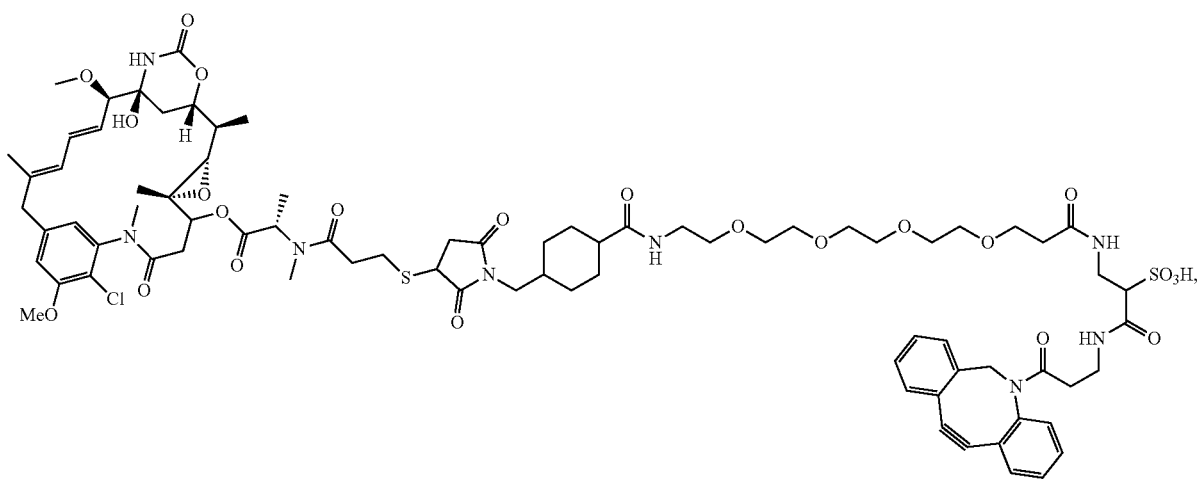

-continued

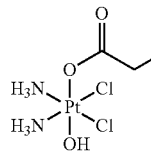
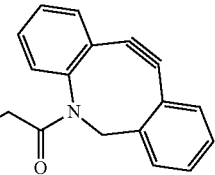
, or

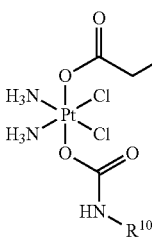
;

wherein
R$^{10}$ is H or (C$_1$-C$_{18}$)alkyl;
or a pharmaceutically acceptable salt thereof.

In certain aspects, the invention relates to pharmaceutical compositions comprising a compound of the invention, or a pharmaceutically acceptable salt thereof, and a pharmaceutically acceptable excipient or carrier. Pharmaceutically acceptable excipients and carriers are described in detail below.

Methods of Treatment

In certain aspects, the invention relates to methods of expressing an azidosugar (e.g., an azido sialic acid; see FIGS. 1 and 2, panel b) on a surface of a cancer cell, comprising:
contacting a cancer cell with a compound;
wherein the compound is described herein, and comprises an optionally substituted N-((azido)acyl) 5-amino-3,5-dideoxy-D-glycero-D-galacto-2-nonulopyranosonic acid moiety or an optionally substituted N-((azido)acyl) 2-amino-2-deoxy-D-galactopyranosyl moiety; a trigger-responsive moiety that is cleaved by a trigger; and a self-immolative linker; wherein the self-immolative linker is covalently bonded to the nonulopyranosonic acid moiety or the galactopyranosyl moiety, and to the trigger-responsive moiety;
thereby expressing the azidosugar on the surface of the cancer cell.

In certain aspects, the methods of expressing an azidosugar on a surface of a cancer cell, comprising contacting a cancer cell with a compound of formula (I), formula (II), formula (IIa), formula (V), or formula (VI); thereby expressing the azidosugar on the surface of the cancer cell.

In certain aspects, the invention provides methods of treating cancer, comprising administering to a subject in need thereof a therapeutically effective amount of a compound as described herein, wherein the compound comprises an optionally substituted N-((azido)acyl) 5-amino-3,5-dideoxy-D-glycero-D-galacto-2-nonulopyranosonic acid moiety or an optionally substituted N-((azido)acyl) 2-amino-2-deoxy-D-galactopyranosyl moiety; a trigger-responsive moiety that is cleaved by a trigger; and a self-immolative linker; wherein the self-immolative linker is covalently bonded to the nonulopyranosonic acid moiety or the galactopyranosyl moiety and to the trigger-responsive moiety.

In certain embodiments, such methods of treating cancer further comprise administering to the subject a therapeutically effective amount of a compound of formula (VII), formula (IX), or formula (XI).

In certain aspects, the invention provides methods of treating cancer, comprising administering to a subject in need thereof a therapeutically effective amount of a compound of formula (VII), formula (IX), or formula (XI).

In certain embodiments, the cancer is selected from Acute Lymphoblastic Leukemia (ALL), Acute Myeloid Leukemia (AML), Adrenocortical Carcinoma, AIDS-Related Cancers (Kaposi Sarcoma and Lymphoma), Anal Cancer, Appendix Cancer, Atypical Teratoid/Rhabdoid Tumor, Basal Cell Carcinoma, Bile Duct Cancer (including Extrahepatic), Bladder Cancer, Bone Cancer (including Osteosarcoma and Malignant Fibrous Histiocytoma), Brain Tumor (such as Astrocytomas, Brain and Spinal Cord Tumors, Brain Stem Glioma, Central Nervous System Atypical Teratoid/Rhabdoid Tumor, Central Nervous System Embryonal Tumors, Craniopharyngioma, Ependymoblastoma, Ependymoma, Medulloblastoma, Medulloepithelioma, Pineal Parenchymal Tumors of Intermediate Differentiation, Supratentorial Primitive Neuroectodermal Tumors and Pineoblastoma), Breast Cancer, Bronchial Tumors, Burkitt Lymphoma, Basal Cell Carcinoma, Bile Duct Cancer (including Extrahepatic), Bladder Cancer, Bone Cancer (including Osteosarcoma and Malignant Fibrous Histiocytoma), Carcinoid Tumor, Carcinoma of Unknown Primary, Central Nervous System (such as Atypical Teratoid/Rhabdoid Tumor, Embryonal Tumors and Lymphoma), Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma (Mycosis Fungoides and Sézary Syndrome), Duct, Bile (Extrahepatic), Ductal Carcinoma In Situ (DCIS), Embryonal Tumors (Central Nervous System), Endometrial Cancer, Ependymoblastoma, Ependymoma, Esophageal Cancer, Esthesioneuroblastoma, Ewing Sarcoma Family of Tumors, Extracranial Germ Cell Tumor, Extragonadal Germ Cell Tumor, Extrahepatic Bile Duct Cancer, Eye Cancer (like Intraocular Melanoma, Retinoblastoma), Fibrous Histiocytoma of Bone (including Malignant and Osteosarcoma) Gallbladder Cancer, Gastric (Stomach) Cancer, Gastrointestinal Carcinoid Tumor, Gastrointestinal Stromal Tumors (GIST), Germ Cell Tumor (Extracranial, Extragonadal, Ovarian), Gestational Trophoblastic Tumor, Glioma, Hairy Cell Leukemia, Head and Neck Cancer, Heart Cancer, Hepatocellular (Liver) Cancer, Histiocytosis, Langerhans Cell, Hodgkin Lymphoma, Hypopharyngeal Cancer, Intraocular Melanoma, Islet Cell Tumors (Endocrine, Pancreas), Kaposi Sarcoma, Kidney (including Renal Cell), Langerhans Cell Histiocytosis, Laryngeal Cancer, Leukemia (including Acute Lymphoblastic (ALL), Acute Myeloid (AML), Chronic Lymphocytic (CLL), Chronic Myelogenous (CML), Hairy Cell), Lip and Oral Cavity Cancer, Liver Cancer (Primary), Lobular Carcinoma In Situ (LCIS), Lung Cancer (Non-Small Cell and Small Cell), Lymphoma (AIDS-Related, Burkitt, Cutaneous T-Cell (Mycosis Fungoides and Sézary Syndrome), Hodgkin, Non-Hodgkin, Primary Central Nervous System (CNS), Macroglobulinemia, Waldenström, Male Breast Cancer, Malignant Fibrous Histiocytoma of Bone and Osteosarcoma, Medulloblastoma, Medulloepithelioma, Melanoma (including Intraocular (Eye)), Merkel Cell Carcinoma, Mesothelioma (Malignant), Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic (CML), Myeloid Leukemia, Acute (AML), Myeloma and Multiple Myeloma, Myeloproliferative Disorders (Chronic), Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and, Oropharyngeal Cancer, Osteosarcoma and Malignant Fibrous Histiocytoma of Bone, Ovarian Cancer (such as Epithelial, Germ Cell Tumor, and Low Malignant Potential Tumor), Pancreatic Cancer (including Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pineal Parenchymal Tumors of Intermediate Differentiation, Pineoblastoma and Supratentorial Primitive Neuroectodermal Tumors, Pituitary Tumor, Plasma Cell Neoplasm/Multiple Myeloma, Pleuropulmonary Blastoma, Pregnancy and Breast Cancer, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (like Ewing Sarcoma Family of Tumors, Kaposi, Soft Tissue, Uterine), Sézary Syndrome, Skin Cancer (such as Melanoma, Merkel Cell Carcinoma, Nonmelanoma), Small Cell Lung Cancer, Small Intestine Cancer, Soft Tissue Sarcoma, Squamous Cell Carcinoma, Squamous Neck Cancer with Occult Primary, Metastatic, Stomach (Gastric) Cancer, Supratentorial Primitive Neuroectodermal Tumors, T-Cell Lymphoma (Cutaneous, Mycosis Fungoides and Sézary Syndrome), Testicular Cancer, Throat Cancer, Thymoma and Thymic Carcinoma, Thyroid Cancer, Transitional Cell Cancer of the Renal Pelvis and Ureter, Trophoblastic Tumor (Gestational), Unknown Primary, Unusual Cancers of Childhood, Ureter and Renal Pelvis, Transitional Cell Cancer, Urethral Cancer, Uterine Cancer, Endometrial, Uterine Sarcoma, Waldenström Macroglobulinemia and Wilms Tumor.

In certain embodiments, the subject is a mammal, e.g., a human.

Definitions

The phrase "protecting group" as used herein means substituents which protect the reactive functional group from undesirable chemical reactions. Examples of such protecting groups include esters of carboxylic acids and boronic acids, ethers of alcohols, and acetals and ketals of aldehydes and ketones. For instance, the phrase "N-terminal protecting group" or "amino-protecting group" as used herein refers to various amino-protecting groups which can be employed to protect the N-terminus of an amino acid or peptide against undesirable reactions during synthetic procedures. Examples of suitable groups include acyl protecting groups such as, to illustrate, formyl, dansyl, acetyl, benzoyl, trifluoroacetyl, succinyl, and methoxysuccinyl; aromatic urethane protecting groups as, for example, benzyloxycarbonyl (Cbz); and aliphatic urethane protecting groups such as t-butoxycarbonyl (Boc) or 9-Fluorenylmethoxycarbonyl (Fmoc).

The term "amino-terminal protecting group" as used herein, refers to terminal amino protecting groups that are typically employed in organic synthesis, especially peptide synthesis. Any of the known categories of protecting groups can be employed, including acyl protecting groups, such as acetyl, and benzoyl; aromatic urethane protecting groups, such as benzyloxycarbonyl; and aliphatic urethane protecting groups, such as tert-butoxycarbonyl. See, for example, Gross and Mienhoffer, Eds., *The Peptides*, Academic Press: New York, 1981; Vol. 3, 3-88; and Green, T. W.; Wuts, P. G. M., *Protective Groups in Organic Synthesis*, 2nd ed, Wiley: New York, 1991. Preferred protecting groups include aryl-, aralkyl-, heteroaryl- and heteroarylalkyl-carbonyl and sulfonyl moieties.

As used herein the term "physiological conditions" refers to temperature, pH, ionic strength, viscosity, and like biochemical parameters which are compatible with a viable organism, and/or which typically exist intracellularly in a viable mammalian cell.

The term "prodrug" as used herein encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation, not injurious to the patient, and substantially non-pyrogenic. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salts" refers to the relatively non-toxic, inorganic and organic acid addition salts of the compounds of the invention. These salts can be prepared in situ during the final isolation and purification of the compound(s), or by separately reacting the purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. See, for example, Berge et al. (1977) "Pharmaceutical Salts", *J. Pharm. Sci.* 66:1-19.

In other cases, the compounds useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound of the invention. These salts can likewise be prepared in situ during the final isolation and purification of the compound(s), or by separately reacting the purified compound(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

A "therapeutically effective amount" of a compound with respect to use in treatment, refers to an amount of the compound in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "self-eliminating linker" or "self-immolative linker" refers to a temporary extender, spacer, or placeholder unit attaching two or more molecules together by chemical bonds that are cleaved under defined conditions to release the two molecules. Examples of self-eliminating linkers include, but are not limited to, p-aminobenzyloxycarbonyl (PABC), 2,4-bis(hydroxymethyl)aniline, and 4-(phenylmethylene)aniline. The self-eliminating or self-immolative linker may be linear or branched, and may link two or more of the same molecules together, or may link two or more different molecules together. The self-eliminating or self-immolative linker may degrade, decompose, or fragment under, for example, physiological conditions, acidic conditions, basic conditions, or in the presence of specific chemical agents.

The pharmacophores used in the present invention are effective for the usual purposes for which the corresponding drugs are effective, and, in certain embodiments, have superior efficacy because of the ability, inherent in the azido-sugar targeting moiety, to transport the drug to the desired cell where it is of particular benefit.

The preferred therapeutic agents for use in the present embodiments are cytotoxic drugs, such as those which are used for cancer therapy. Such drugs include, in general, alkylating agents, antimetabolites, anti-tumor antibiotics such as anthracyclines, topoisomerase inhibitors, mitotic inhibitors, and corticosteroids.

One skilled in the art may make chemical modifications to the desired compound in order to make reactions of that compound more convenient for purposes of preparing conjugates of the invention.

In certain embodiments, D is a pharmacophore having a chemically reactive functional group by means of which the pharmacophore is bonded to the self-immolative linker. In certain instances, the functional group is selected from a primary amine, a secondary amine, hydroxyl, and sulfhydryl. In certain instances, the functional group is a primary amine or a secondary amine. In certain instances, the functional group is hydroxyl.

As noted above, certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis or by derivation with a chiral auxiliary, where the resulting diastereomeric mixture is separated and the auxiliary group cleaved to provide the pure desired enantiomer. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomer.

An aliphatic chain comprises the classes of alkyl, alkenyl and alkynyl defined below. A straight aliphatic chain is limited to unbranched carbon chain moieties. As used herein, the term "aliphatic group" refers to a straight chain, branched-chain, or cyclic aliphatic hydrocarbon group and includes saturated and unsaturated aliphatic groups, such as an alkyl group, an alkenyl group, or an alkynyl group.

"Alkyl" refers to a fully saturated cyclic or acyclic, branched or unbranched carbon chain moiety having the number of carbon atoms specified, or up to 30 carbon atoms if no specification is made. For example, alkyl of 1 to 8 carbon atoms refers to moieties such as methyl, ethyl, propyl, butyl, pentyl, hexyl, heptyl, and octyl, and those moieties which are positional isomers of these moieties. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In certain embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer.

"Cycloalkyl" means mono- or bicyclic or bridged saturated carbocyclic rings, each having from 3 to 12 carbon atoms. Likewise, preferred cycloalkyls have from 5-12 carbon atoms in their ring structure, and more preferably have 6-10 carbons in the ring structure.

Unless the number of carbons is otherwise specified, "lower alkyl," as used herein, means an alkyl group, as defined above, but having from one to ten carbons, more preferably from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. Throughout the application, preferred alkyl groups are lower alkyls. In certain embodiments, a substituent designated herein as alkyl is a lower alkyl.

"Alkenyl" refers to any cyclic or acyclic, branched or unbranched unsaturated carbon chain moiety having the number of carbon atoms specified, or up to 26 carbon atoms if no limitation on the number of carbon atoms is specified; and having one or more double bonds in the moiety. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl, and tetracosenyl, in their various isomeric forms, where the unsaturated bond(s) can be located any wherein the moiety and can have either the (Z) or the (E) configuration about the double bond(s).

"Alkynyl" refers to hydrocarbyl moieties of the scope of alkenyl, but having one or more triple bonds in the moiety.

The term "alkylthio" refers to an alkyl group, as defined above, having a sulfur moiety attached thereto. In certain embodiments, the "alkylthio" moiety is represented by one of —(S)-alkyl, —(S)-alkenyl, —(S)-alkynyl, and —(S)—$(CH_2)_m$—$R^1$, wherein m and $R^1$ are defined below. Representative alkylthio groups include methylthio, ethylthio, and the like.

The terms "alkoxyl" or "alkoxy" as used herein refers to an alkyl group, as defined below, having an oxygen moiety attached thereto. Representative alkoxyl groups include methoxy, ethoxy, propoxy, tert-butoxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O— alkenyl, —O-alkynyl, —O—$(CH_2)_m$—$R^1$, where m and $R_1$ are described below.

The terms "amine" and "amino" are art-recognized and refer to both unsubstituted and substituted amines, e.g., a moiety that can be represented by the formulae:

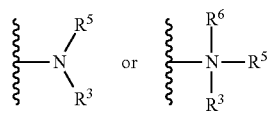

wherein $R^3$, $R^5$ and $R^6$ each independently represent a hydrogen, an alkyl, an alkenyl, —$(CH_2)_m$—$R^1$, or $R^3$ and $R^5$ taken together with the N atom to which they are attached complete a heterocycle having from 4 to 8 atoms in the ring structure; $R^1$ represents an alkenyl, aryl, cycloalkyl, a cycloalkenyl, a heterocyclyl, or a polycyclyl; and m is zero or an integer in the range of 1 to 8. In certain embodiments, only one of $R^3$ or $R^5$ can be a carbonyl, e.g., $R^3$, $R^5$, and the nitrogen together do not form an imide. In even more certain embodiments, $R^3$ and $R^5$ (and optionally $R^6$) each independently represent a hydrogen, an alkyl, an alkenyl, or —$(CH_2)_m$—R. Thus, the term "alkylamine" as used herein means an amine group, as defined above, having a substituted or unsubstituted alkyl attached thereto, i.e., at least one of $R_3$ and $R_5$ is an alkyl group. In certain embodiments, an amino group or an alkylamine is basic, meaning it has a conjugate acid with a $pK_a \geq 7.00$, i.e., the protonated forms of these functional groups have $pK_a$s relative to water above about 7.00.

The term "aryl" as used herein includes 3- to 12-membered substituted or unsubstituted single-ring aromatic groups in which each atom of the ring is carbon (i.e., carbocyclic aryl) or where one or more atoms are heteroatoms (i.e., heteroaryl). Preferably, aryl groups include 5- to 12-membered rings, more preferably 6- to 10-membered rings. In certain embodiments, aryl includes $(C_6$-$C_{10})$aryl. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Carbocyclic aryl groups include benzene, naphthalene, phenanthrene, phenol, aniline, and the like. Heteroaryl groups include substituted or unsubstituted aromatic 3- to 12-membered ring structures, more preferably 5- to 12-membered rings, more preferably 6- to 10-membered rings, whose ring structures include one to four heteroatoms. In certain embodiments, heteroaryl includes $(C_2$-$C_9)$heteroaryl. Heteroaryl groups include, for example, pyrrole, furan, thiophene, imidazole, oxazole, thiazole, triazole, pyrazole, pyridine, pyrazine, pyridazine and pyrimidine, and the like.

The term "aralkyl" is art-recognized and refers to an alkyl group substituted with an aryl group.

The term "heteroaralkyl" is art-recognized and refers to an alkyl group substituted with a heteroaryl group.

The term "heteroatom" is art-recognized and refers to an atom of any element other than carbon or hydrogen. Illustrative heteroatoms include boron, nitrogen, oxygen, phosphorus, sulfur and selenium.

The terms "heterocyclyl" or "heterocyclic group" refer to 3- to 12-membered ring structures, more preferably 5- to 12-membered rings, more preferably 6- to 10-membered rings, whose ring structures include one to four heteroatoms. Heterocycles can also be polycycles. In certain embodiments, heterocyclyl includes $(C_2$-$C_9)$heterocyclyl. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, —CF₃, —CN, and the like.

The term "carbonyl" is art-recognized and includes such moieties as can be represented by the formula:

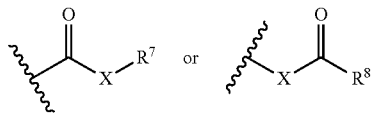

wherein X is a bond or represents an oxygen or a sulfur, and R⁷ represents a hydrogen, an alkyl, an alkenyl, —(CH₂)ₘ—R¹ or a pharmaceutically acceptable salt, R⁸ represents a hydrogen, an alkyl, an alkenyl or —(CH₂)ₘ—R¹, where m and R¹ are as defined above. Where X is an oxygen and R⁷ or R⁸ is not hydrogen, the formula represents an "ester." Where X is an oxygen, and R⁷ is as defined above, the moiety is referred to herein as a carboxyl group, and particularly when R⁷ is a hydrogen, the formula represents a "carboxylic acid". Where X is an oxygen, and R⁸ is a hydrogen, the formula represents a "formate." In general, where the oxygen atom of the above formula is replaced by a sulfur, the formula represents a "thiocarbonyl" group. Where X is a sulfur and R⁷ or R⁸ is not hydrogen, the formula represents a "thioester" group. Where X is a sulfur and R⁷ is a hydrogen, the formula represents a "thiocarboxylic acid" group. Where X is a sulfur and R⁸ is a hydrogen, the formula represents a "thioformate" group. On the other hand, where X is a bond, and R⁷ is not hydrogen, the above formula represents a "ketone" group. Where X is a bond, and R⁷ is a hydrogen, the above formula represents an "aldehyde" group.

The term "thioxamide," as used herein, refers to a moiety that can be represented by the formula:

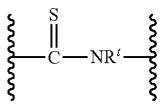

in which R' is selected from the group consisting of the group consisting of hydrogen, alkyl, cycloalkyl, aralkyl, or aryl, preferably hydrogen or alkyl. Moreover, "thioxamide-derived" compounds or "thioxamide analogues" refer to compounds in which one or more amide groups have been replaced by one or more corresponding thioxamide groups. Thioxamides are also referred to in the art as "thioamides."

The term "amido" is art recognized as an amino-substituted carbonyl and includes a moiety that may be represented by the general formula:

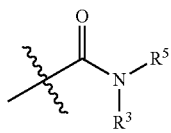

wherein R⁷ and R⁸ are as defined above. Certain embodiments of the amide in the present invention will not include imides which may be unstable.

The term "hydrazono" is art-recognized and includes such moieties as can be represented by the formula:

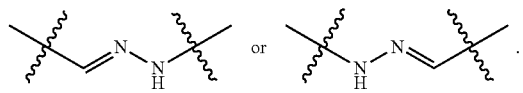 [SMILES: */C=N/N* ; */C=N/N*]

The term "maleimido" is art-recognized and includes such moieties as can be represented by the formula:

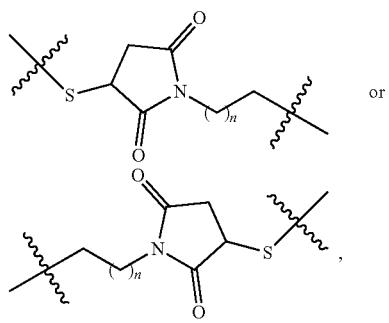

wherein n is 1 or 2.

The term "oximo" is art-recognized and includes such moieties as can be represented by the formula:

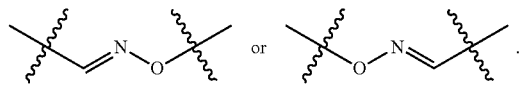 [SMILES: */C=N/O* ; */C=N/O*]

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "nitro" means —NO₂; the term "halogen" designates —F, —Cl, —Br, or —I; the term "sulfhydryl" means —SH; the term "hydroxyl" means —OH; the term "sulfonyl" means —SO₂—; the term "azido" means —N₃; the term "cyano" means —CN; the term "isocyanato" means —NCO; the term "thiocyanato"

means —SCN; the term "isothiocyanato" means —NCS; and the term "cyanato" means —OCN.

The term "haloalkyl" means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "sulfamoyl" is art-recognized and includes a moiety that can be represented by the formula:

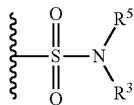

in which $R^3$ and $R^5$ are as defined above.

The term "sulfate" is art recognized and includes a moiety that can be represented by the formula:

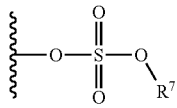

in which $R^7$ is as defined above.

The term "sulfonamide" is art recognized and includes a moiety that can be represented by the formula:

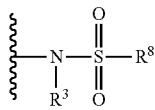

in which $R^3$ and $R^8$ are as defined above.

The term "sulfonate" is art-recognized and includes a moiety that can be represented by the formula:

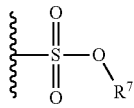

in which $R^7$ is an electron pair, hydrogen, alkyl, cycloalkyl, or aryl.

The terms "sulfoxido" or "sulfinyl", as used herein, refers to a moiety that can be represented by the formula:

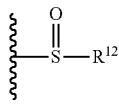

in which $R^{12}$ is selected from the group consisting of the group consisting of hydrogen, alkyl, alkenyl, alkynyl, cycloalkyl, heterocyclyl, aralkyl, or aryl.

As used herein, the definition of each expression, e.g., alkyl, m, n, etc., when it occurs more than once in any structure, is intended to be independent of its definition elsewhere in the same structure.

For purposes of this invention, the chemical elements are identified in accordance with the Periodic Table of the Elements, CAS version, *Handbook of Chemistry and Physics*, 67th ed., 1986-87, inside cover.

Pharmaceutical Compositions

Also provided are pharmaceutical compositions comprising a compound of the invention (e.g., a compound of any one of formulae I, II, IIa, III, and IV), or a pharmaceutically acceptable salt thereof, and a pharmaceutically acceptable excipient or carrier. Also provided is a method for making such pharmaceutical compositions. The method comprises placing a compound of the invention, or a pharmaceutically acceptable salt thereof, in a pharmaceutically acceptable excipient or carrier.

Compounds of the invention and pharmaceutical compositions of the invention are useful for the treatment of cancer in a subject. In certain embodiments, a therapeutically effective amount of a compound of the invention, or a pharmaceutically acceptable salt thereof, is administered to a subject in need thereof, thereby treating cancer.

As used herein, "inhibit" or "inhibiting" means reduce by an objectively measureable amount or degree compared to control. In one embodiment, inhibit or inhibiting means reduce by at least a statistically significant amount compared to control. In one embodiment, inhibit or inhibiting means reduce by at least 5 percent compared to control. In various individual embodiments, inhibit or inhibiting means reduce by at least 10, 15, 20, 25, 30, 33, 40, 50, 60, 67, 70, 75, 80, 90, or 95 percent (%) compared to control.

As used herein, the terms "treat" and "treating" refer to performing an intervention that results in (a) preventing a condition or disease from occurring in a subject that may be at risk of developing or predisposed to having the condition or disease but has not yet been diagnosed as having it; (b) inhibiting a condition or disease, e.g., slowing or arresting its development; or (c) relieving or ameliorating a condition or disease, e.g., causing regression of the condition or disease. In one embodiment the terms "treating" and "treat" refer to performing an intervention that results in (a) inhibiting a condition or disease, e.g., slowing or arresting its development; or (b) relieving or ameliorating a condition or disease, e.g., causing regression of the condition or disease.

As used herein, a "subject" refers to a living mammal. In various embodiments a subject is a non-human mammal, including, without limitation, a mouse, rat, hamster, guinea pig, rabbit, sheep, goat, cat, dog, pig, horse, cow, or non-human primate. In certain embodiments a subject is a human.

In certain embodiments, the subject is a human.

As used herein, "administering" has its usual meaning and encompasses administering by any suitable route of administration, including, without limitation, intravenous, intramuscular, intraperitoneal, intrathecal, intraocular (e.g., intravitreal), subcutaneous, direct injection (for example, into a tumor), mucosal, inhalation, oral, and topical.

In one embodiment, the administration is intravenous.

In one embodiment, the administration is oral.

As used herein, the phrase "effective amount" refers to any amount that is sufficient to achieve a desired biological effect.

Compounds of the invention can be combined with other therapeutic agents, or may be used in combination with other compounds of the invention. The compound of the invention and other therapeutic agent may be administered simultaneously or sequentially. When the other therapeutic agents are administered simultaneously, they can be administered in the same or separate formulations, but they are administered substantially at the same time. The other therapeutic agents are administered sequentially with one another and with compound of the invention, when the administration of the other therapeutic agents and the compound of the invention is temporally separated. The separation in time between the administration of these compounds may be a matter of minutes or it may be longer.

Examples of other therapeutic agents include antibiotics, anti-viral agents, anti-inflammatory agents, immunosuppressive agents, antiarrhythmic agents, beta blockers, analgesics, and anti-cancer agents.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. It is sometimes preferred that a maximum dose be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

Generally, daily oral doses of active compounds will be, for human subjects, from about 0.01 milligrams/kg per day to 1000 milligrams/kg per day. It is expected that oral doses in the range of 0.5 to 50 milligrams/kg, in one or several administrations per day, will yield the desired results. Dosage may be adjusted appropriately to achieve desired drug levels, local or systemic, depending upon the mode of administration. For example, it is expected that intravenous administration would be from one order to several orders of magnitude lower dose per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

In one embodiment, intravenous administration of a compound of the invention may typically be from 0.1 mg/kg/day to 20 mg/kg/day.

For any compound described herein the therapeutically effective amount can be initially determined from animal models. A therapeutically effective dose can also be determined from human data for compounds of the invention which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention may be administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the compound of the invention can be administered to a subject by any mode that delivers the compound of the invention to the desired location or surface. Administering the pharmaceutical composition of the present invention may be accomplished by any means known to the skilled artisan. Routes of administration include but are not limited to oral, intravenous, intramuscular, intraperitoneal, subcutaneous, direct injection (for example, into a tumor or abscess), mucosal, inhalation, and topical.

For intravenous and other parenteral routes of administration, the compound can be formulated as a lyophilized preparation with desoxycholic acid, as a lyophilized preparation of liposome-intercalated or -encapsulated active compound, as a lipid complex in aqueous suspension, or as a cholesteryl sulfate complex. Lyophilized formulations are generally reconstituted in suitable aqueous solution, e.g., in sterile water or saline, shortly prior to administration.

For oral administration, the compounds (i.e., compounds of the invention, and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of acid hydrolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, "Soluble Polymer-Enzyme Adducts", In: Enzymes as Drugs, Hocenberg and Roberts, eds., Wiley-Interscience, New York, N.Y., pp. 367-383 (1981); Newmark et al., *J Appl Biochem* 4:185-9 (1982). Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the compound of the invention (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic (e.g., powder); for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the compound of the invention (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, ca-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents which can be used and can include benzalkonium chloride and benzethonium chloride. Potential non-ionic detergents that could be included in the formulation as surfactants include lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compound of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the compounds of the invention (or derivatives thereof). The compound of the invention (or derivative) is delivered to the lungs of a mammal while inhaling and traverses across the lung epithelial lining to the blood stream. Other reports of inhaled molecules include Adjei et al., *Pharm Res* 7:565-569

(1990); Adjei et al., *Int J Pharmaceutics* 63:135-144 (1990) (leuprolide acetate); Braquet et al., *J Cardiovasc Pharmacol* 13(suppl. 5):143-146 (1989) (endothelin-1); Hubbard et al., *Annal Int Med* 3:206-212 (1989) (α1-antitrypsin); Smith et al., 1989, *J Clin Invest* 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, *J Immunol* 140:3482-3488 (interferon-gamma and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong, et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of compound of the invention (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compound of the invention may also be prepared in different formulations depending on the type of chemical modification or the type of device employed.

Formulations suitable for use with a nebulizer, either jet or ultrasonic, will typically comprise compound of the invention (or derivative) dissolved in water at a concentration of about 0.1 to 25 mg of biologically active compound of the invention per mL of solution. The formulation may also include a buffer and a simple sugar (e.g., for compound of the invention stabilization and regulation of osmotic pressure). The nebulizer formulation may also contain a surfactant, to reduce or prevent surface induced aggregation of the compound of the invention caused by atomization of the solution in forming the aerosol.

Formulations for use with a metered-dose inhaler device will generally comprise a finely divided powder containing the compound of the invention (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing compound of the invention (or derivative) and may also include a bulking agent, such as lactose, sorbitol, sucrose, or mannitol in amounts which facilitate dispersal of the powder from the device, e.g., 50 to 90% by weight of the formulation. The compound of the invention (or derivative) should advantageously be prepared in particulate form with an average particle size of less than 10 micrometers (μm), most preferably 0.5 to 5 m, for most effective delivery to the deep lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described above, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer R, Science 249:1527-33 (1990), which is incorporated herein by reference.

The compounds of the invention and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

Pharmaceutical compositions of the invention contain an effective amount of a compound of the invention and optionally therapeutic agents included in a pharmaceutically acceptable carrier. The term "pharmaceutically acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to the compound of the invention, may be provided in particles. Particles as used herein means nanoparticles or microparticles (or in some instances larger particles) which can consist in whole or in part of the compound of the invention or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero-order release, first-order release, second-order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the compound of the invention in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described in Sawhney H S et al. (1993) *Macromolecules* 26:581-7, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof.

EXAMPLES

Having now described the present invention in detail, the same will be more clearly understood by reference to the following examples, which are included herewith for purposes of illustration only and are not intended to be limiting of the invention.

Materials.

Chemicals were purchased and used as received unless otherwise specified. Anhydrous dimethylformamide (DMF) was dried with a column packed with 4 Å molecular sieves. Tetrahydrofuran (THF) were dried with a column packed with alumina. Dox-VC-NH$_2$[16], Pt—COOH[17] were synthesized according literature report. DBCO-TEG-NHS, DBCO-TEG-NH$_2$, sµLfo-DBCO-TEG-NH$_2$, DBCO-NH$_2$ were purchased from Click Chemistry Tools. MAL-PEG$_{5k}$-SCM, Py-SS-PEG$_{5k}$-CONHS were purchased from Laysan Bio Inc. HPLC grade 0.1% TFA-H$_2$O and acetonitrile were purchased from Fisher Scientific Company LLC (Hanover Park, Ill., USA). All other chemicals were purchased from Sigma-Aldrich (St. Louis, Mo., USA).

Instrumentation.

HPLC analysis was conducted by Shimadzu LC system (LC-20AT) connected with PDA detector (SPD-M20A). Phenomenex Kinetex Ph-hexyl column (5 µm, 100 mm×4.6 mm) was used for analysis. Gradient method was used with 0.1% TFA-H$_2$O and acetonitrile (ACN) as mobile phase.

Example 1. Synthesis of Ac$_4$GalNAz Derivatives

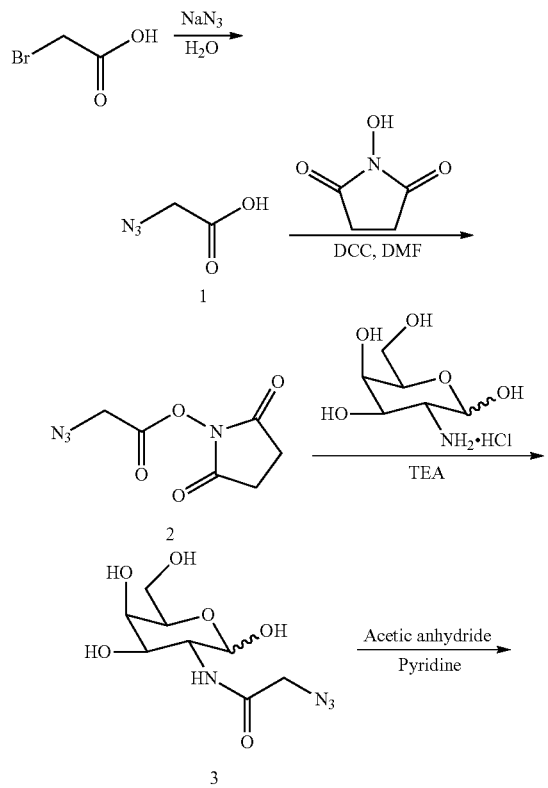

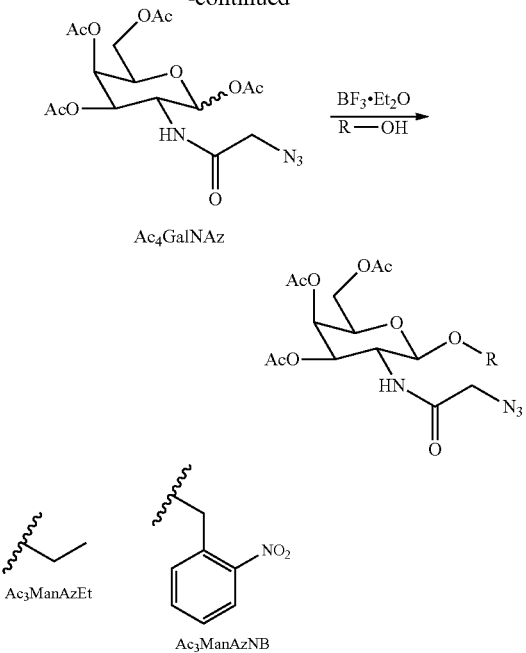

Synthesis of 2-Azidoacetic Acid (1)

Bromoacetic acid (2.78 g, 20 mmol) was dissolved in DI water (30 mL), followed by the addition of sodium azide (2.60 g, 40 mmol). The mixture was stirred at room temperature for 24 h. The resulting solution was adjusted to pH=1 using hydrogen chloride solution, and then extracted with diethyl ether for three times (100 mL×3). The organic phase was collected, dried over anhydrous sodium sulfate, and concentrated to get colorless oil (80% yield, 1.62 g).

Synthesis of N-(2-azidoacetyl) Succinimide (2)

N,N'-Dicyclohexylcarbodiimide (DCC, 2.06 g, 10 mmol) and 1 (1.01 g, 10 mmol) were dissolved in anhydrous DMF, followed by the addition of N-hydroxysuccinimide (1.15 g, 10 mmol). The mixture was stirred at room temperature for 24 h. After removal of the precipitate, the solvent was removed to yield a yellow solid. The crude product was recrystallized from dichloromethane/hexane to obtain a white solid (70% yield, 1.39 g). $^1$H NMR (CDCl$_3$, 500 µMHz): δ 4.25 (s, 2H, N$_3$CH$_2$), 2.88 (s, 4H, CH$_2$CH$_2$). $^{13}$C NMR (CDCl$_3$, 500 µMHz): 168.7, 164.4, 48.2, 25.8. LRMS (ESI) m/z: calculated for C$_6$H$_7$N$_4$O$_4$[M+H]$^+$ 199.0, found 199.0.

Synthesis of Ac$_4$GalNAz (AAG)

D-Galactosamine hydrochloride (539 mg, 2.5 mmol) and triethylamine (253 mg, 2.5 mmol) were dissolved in methanol (40 mL), followed by the addition of 2 (545 mg, 2.75 mmol). The mixture was stirred at room temperature for 24 h. Solvent was removed under reduced pressure and the residue was redissolved in pyridine. Acetic anhydride (10 mL) was added and the reaction mixture was stirred at room temperature for another 24 h. After removal of the solvent, the crude product was purified by silica gel column chromatography using ethyl acetate/hexane (1/1, v/v) as the eluent to yield a white solid (45% yield, 484.5 mg). LRMS (ESI) m/z: calculated for $C_{16}H_{22}N_4O_{10}Na$ [M+Na]$^+$453.1, found 453.1.

Synthesis of Ac$_3$GalNAzEt (AAG-Et)

Ac$_4$GalNAz (43 mg, 0.1 mmol) and anhydrous ethanol (14 mg, 0.3 mmol) were dissolved in dry DCM (1.5 mL) and purged with nitrogen for 10 min. Boron trifluoride etherate (71 mg, 0.5 mmol) was added through a syringe. The mixture was stirred in the dark overnight at room temperature. DCM (30 mL) was then added and the solution was washed with saturated sodium bicarbonate solution twice (10 mL×2) and DI water twice (10 mL×2), respectively. The organic phase was collected, dried over anhydrous sodium sulfate, and concentrated to yield yellow oil. The crude product was purified by silica gel column chromatography using ethyl acetate/hexane (1/1, v/v) as the eluent to yield a white solid (30% yield, 12.5 mg). LRMS (ESI) m/z: calculated for $C_{16}H_{25}N_4O_9$ [M+H]$^+$ 417.2, found 417.2.

Synthesis of Ac$_3$GalNAzNb (AAG-Nb)

Ac$_4$GalNAz (43 mg, 0.1 mmol) and 2-nitrobenzylalcohol (30 mg, 0.2 mmol) were dissolved in dry DCM (1.5 mL) and purged with nitrogen for 10 min. Borontrifluoride etherate (70.9 mg, 0.5 mmol) was added through a syringe. The mixture was stirred overnight at room temperature under nitrogen atmosphere. DCM (30 mL) was then added and the solution was washed with saturated sodium bicarbonate solution twice (10 mL×2) and DI water twice (10 mL×2), respectively. The organic phase was collected, dried over anhydrous sodium sulfate and concentrated to yield brown oil. The crude product was purified by silica gel column chromatography using ethyl acetate/hexane (1/1, v/v) as the eluent to yield a pale red solid (25% yield, 13.0 mg). LRMS (ESI) m/z: calculated for $C_{21}H_{25}N_5O_{11}Na$ [M+Na]$^+$546.2, found 546.2.

Example 2. Investigation of Ac$_4$GalNAz Derivatives in Cell-Labeling

Figure 2:
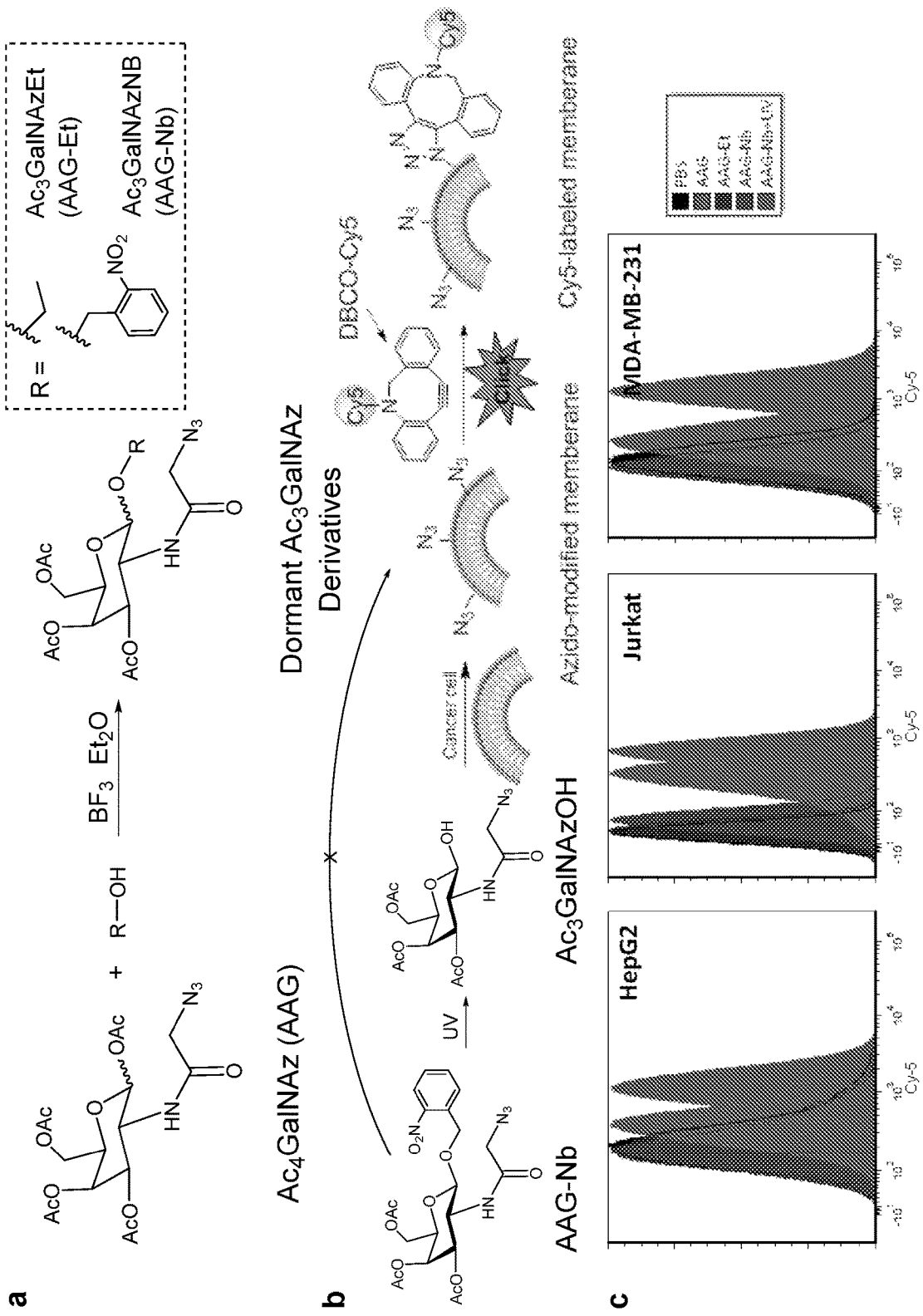
FIG. 2 consists of panels a-c. Panel (a) shows the synthetic route of Ac$_3$GalNAz (AAG) derivatives including Ac$_3$GalNAzEt (AAG-Et) and Ac$_3$GalNAzNb (AAG-Nb). Panel (b) is a scheme depicting the UV irradiation-activated metabolic labeling of AAG-Nb and subsequent detection of azido groups by DBCO-Cy5 via copper-free Click chemistry. Panel (c) contains graphs depicting flow cytometry analysis of HepG2 (liver cancer), Jurkat (lymphoma) and MDA-MB-231 (breast cancer) cells for different groups: PBS, AAG (50 μM), AAG-Et (50 μM), AAG-Nb (50 μM), and AAG-Nb (50 μM)+UV.

To demonstrate whether modifying the C1 site of Ac$_4$GalNAz (AAG) by forming a glycosidic (ether) bond could block the metabolic labeling process, 1-O-ethyl-3,4,6-triacetyl-N-azidoacetylgalactosamine (Ac$_3$GalNAzEt, AAG-Et) with an ether bond blocking C1 position was prepared (FIG. 2, panel a). The labeling efficiencies of AAG derivatives in HepG2 (liver cancer), Jurkat (lymphoma) and MDA-MB-231 (triple negative breast cancer) cells were evaluated. These cells were incubated with Ac$_4$GalNAz (AAG), Ac$_3$GalNAzEt (AAG-Et), and PBS respectively for three days. The azido-sugar content on cell surface membrane was detected by DBCO-Cy5 (25 µM for 50 min) via Click reaction and analyzed by flow cytometry (FIG. 2, panel c). As shown in FIG. 2, panel c, AAG can efficiently label all of the three cell lines within 72 hours. The successful expression of azido groups was indicated by strong Cy5 fluorescence on the cell surface. AAG-Et showed negligible labeling as compared with negative PBS (phosphate buffered saline) control. That is, the AAG-Et treatment showed negligible Cy5 fluorescence on the cell surface. These data demonstrated that AAG-Et failed to metabolically label cancer cells with azido groups.

To further demonstrate that the glycosidic bond at the C1 site was responsible for the blocking of the metabolic labeling process, and that cleavage of this bond to expose 1-OH could reactivate the labeling process, 1-(2-nitrobenzyl)-3,4,6-triacetyl-N-azidoacetylgalactosamine (Ac$_3$GalNAzNb, AAG-Nb) with an ultraviolet (UV)-cleavable 2-nitrobenzyl group at C1 position was synthesized (FIG. 2, panel b). HepG2 (liver cancer), Jurkat (lymphoma) and MDA-MB-231 (triple negative breast cancer) cells were incubated with AAG-Nb for three days, and cell-surface azido groups were detected by DBCO-Cy5 (25 µM for 50 min). Without UV irradiation, these cells treated with AAG-Nb showed negligible Cy5 fluorescence on cell surface, further demonstrating the blocking effect of chemical modification at C1 site (FIG. 2, panel c). In contrast, UV treatment (15 min, 10 mW/cm$^2$) that can cleave the 2-nitrobenzyl group of AAG-Nb and release triacetyl-N-acetylgalactosamine (FIG. 2, panel b) significantly increased cell labeling of the sugar and showed significantly enhanced Cy5 fluorescence. The results clearly demonstrate that the anomeric (1'-position) modification of N-acetylgalactosamine with an ether bond can efficiently block its metabolization in various cancer cells.

Figure 3:
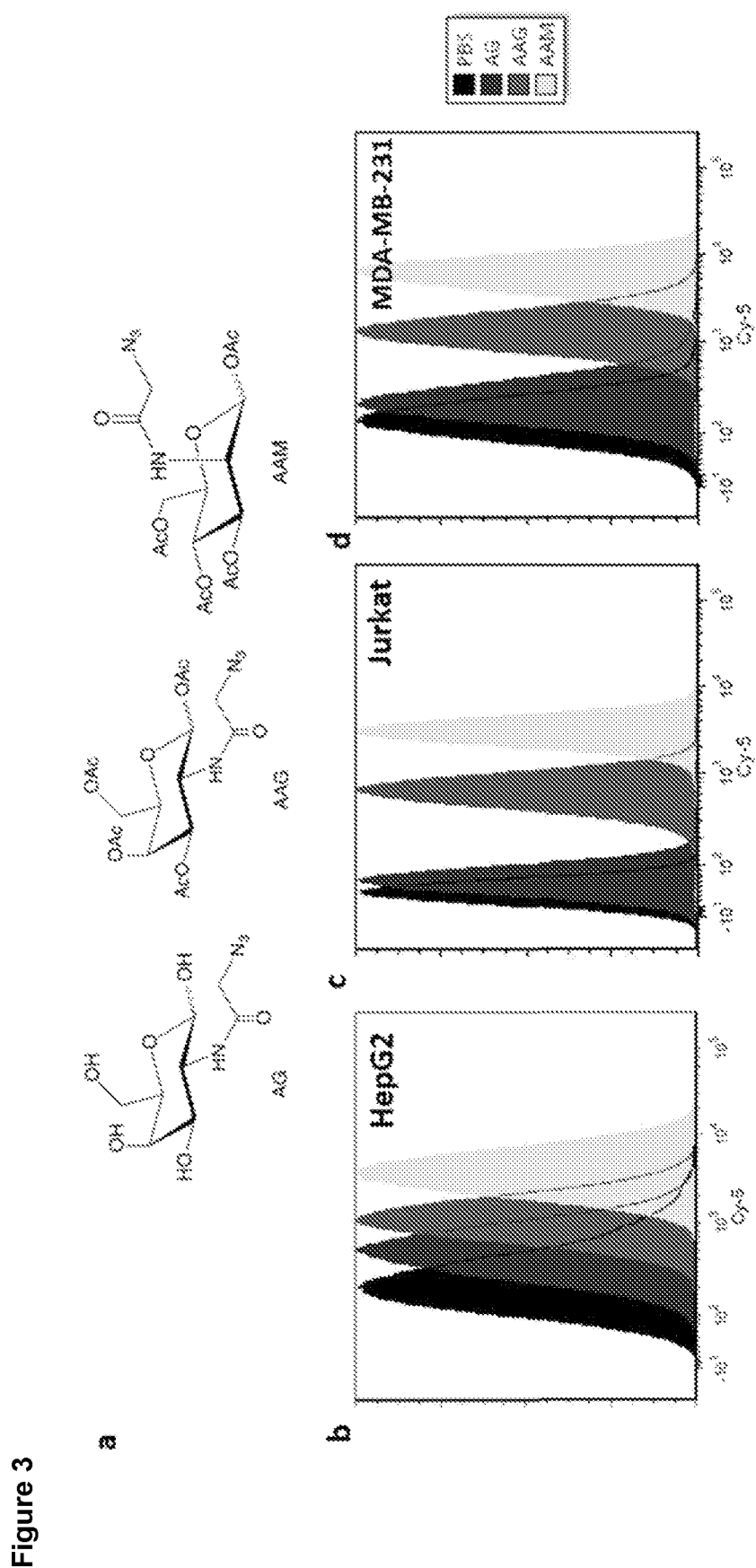
FIG. 3 consists of panels a and b. Panel (a) shows the structures of unnatural sugar used in the cell labeling experiments. Panel (b) contains graphs depicting flow cytometry analysis of HepG2 (liver cancer), Jurkat (lymphoma) and MDA-MB-231 (breast cancer) cells for different groups: PBS, AG (50 μM), AAG (50 μM), and AAM (50 μM).

It is known that galactosamine can be preferentially taken up by hepatocytes (a type of liver cells) due to the presence of cell receptors such as asialoglycoprotein receptor (ASGPR). Tetraacetyl-N-azidoacetylgalactosamine (AAG) is relative hydrophobic and can passively diffuse into cells through hydrophobic interactions with the lipid cell membrane while N-azidoacetylgalactosamine (AG) is too hydrophilic to penetrate the lipid barrier by passive diffusion. Therefore, AG can only be taken up by cells through receptor-mediated endocytosis. The AG labeling in HepG2 (hepatocellular carcinoma) cells was tested and compared with other extra-hepatic cell lines, including Jurkat and MDA-MB-231 (FIG. 3, panel b). While AAG and tetraacetyl-N-azidoacetylmannosamine (AAM) efficiently labeled all of the three cell lines, only HepG2 cells were positively labeled by AG. The results demonstrate that N-acetylgalactosamine (AG) can selectively label cancer cells from liver origin while tetraacetyl-N-acetylgalactosamine (AAG) does not have selectivity over different cancer cells.

Figure 4:
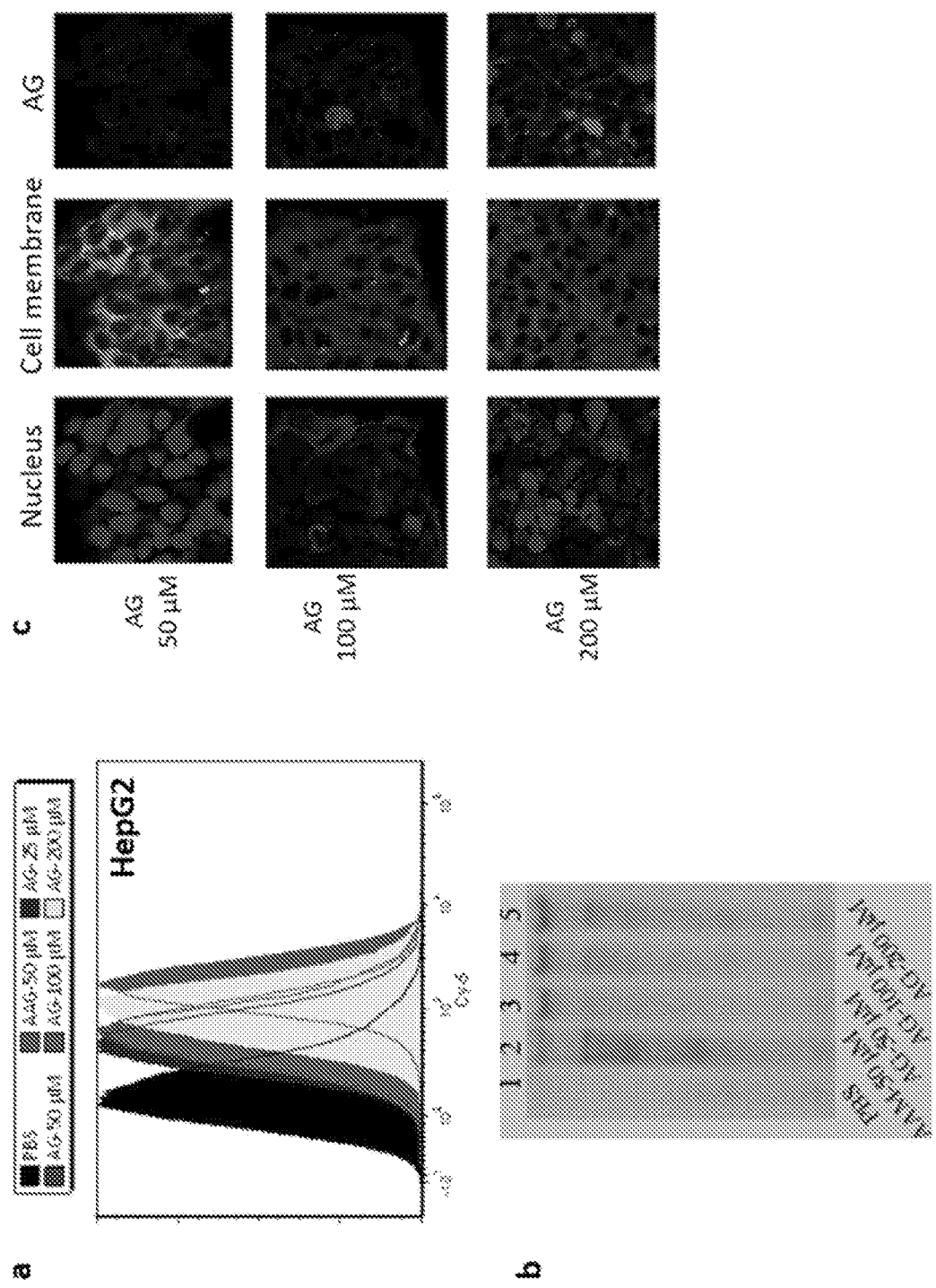
FIG. 4 consists of three panels. Panel (a) contains graphs depicting flow cytometry analysis of HepG2 (liver cancer) cells for different groups: PBS, AAG (50 μM), AG (25 μM), AG (50 μM), AG (100 μM) and AG (200 μM). Panel (b) shows cell membrane glycoproteins containing azides as analyzed by SDS-PAGE. Panel (c) shows confocal laser scanning microscope images of HepG2 liver cancer cells with AG labeling. The cell nuclei were stained with Hoechst (blue) and cell membrane was stained with cell mask orange (orange). AG was stained with DBCO-Cy5 (red).
Figure 5:
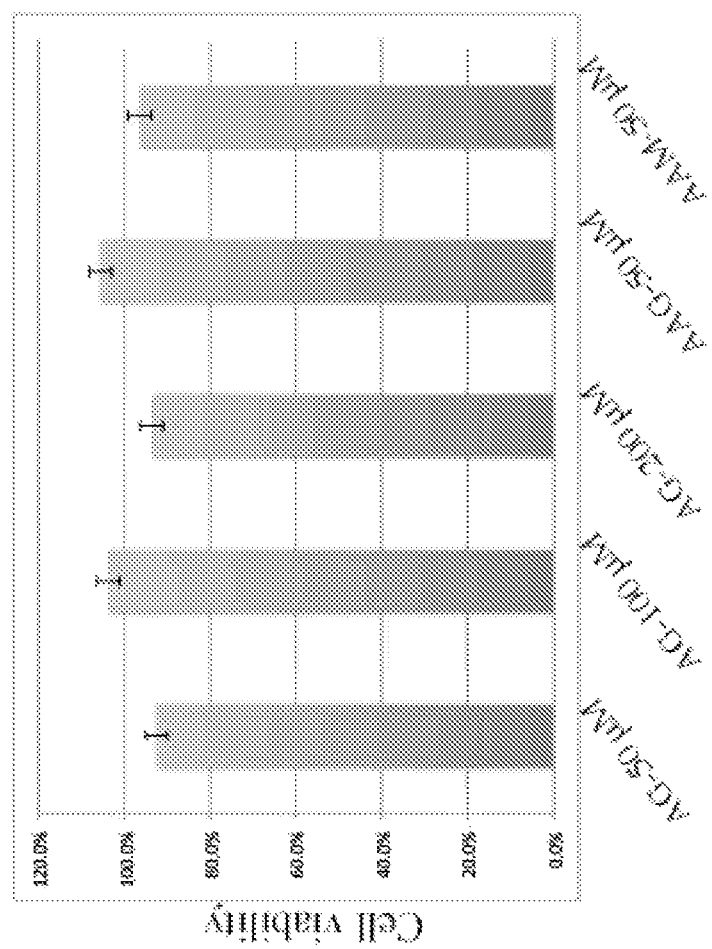
FIG. 5 shows the cytotoxicity of AG (50 μM), AG (100 μM), AAG (50 μM), and AAM (50 μM) analyzed by MTT assay in HepG2 hepatocarinoma cells.

The AG labeling in HepG2 cells was further characterized by various techniques. The AG labeling on HepG2 cells was shown to be concentration dependent. The AG labeling in HepG2 cells increased significantly as the concentration of AG increased from 25 µM to 200 µM (FIG. 4, panel a). The SDS-PAGE further confirmed that the cell surface membrane protein did containing azide groups, and the fluorescence signal came from the azido-sugar labeled glycoproteins instead of non-specific adsorption (FIG. 4, panel b). Confocal microscopy showed that the AG labeling mainly localized on cell membrane (FIG. 4, panel c). An MTT assay showed that AG is not toxic to HepG2 cells at up to 200 µM concentration indicating the AG can be a safe reagent for targeted cell labeling (FIG. 5).

General Procedures for Flow Cytometry Analysis of Azido-Sugar Labeled Cells.

Cells were seeded onto coverslips in a 6-well plate at a cell density of 40 k/well. AAG or AAG derivatives were added and incubated with cells for 72 h. After removal of medium and multiple washing steps, DBCO-Cy5 (25 µM) in opti-MEM was added and incubated with cells at 37° C. for 1 h. The opti-MEM was then removed and cells were washed with PBS three times. Cells were lifted by incubating with trypsin solution (100 µL) at 37° C. for 5 min and transferred to test tubes with addition of 4% PFA solution (0.4 mL). Ten thousand cells per sample were analyzed by flow cytometry and data analysis was performed on the FCS Express software.

AAG-Nb Mediated Controlled Cell Labeling.

HepG2 (liver cancer), Jurkat (lymphoma) or MDA-MB-231 (triple negative breast cancer) cells were seeded onto coverslips in a 6-well plate at a cell density of 40 k/well. AAG-Nb with a final concentration of 50 µM was added. UV light (10 mW/m$^2$) was applied for 15 min at the start of incubation, and the cells were further incubated for 72 h. Cells without UV irradiation were continuously incubated for 72 h. Cell samples for flow cytometry were then prepared following the above-mentioned procedures.

General Procedures for Confocal Imaging of Azido-Sugar Labeled Cells.

Cells were seeded onto coverslips in a 6-well plate at a cell density of 40 k/well. Ac$_4$GalNAz (AAG) or AAG derivatives were added with a final concentration of 50 µM and the cells were incubated at 37° C. for 72 h. The medium was removed and washed with PBS for three times. DBCO-Cy5 (25 µM) in Opti-MEM was then added and the cells were incubated for another 1 h. Then the medium was removed, and the cells were washed with PBS three times. 4% paraformaldehyde (PFA) solution was added to fix the cells for 10 min, followed by staining of cell nucleus with Hoechst (1 µg/mL) and staining of cell membrane with cell mask orange (5 ug/mL) for 10 min. The coverslips were mounted on microscope slides with the addition of ProLong Gold antifade reagent, and the prepared sample was stored in dark for imaging.

SDS-PAGE Analysis of Cells Treated with Azido-Sugars.

HepG2 liver cancer cells were seeded onto 6-well plate at a cell density of 40 k/well. Different azido-sugars at different concentrations were added and incubated with cells for 72 h. After removal of medium and multiple washing steps, DBCO-Cy5 (25 µM) in opti-MEM was added and incubated with cells at 37° C. for 1 h. The opti-MEM was then removed and cells were washed with PBS three times. The cells were homogenized in 150 µL of lysis buffer (RIPA) containing protease inhibitor. The lysate was incubated at 4° C. for 30 min, followed by centrifugation at 5000 rcf for 5 min to remove insoluble debris. The total concentration of soluble protein in each sample was determined by bicinchoninic acid (BCA) assay and adjusted to the same concentration. 4× loading buffer was added to each sample and 15 µL samples containing 20 µg protein were loaded onto 10% SDS-PAGE gel after heating at 95° C. The gel was run for 60 min under 150 V. Cy-5 fluorescence was imaged by Imagequant LAS 4010 Luminescent image analyzer and the gel was further stained by coomassie blue MTT Cell Viability Assay.

HepG2 liver cancer cells were seeded onto coverslips in a 6-well plate at a cell density of 40 k/well. Different azido-sugars (AG, AAG, and AAM) at different concentrations (50 µM-200 µM) were added, and the cells were incubated at 37° C. for 72 h. The medium was removed. Then 20 µL 3-(4,5-dimethyl-2-thiazolyl)-2,5-diphenyl-2H-tetrazolium bromide (MTT) (5 mg/mL in PBS) was added and cultured at 37° C. for 4 h. MTT is a substrate that provides a colorimetric signal in response to viable mitochondria. Following solubilization by 100 µl DMSO, absorbance at 570 nm was measured using a plate reader.

Example 3. Investigation of Alternative Self-Immolative Linkers

Figure 6:
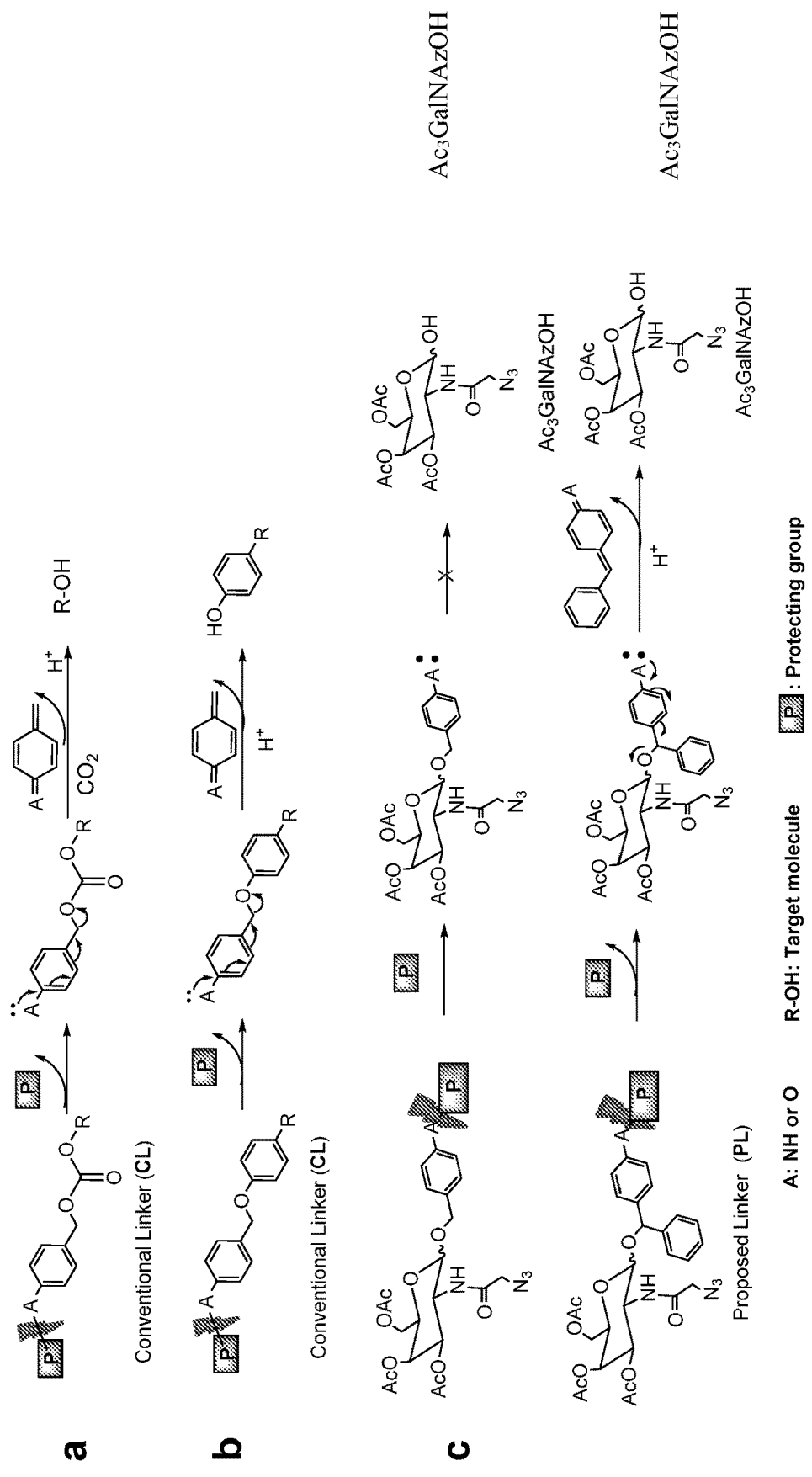
FIG. 6 consists of three panels. Panel (a) depicts schemes showing the use of two conventional self-immolative linkers (CL1 and CL2) used in conventional prodrug systems. Panel (b) shows a first proposed linker PL1 derived from CL2. Panel (c) shows a second proposed linker (PL2) modified from PL1. The additional phenyl ring stabilizes the cleaved product, thus facilitating the degradation process.

After demonstrating the controlled labeling strategy, the aim was to apply it to in vivo cancer labeling and targeting. Since UV is not a practical trigger in vivo because of its poor tissue penetration and potential damage to healthy tissues, development of Ac$_3$GalNAz derivatives that are responsive to internal cancer-specific triggers such as redox dysregulation, elevated oxidant level, and overexpressed enzymes was important. However, different from UV irradiation which can directly cleave a 2-nitrobenzyl glycosidic bond into hydroxyl group, these triggers are not able to directly cleave the glycosidic bond, thus requiring the incorporation of a self-immolative linker that can eventually release the hydroxyl group after trigger-induced cleavage of the protecting group. Two conventional self-immolative linkers, CL1 and CL2, have been widely used in prodrug design (FIG. 6, panel a). Upon removal of the protecting group, CL1 can rapidly get rid of a CO$_2$ molecule to expose the hydroxyl group. However, CL1 contains a carbonate bond which can be easily degraded by cellular esterase, and thus is not available for this design. CL2 can rapidly release the phenol structure as a good leaving group upon removal of the protecting group. Considering that the sugar compound with unmasked 1-OH might be a good leaving group, we designed PL1 (FIG. 6, panel b) with a similar structure to CL2 and incorporate it into hydrogen peroxide (H$_2$O$_2$)-responsive Ac$_3$GalNAzHB. However, Ac$_3$GalNAzHB failed to release Ac$_3$ManAzOH even though the protecting group was easily removed by H$_2$O$_2$. PL2 was designed with an additional phenyl group linked to the α-carbon of PL1 based on the assumption that the greatly stabilized degradation product would facilitate the cleavage of the self-immolative linker (FIG. 6, panel c).

Example 4. Synthesis of DBCO-TEG-VC-DOX

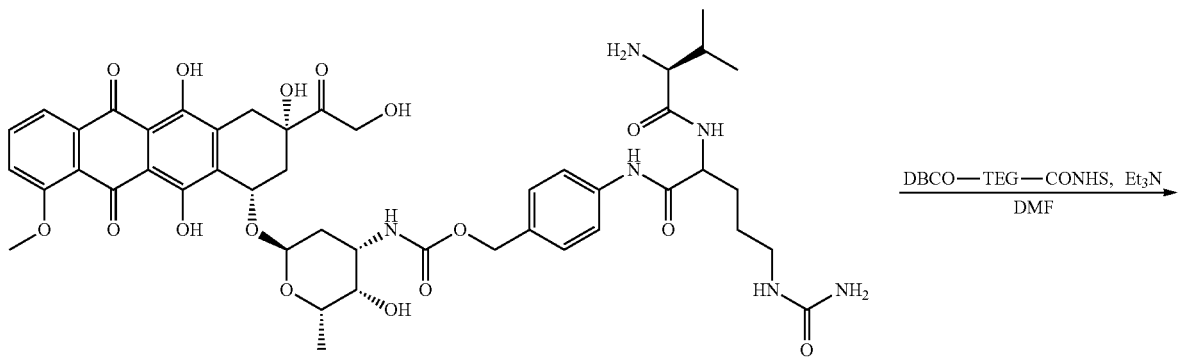

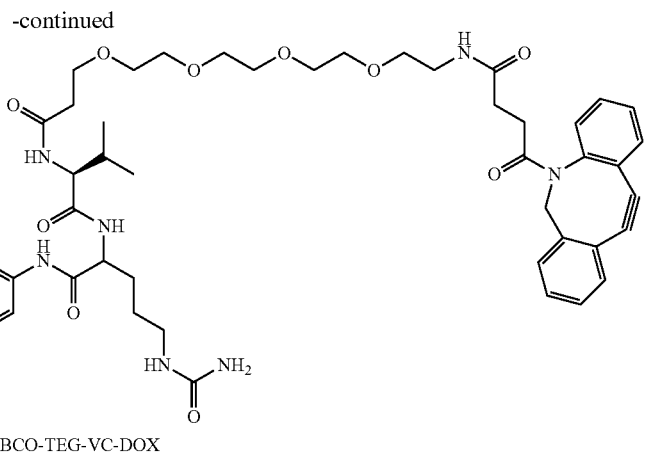
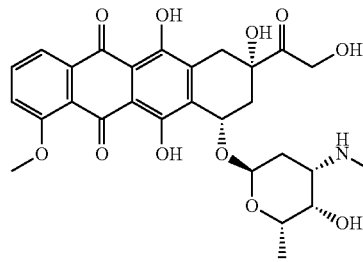

DBCO-TEG-VC-DOX

Dox-VC-NH$_2$ (58 mg, 1.0 equiv.), DBCO-TEG-NHS (38 mg, 1.0 equiv.), and trimethylamine (9.8 μL, 1.2 eq) was mixed in anhydrous DMF (1 mL) and stirred at room temperature. The reaction was monitored by HPLC and was completed within 6 hrs. 8 μL trifluoroacetic acid was added to quench the reaction and the mixture was subject to silica column directly (DCM:MeOH 5:1) giving a red powder as the product (68 mg, yield 75%). ESI-MS: calcd for C$_{76}$H$_{91}$N$_8$O$_{23}$$^+$: 1483.6, found: 1483.5.

Example 5. Synthesis of Sulfo-DBCO-TEG-VC-DOX

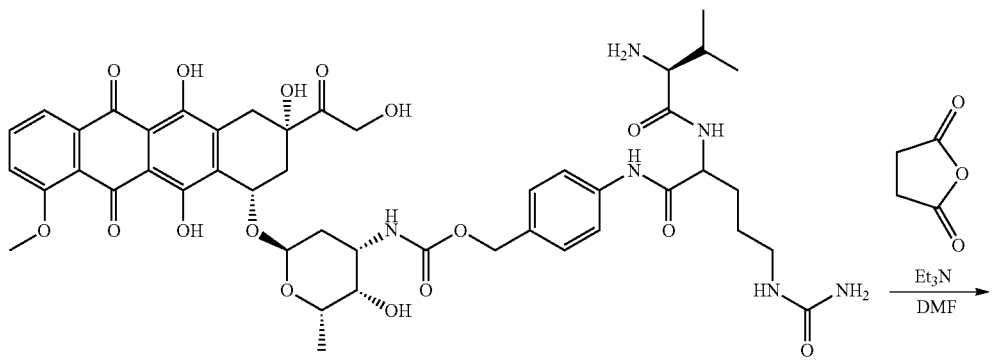

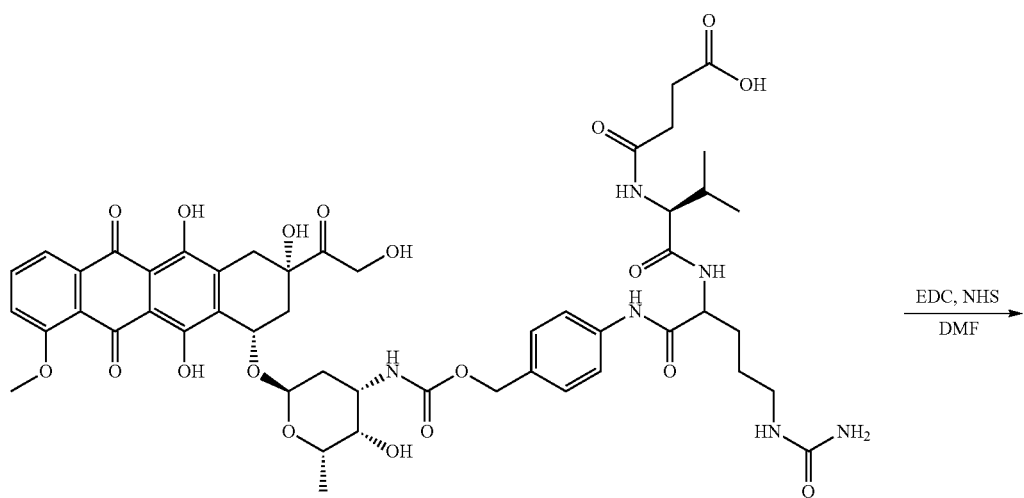

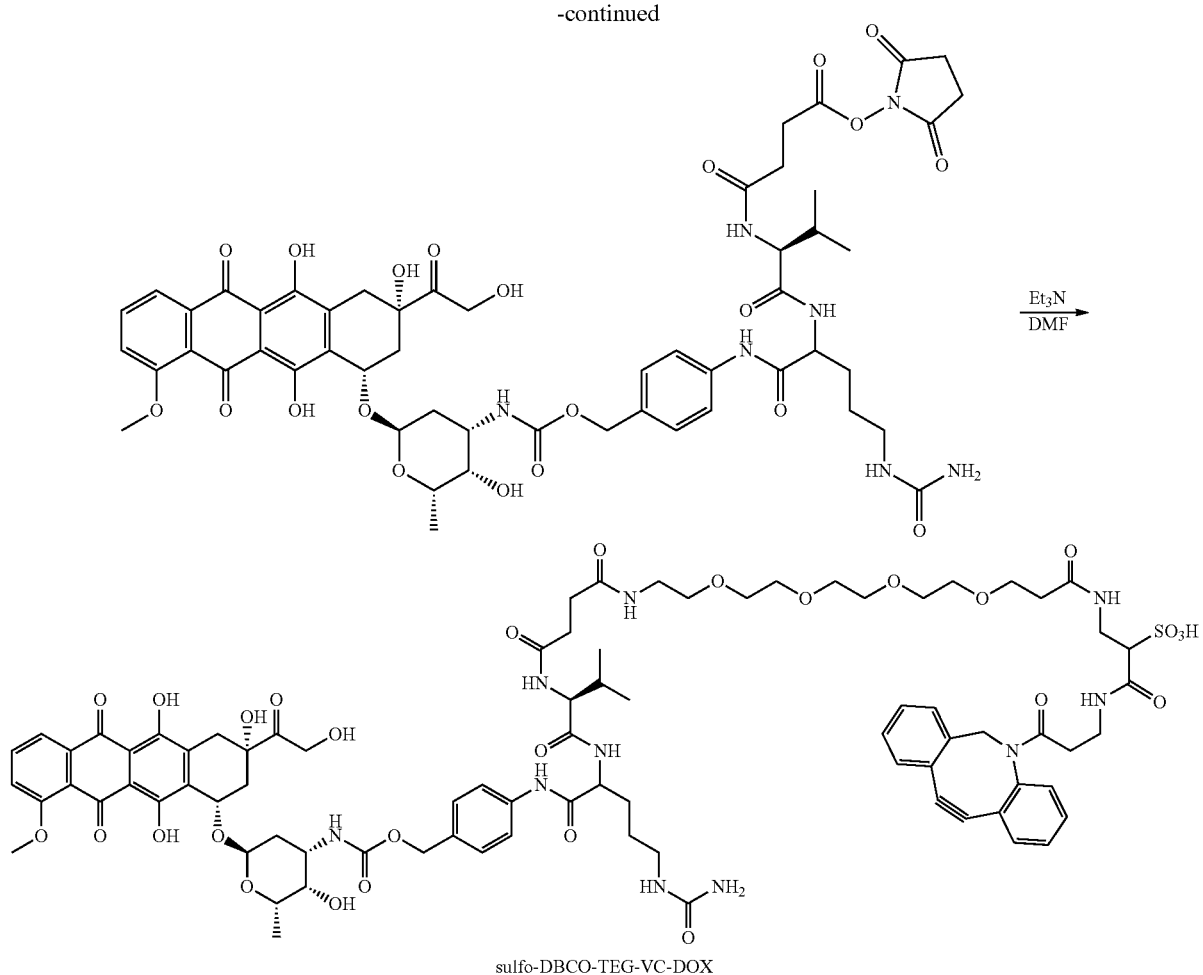

sulfo-DBCO-TEG-VC-DOX

Dox-VC-NH$_2$ (51 mg, 0.054 mmol, 1.0 equiv.), succinic anhydride (5.9 mg, 0.059 mmol, 1.1 equiv.), and trimethylamine (9.0 µL, 0.065 mmol, 1.2 equiv.) was mixed in anhydrous DMF (1 mL) at room temperature and stirred overnight. N-(3-Dimethylaminopropyl)-N'-ethylcarbodiimide hydrochloride (15.5 mg, 0.081 mmol, 1.5 equiv.) and N-hydroxysuccinimide (9.3 mg, 0.081 mmol, 1.5 equiv.) was then added and the reaction was stirred at room temperature overnight. The solution was precipitated in 13 mL 0.1 M HCl (aq) and the precipitate was collected by centrifuge. The solid was washed with 15 mL 0.1 M HCl (aq) twice and 15 mL H$_2$O once, dried as pure Dox-VC-CONHS (41 mg, 0.036 mmol). After the Dox-VC-CONHS was mixed with suLfo-DBCO-NH$_2$ (29 mg, 0.043 mmol, 1.2 equiv.) in DMF (800 µL), trimethylamine (6 µL, 0.043 mmol, 1.0 equiv.) was added. The solution turned dark purple and the reaction was stirred overnight.

The clear solution was then precipitated in 10 mL isopropanol and the precipitate was collected by centrifuge. The solid was redissolved in DMF (600 µL) and precipitated in i-propanol twice giving a red powder after lyophilization in H$_2$O (40 mg, yield 66%). ESI-HRMS: calcd for C$_{82}$H$_{101}$N$_{10}$O$_{28}$S$^+$1705.6507, found: 1705.6470.

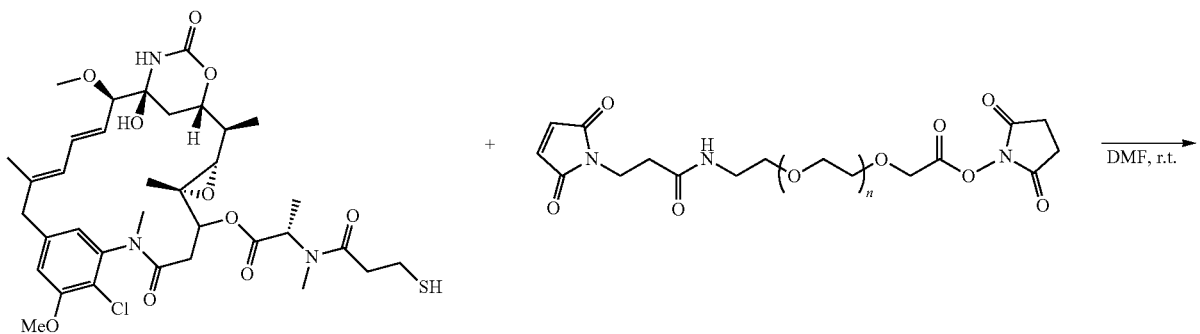

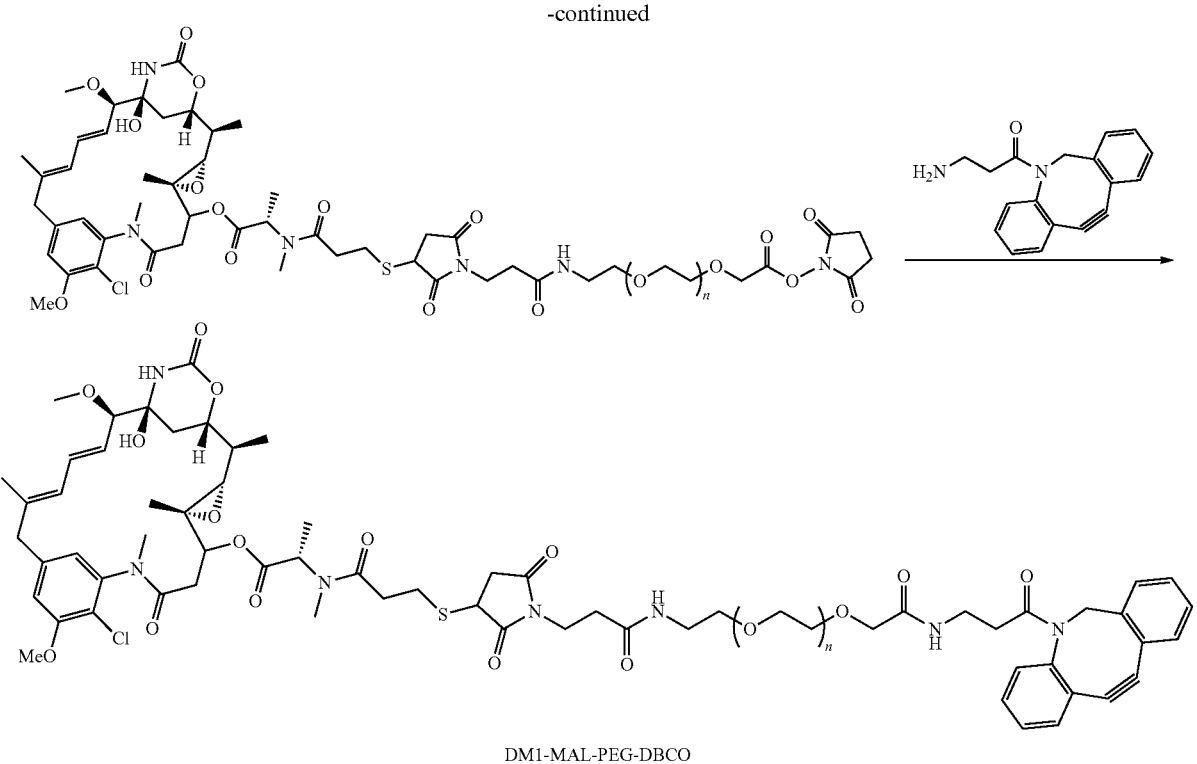

DM1-MAL-PEG-DBCO

Example 6. Synthesis of DM1-MAL-PEG-DBCO

MAL-PEG$_{5k}$-SCM (119 mg, 0.024 mmol, 1.0 equiv.) was dissolved in anhydrous DMF upon heating to 40° C. The solution was cooled to room temperature and DM-1 (18 mg, 0.025 mmol, 1.05 equiv.) was then added. After the completion of the reaction in 4 hr, DBCO-NH$_2$ (7 mg, 0.025 mmol, 1.05 equiv.) was added and the solution was stirred at r.t. overnight. The mixture was then subject to RP-HPLC (Ph-hex phase) purification using acetonitrile (ACN)/H$_2$O-TFA (25%-75% ACN gradient method) giving an off-white powder as the product (53 mg, yield 32%).

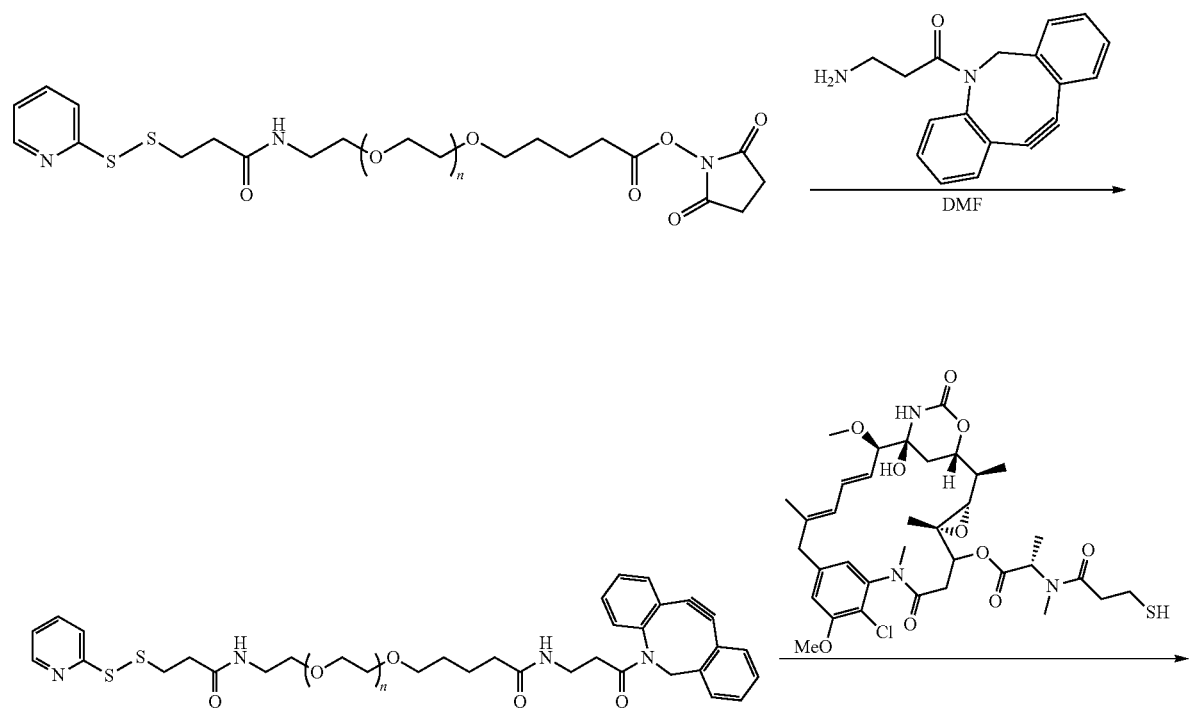

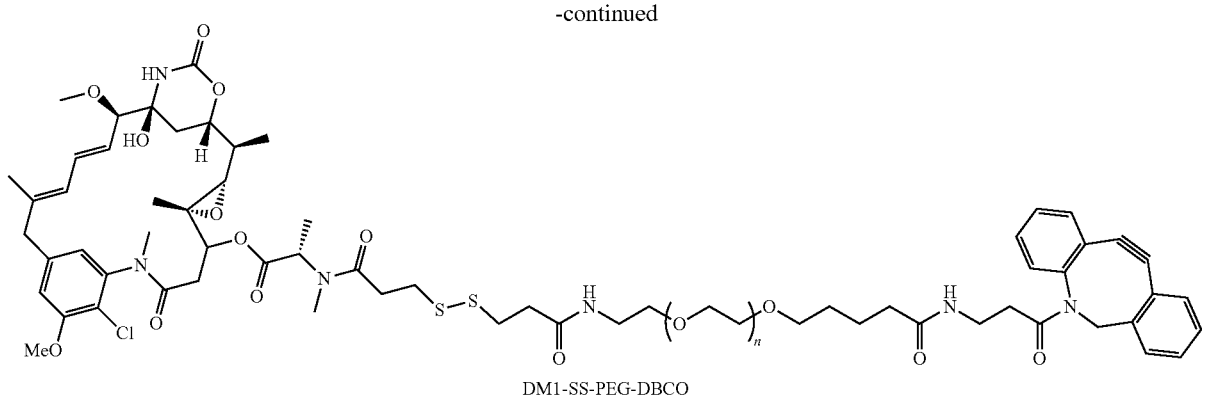

DM1-SS-PEG-DBCO

Example 7. Synthesis of DM1-MAL-PEG-DBCO

Py-SS-PEG$_{5k}$-CONHS (196 mg, 0.40 mmol, 1.0 equiv.) and DBCO-NH$_2$ (11.6 mg, 0.42 mmol, 1.05 equiv.) were mixed in anhydrous DMF (1 mL) for 30 minutes. The solution was then mixed with DM1 (29.5 mg, 0.040 mmol, 1.0 equiv.) in 400 µL DMF. The solution was stirred for 15 minutes and the reaction was shown to be complete by HPLC. The mixture was then subject to RP-HPLC (Ph-hex phase) purification using acetonitrile (ACN)/H$_2$O-TFA (25%-75% ACN gradient method) giving an off-white powder as the product (113 mg, yield 50%).

DMSO (300 µL). Pt—COOH gradually dissolved in 1 hr and a DMSO solution of DBCO-NH$_2$ (14.5 mg, 0.053 mmol, 1.05 equiv.) was added and the reaction was stirred overnight. The reaction mixture was then diluted with 0.1% TFA-H$_2$O and subject to RP-HPLC (Ph-hex phase) purification using acetonitrile (ACN)/H$_2$O-TFA (25%-75% ACN gradient method) giving an light yellow powder as the product (9 mg, yield 26%). ESI-HRMS: calcd for C$_{22}$H$_{26}$C$_{12}$N$_4$O$_5$Pt+: 691.0928, found: 691.0917.

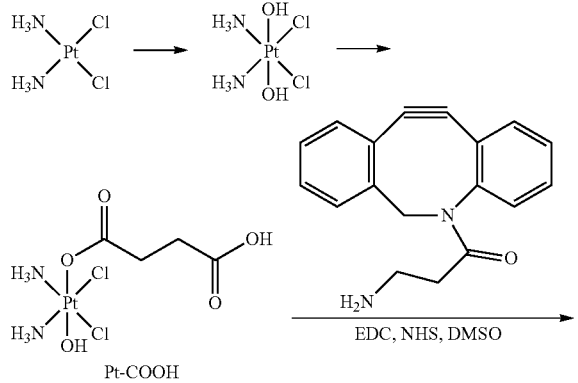

Pt-COOH → Pt-DBCO

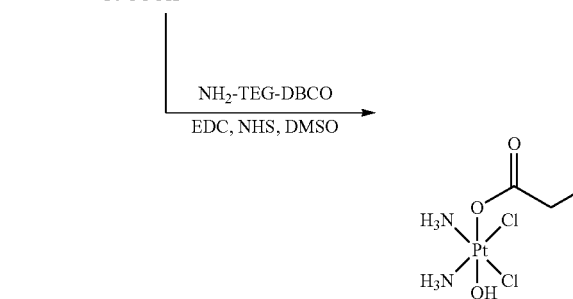

Pt-TEG-DBCO

Example 8. Synthesis of Pt-DBCO

Pt—COOH (21.5 mg, 0.05 mmol, 1.0 equiv.), N-(3-Dimethylaminopropyl)-N'-ethylcarbodiimide hydrochloride (8.5 mg, 0.055 mmol, 1.1 equiv.) and N-hydroxysuccinimide (6.5 mg, 0.055 mmol, 1.1 equiv.) were mixed in anhydrous

Example 9. Synthesis of Pt-TEG-DBCO

Pt—COOH (87 mg, 0.2 mmol, 1.0 equiv.), N-(3-Dimethylaminopropyl)-N'-ethylcarbodiimide hydrochloride (37 mg, 0.24 mmol, 1.2 equiv.) and N-hydroxysuccinimide (28 mg, 0.24 mmol, 1.2 equiv.) were mixed in anhydrous DMSO (2 mL). Pt—COOH gradually dissolved in 1 hr and the solution was stirred for another 4 hr. A DMSO solution (1 mL) of DBCO-TEG-NH$_2$ (115 mg, 0.22 mmol, 1.1 equiv.) was added and the reaction was completed in 10 minutes as being monitored by HPLC. The reaction mixture was then diluted with 0.1% TFA-H$_2$O and subject to RP-HPLC (Ph-hex phase) purification using acetonitrile (ACN)/H$_2$O-TFA (25%-75% ACN gradient method) giving an off-white powder as the product (92 mg, yield 49%). ESI-HRMS: calcd for C$_{33}$H$_{48}$Cl$_2$N$_5$O$_{10}$Pt$^+$ calculated: 939.2426, found: 939.2419.

ent method) giving an off-white powder as the product (131 mg, yield 38%). ESI-HRMS: calcd for C$_{79}$H$_{90}$N$_3$O$_{22}$$^+$: 1432.6010. Found: 1432.6003.

Example 11. DBCO-Doxorubicin Conjugates

MTT Assay to Evaluate In Vitro Cytotoxicity.

Standard MTT protocol was followed to evaluate the cytotoxicity of DBCO-drug conjugate. Briefly, MDA-MB-231 cells were seeded in 96-well plate at 3000 cells/well in

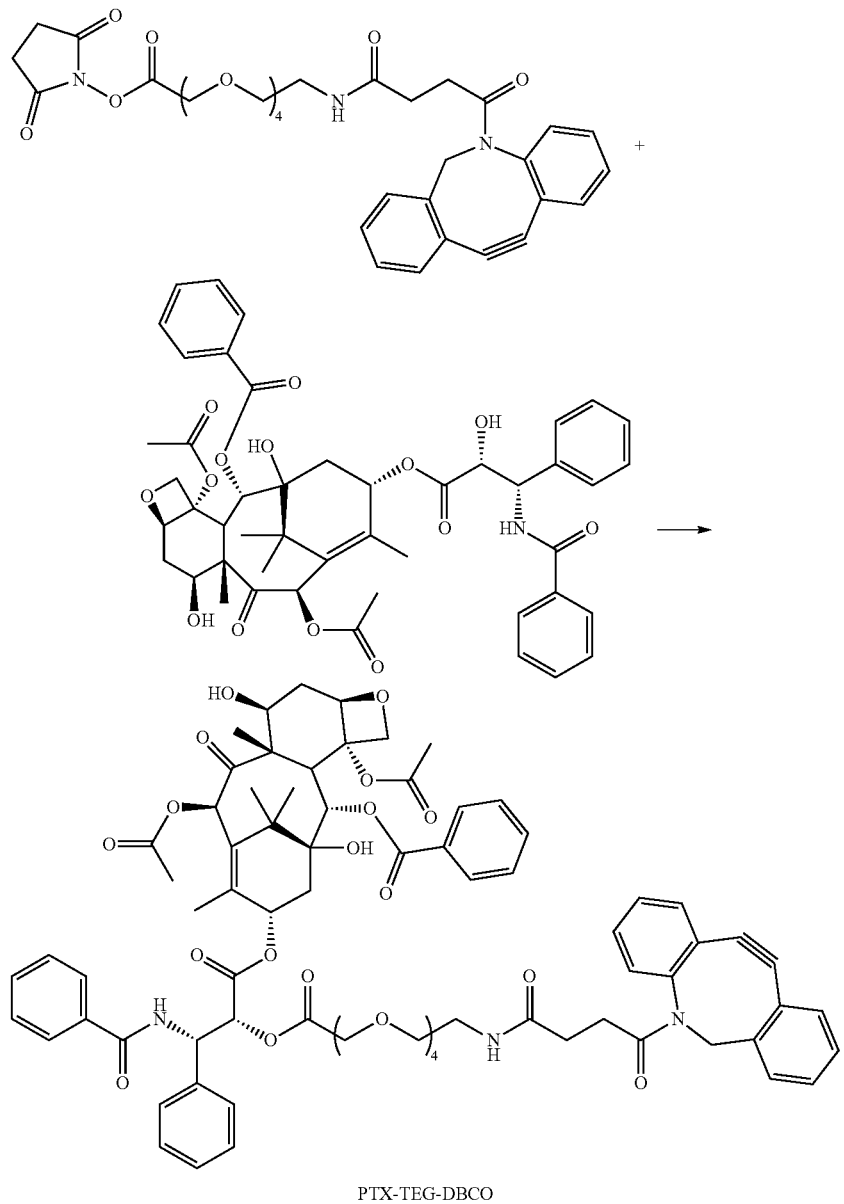

PTX-TEG-DBCO

Example 10. Synthesis of PTX-TEG-DBCO

DBCO-TEG-NHS (162 mg, 0.25 mmol, 1.0 equiv.), paclitaxel (213 mg, 0.25 mmol, 1.0 equiv.), N,N-dimethylaminopyridine (30 mg, 0.25 mmol, 1.0 equiv.) were mixed in methylene chloride and stirred at r.t. overnight. The mixture was then subject to RP-HPLC (Ph-hex phase) purification using acetonitrile (ACN)/H$_2$O-TFA (25%-75% ACN gradi- 100 µL DMEM medium and were allowed to attach overnight. 10 µL DBCO-drug conjugate solution was added into the well to the designated final concentration and incubated at 37° C. for 72 hours. PBS was taken as 100% control. 20 µL 5 mg/mL MTT solution was added to the medium and incubated at 37° C. for 3 hours. Then the medium was carefully removed and the violet crystal was dissolved in 100 µL DMSO and quantified by absorption at $\lambda_{abs}$=570 nm.

Figure 7:
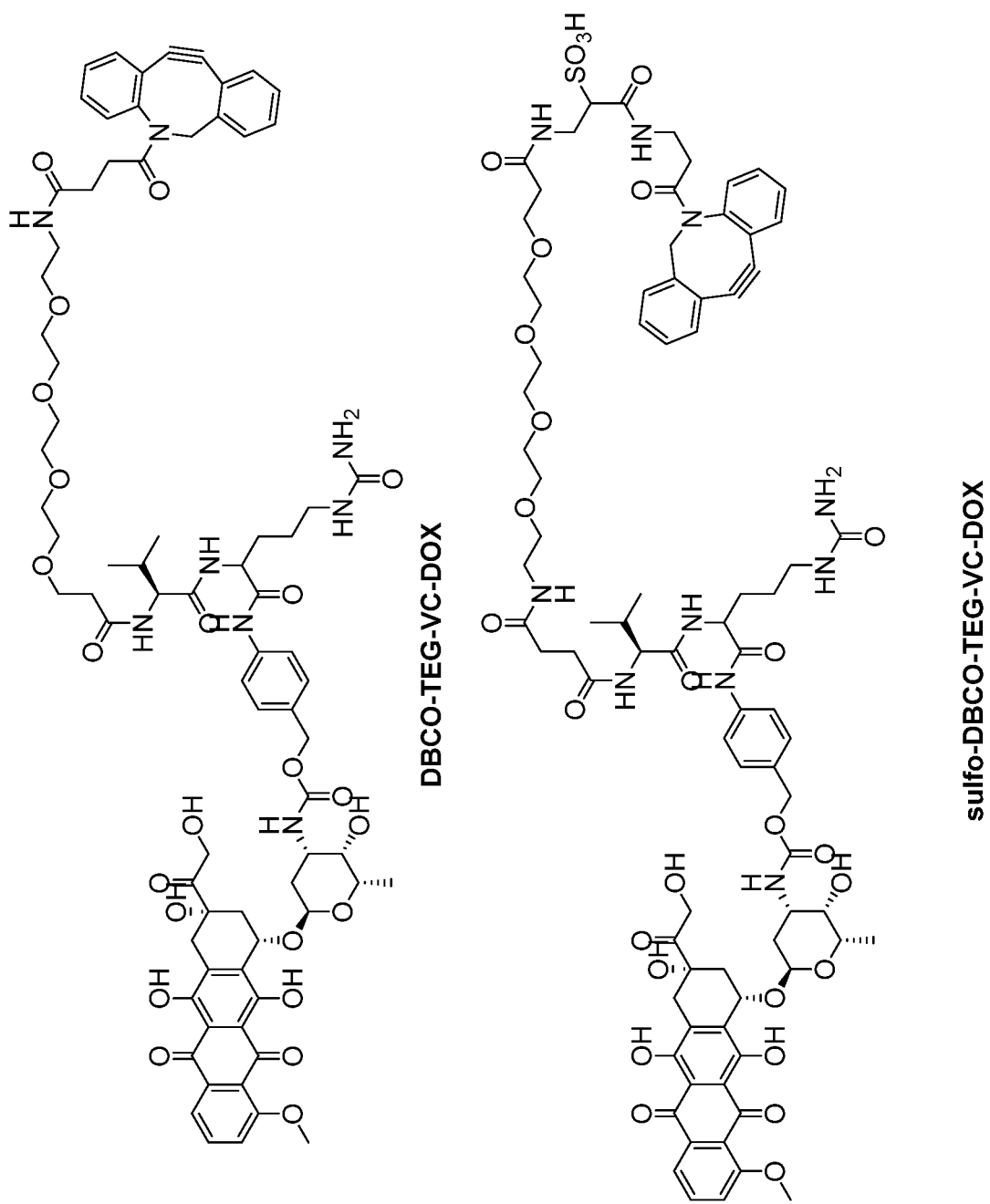
FIG. 7 shows the chemical structures of DBCO-TEG-VC-DOX and sulfo-DBCO-TEG-VC-DOX.
Figure 8:
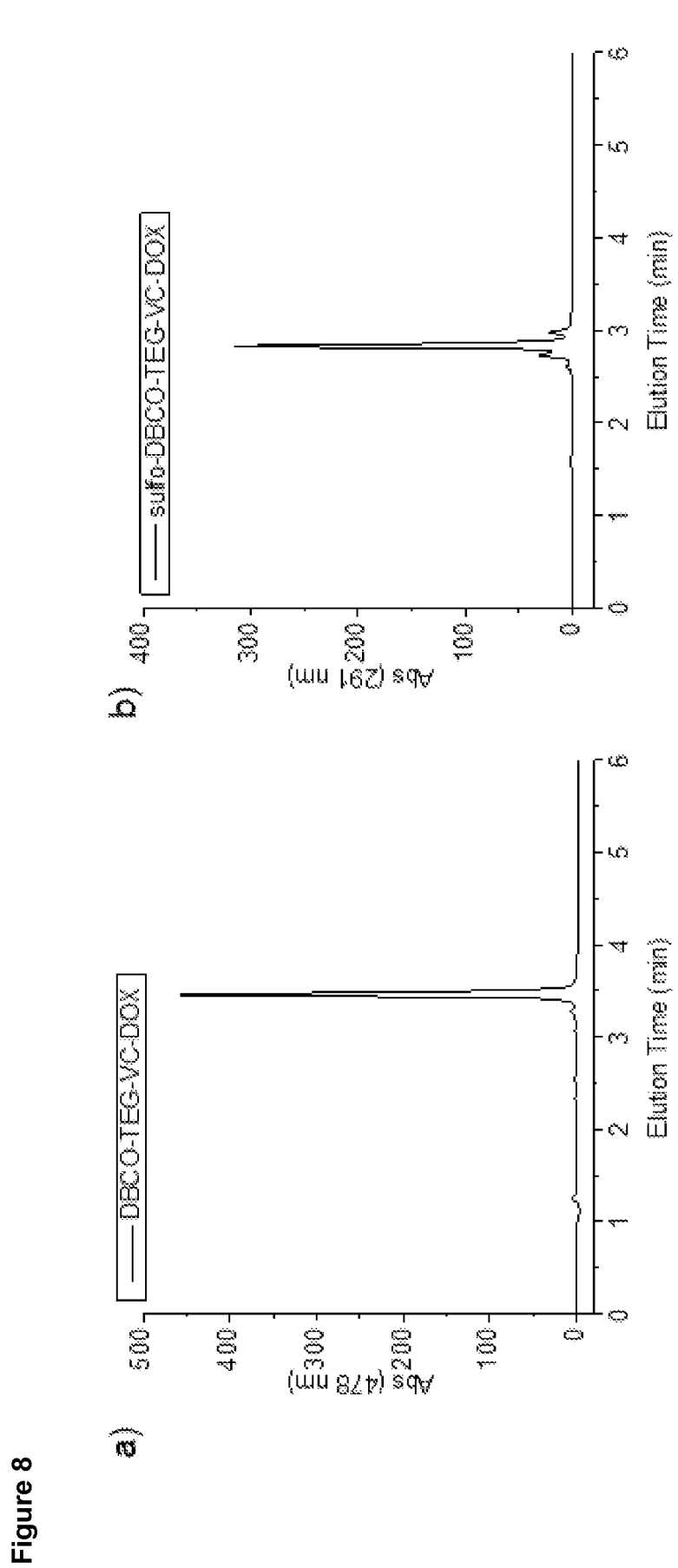
FIG. 8 consists of two panels showing HPLC traces of DBCO-TEG-VC-DOX (panel a) and sulfo-DBCO-TEG-VC-DOX (panel b); ($\lambda_{abs}$=478 nm).

Two DBCO-doxorubicin conjugates were synthesized with a cathepsin-B responsive peptide linker (VC). A tetraethyleneglycol unit was incorporated to improve the solubility of the conjugates (FIG. 7). A sulfonic acid-containing conjugate, sulfo-DBCO-TEG-VC-DOX was also prepared to further improve the solubility of the conjugate. The purity and identity of the conjugates were verified by reverse phase high performance liquid chromatography (RP-HPLC) (FIG. 8) and mass spectra. The solubility of the two conjugates were first tested. It was found that the sulfo-DBCO-TEG-VC-DOX can be readily dissolved in phosphate buffered saline (PBS) up to 8-10 mg/mL. In contrast, the DBCO-TEG-VC-DOX has a solubility lower than 50 µM in PBS and ~3.5 mg/mL in DMSO-tween 80-PBS (5-10-85) formulation.

Figure 9:
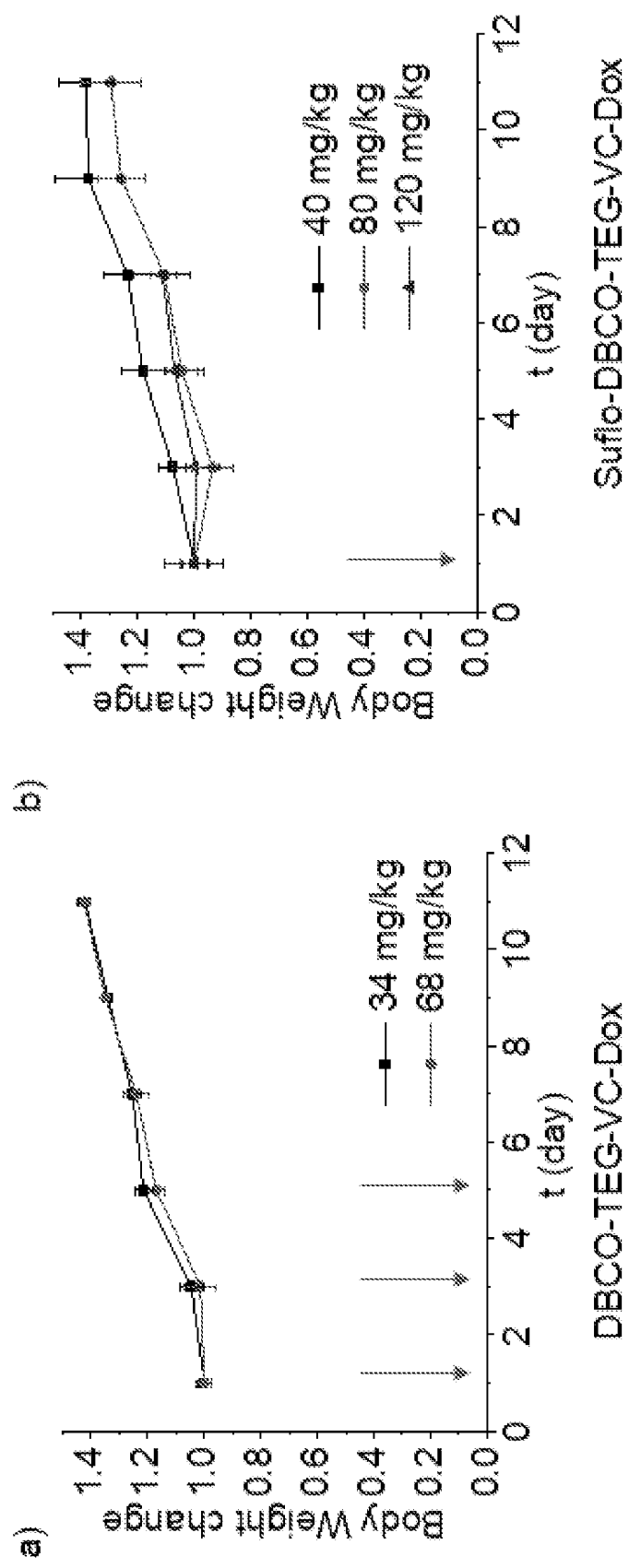
FIG. 9 consists of two panels showing body weight growth curves of CD-1 mice after i.v. injection(s) of DBCO-TEX-VC-Dox (panel a) and sulfo-DBCO-TEX-VC-Dox (panel b) at various dosages. Time of injections are marked with arrows.

The maximum tolerable dose (MTD) of the two conjugates were also evaluated in CD-1 mice (FIG. 9). The MTD of free doxorubicin (dox or DOX) was tested to be 20 mg/kg (<20% body weight loss) on a single injection. DBCO-TEG-VC-DOX was injected using the DMSO-tween 80-PBS (5-10-85) formulation on day 1, 3, and 5 with a dose of 34, 68 mg/kg (37.5, 75 mg/kg equivalent cumulative dox dose respectively). No significant body weight loss was observed in CD-1 mice suggesting an MTD above 204 mg/kg. The sulfo-DBCO-TEG-VC-DOX was injected using PBS with only one time administration. No body weight decrease was observed under the maximal feasible dose used in the study suggesting an MTD higher than 120 mg/kg (37.5 mg/kg equivalent Dox dose).

Example 12. DBCO-Mertansine (DM1) Conjugates

Figure 10:
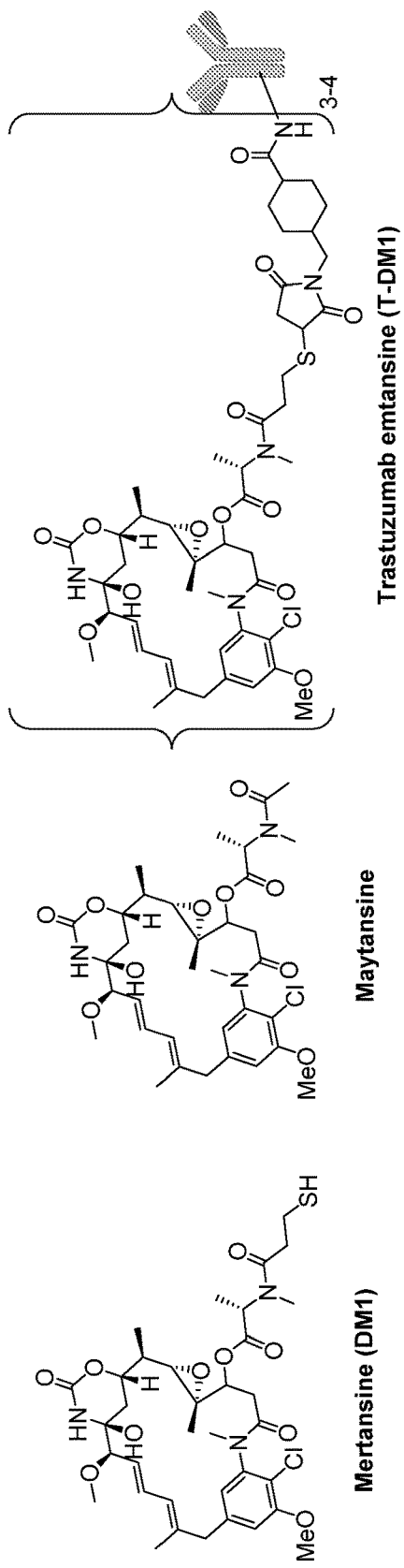
FIG. 10 shows the chemical structures of mertansine (DM1), maytansine, and trastuzumab emtansine (T-DM1).

Mertansine (DM1, FIG. 10) is a potent inhibitor of tubulin polymerization and is an extremely effective cytotoxic reagent with in vitro $IC_{50}$ value down to tens of pM in a variety of breast cancer cell lines.[12] The parental drug of DM1, maytansine (FIG. 10), has been extensively evaluated in Phase I and II clinical trials for cancer treatment, but was discontinued due to the severe toxicity and inefficient therapeutic index.[13] Recently, DM1 has been used as the cytotoxic reagent in antibody-drug conjugate and achieved tremendous success in Her2+ breast cancer treatment with the drug, T-DM1 (trastuzumab emtansine, trade name Kadcyla®, FIG. 10). The combination of trastuzumab's (Her2 antibody) targeting capability and DM1's cytotoxic killing effect makes T-DM1 an effective therapeutic drug for Her2-overexpressed breast cancers with minimal side effects. In analogy to T-DM1, it was proposed to combine the targeting capability of the ATTACK labeling with the cytotoxic killing of DBCO-DM1 conjugate as the first targeted small molecular mertansine drug for anti-cancer treatment.

Figure 11:
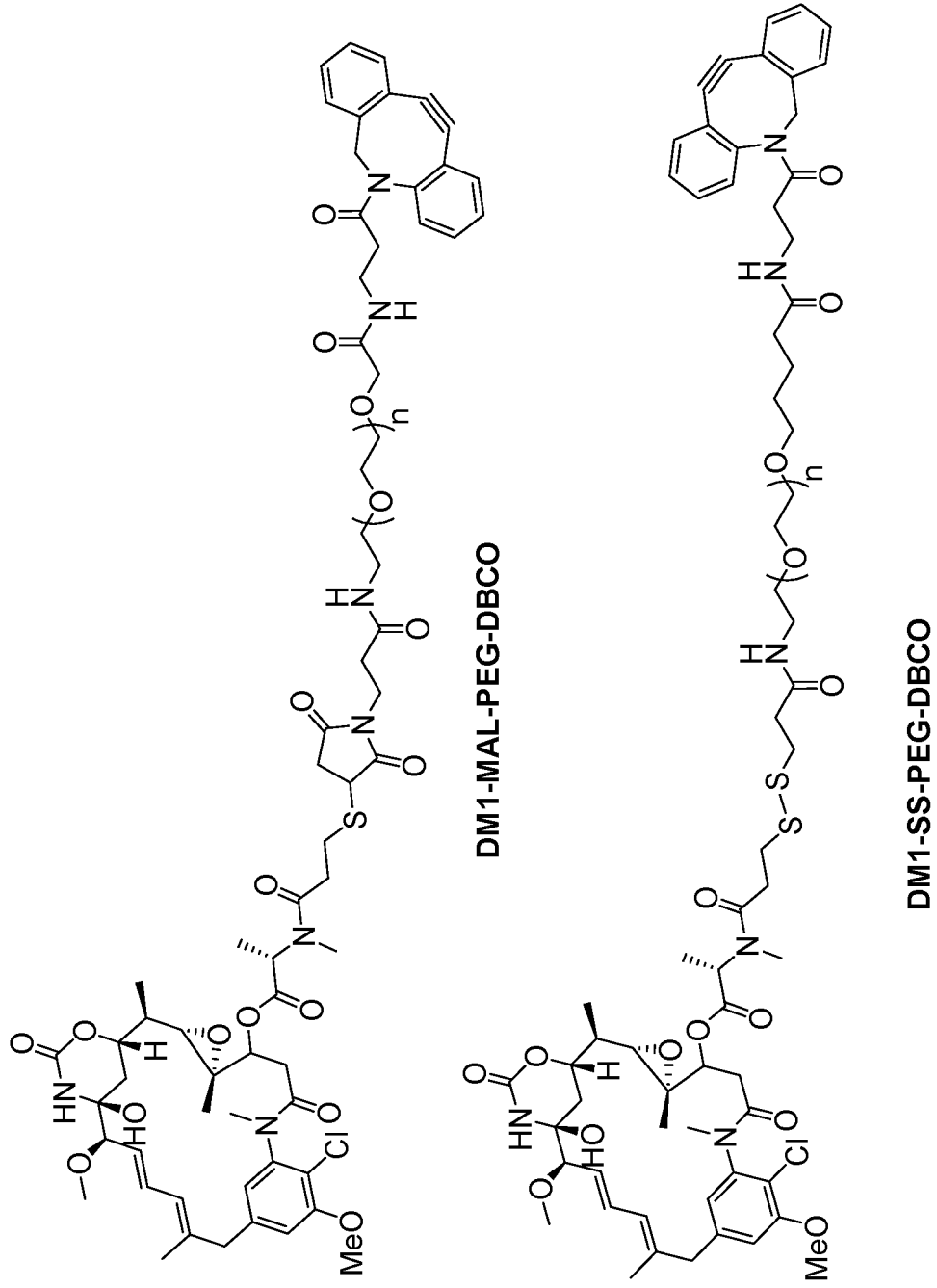
FIG. 11 shows the chemical structures of DM1-MAL-PEG-DBCO and DM1-SS-PEG-DBCO.
Figure 12:
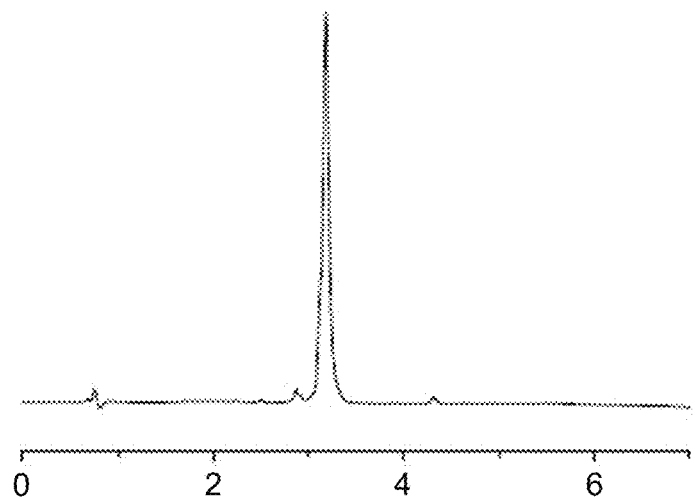
FIG. 12 consists of two panels showing: (panel a) HPLC trace of DM1-MAL-PEG-DBCO. ($\lambda_{abs}$=285 nm); and (panel b) MALDI-TOF of DM1-MAL-PEG-DBCO. Matrix: trans-2-[3-(4-tert-Butylphenyl)-2-methyl-2-propenylidene] malononitrile (DCTB). Major peaks are [P+Na]+.
Figure 12:
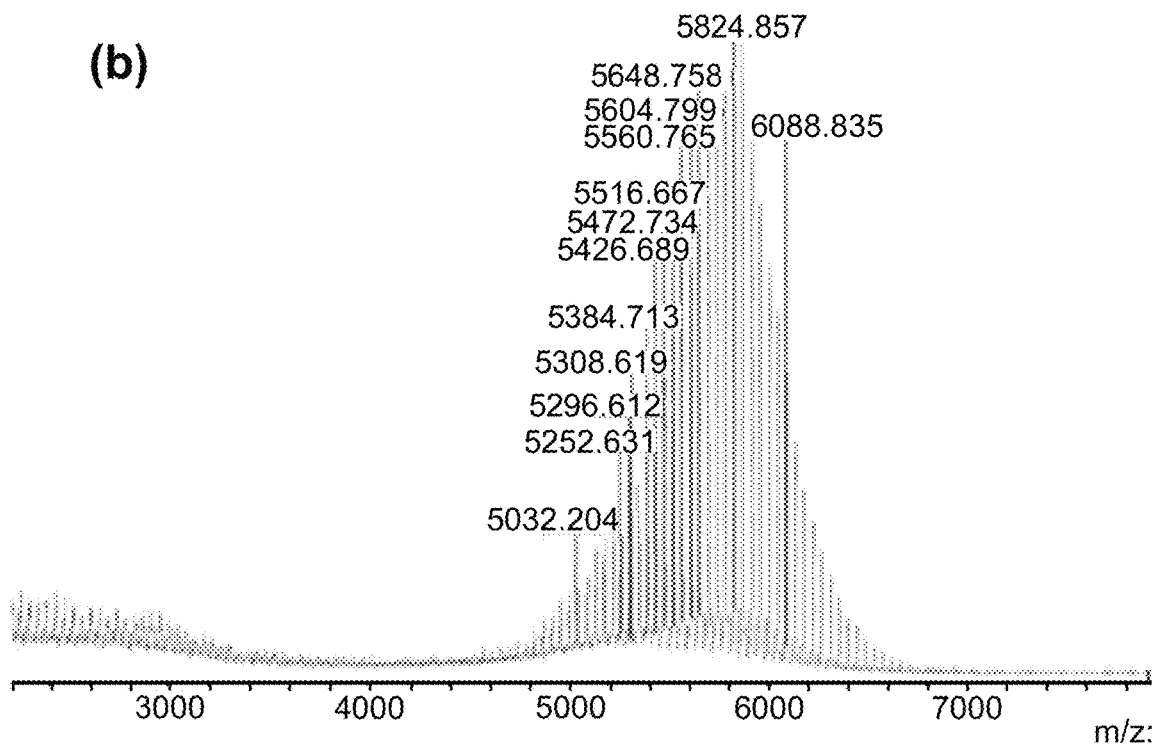
Figure 13:
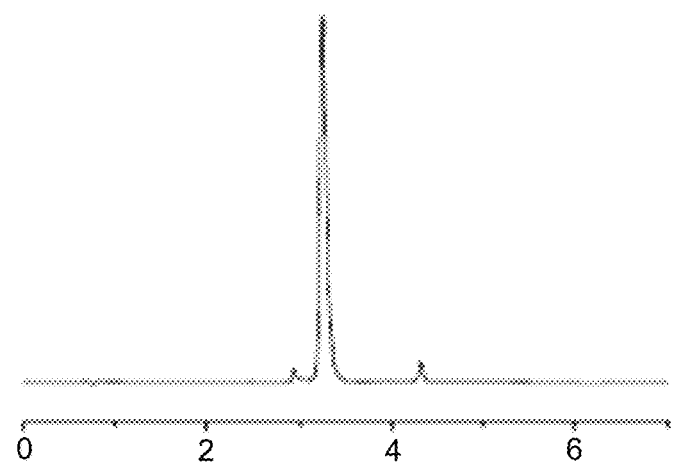
FIG. 13 consists of two panels showing: (panel a) HPLC trace of DM1-SS-PEG-DBCO, ($\lambda_{abs}$=285 nm); and (panel b) MALDI-TOF of DM1-SS-PEG-DBCO. Matrix: DCTB. Major peaks are [P+Na]$^+$.
Figure 13:
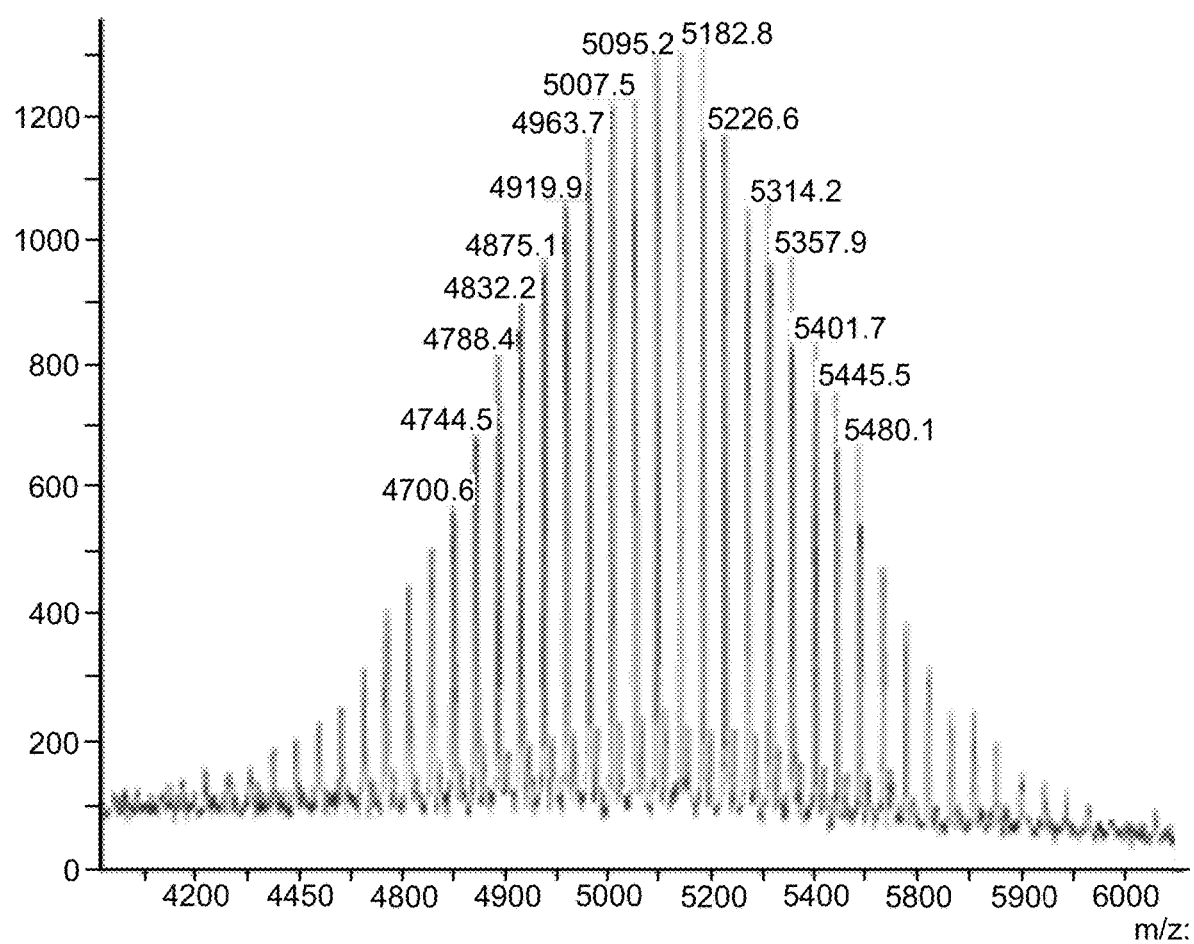

DBCO-DM1 conjugates (FIG. 11) were then synthesized through well-established chemistries. A polyethylene glycol 5000 was used in the design to serve the following purpose: 1. To improve the aqueous solubility of the conjugates; 2. To increase the hydrophilicity of the drug conjugate such that its passive uptake in non-azide labeled cells can be reduced; 3. To increase the blood circulation half-time (pharmacokinetics) of the molecule in vivo. A non-cleavable thioether linker same as T-DM1 was used in DM1-MAL-PEG-DBCO while a reduction cleavable disulfide bond was used in DM1-SS-PEG-DBCO to ensure the release of free DM1 upon internalization in cells. The purity and identity of the conjugates were verified by RP-HPLC (FIG. 12) and MALDI-TOF (FIG. 13). The solubility of the two conjugates were both shown to be more than 10 mg/mL PBS.

Figure 14:
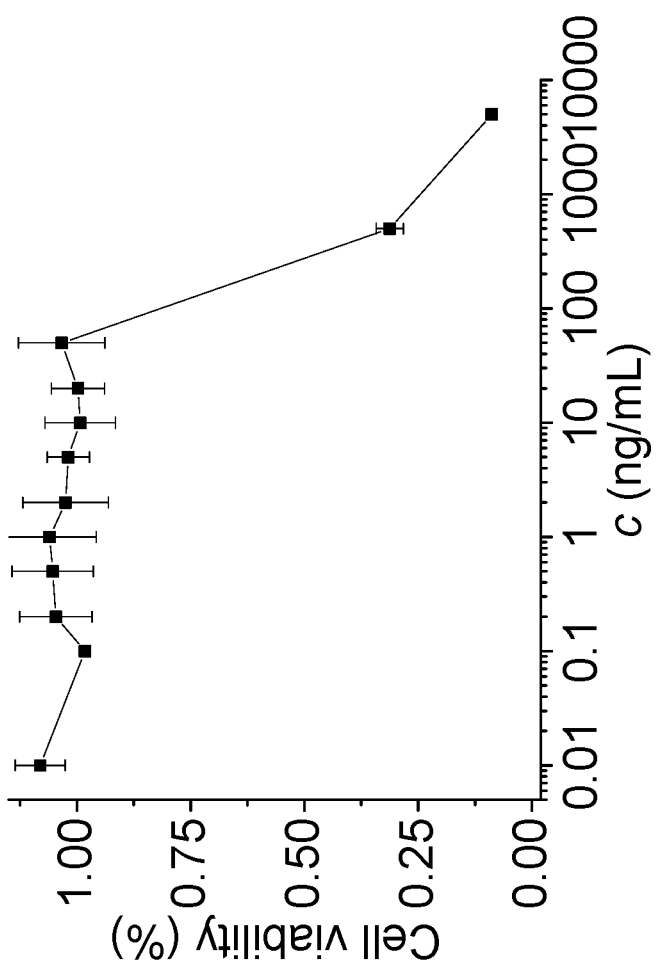
FIG. 14 is a chart showing cytotoxicity of DM-1-MAL-PEG$_{5k}$-DBCO in MDA-MB-231 breast cancer cells.

The cytotoxicity of DM1-MAL-PEG-DBCO was evaluated by MTT assay (FIG. 14). The IC50 of DM1-MAL-PEG-DBCO in MDA-MB-231 breast cancer cell was about 60 nM which is thousand times higher than parental DM1 (~0.03 nM) suggesting that the prodrug structure can significantly reduce the toxicity of DM1 while its cytotoxic killing is still effective.

Figure 15:
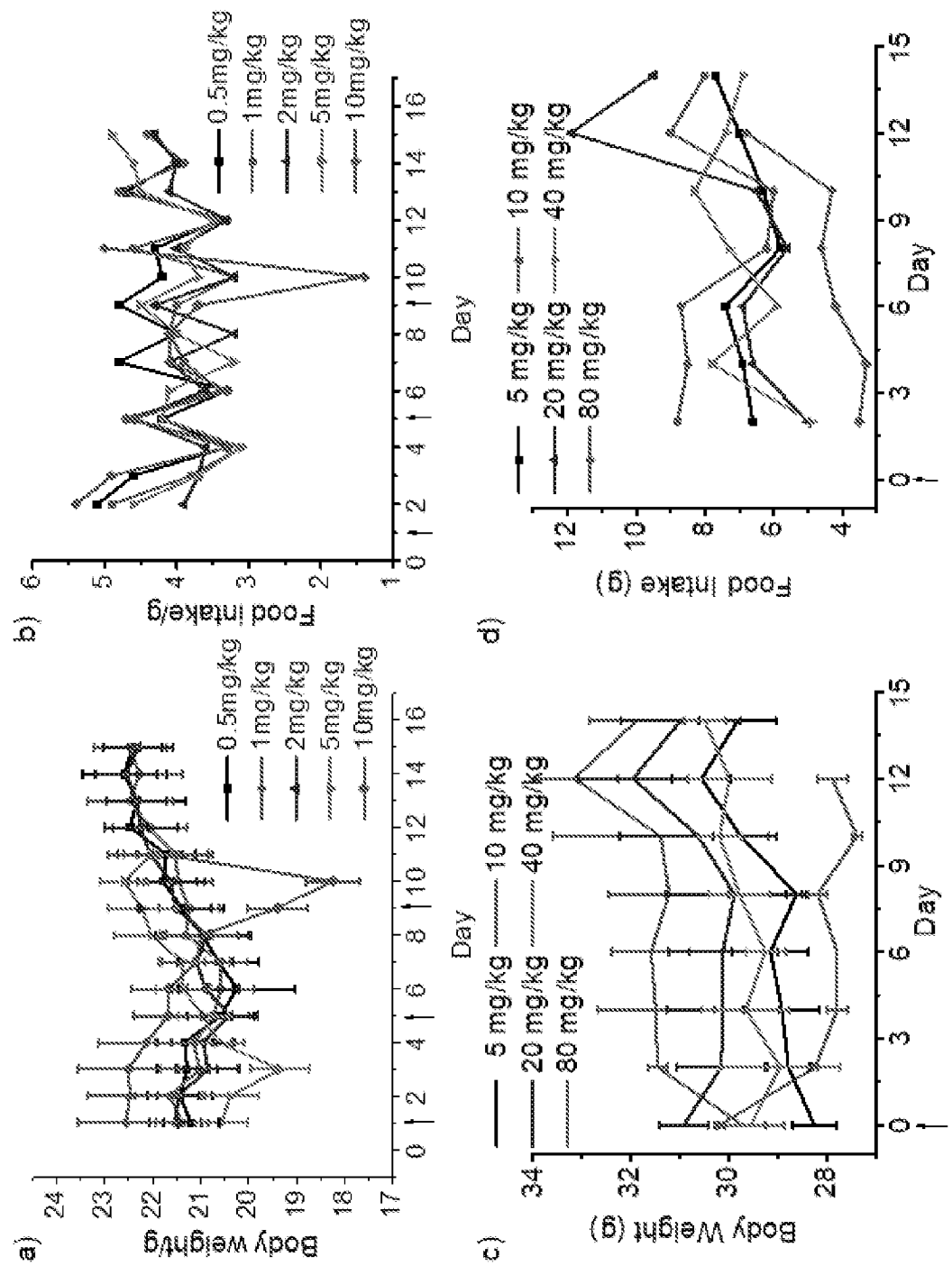
FIG. 15 consists of four panels showing body weight growth curves (panel a) and food intake curves (panel b) of nude female mice after i.v. injection of DM1-MAL-PEG-DBCO at various dosages; and body weight growth curves (panel c) and food intake curves (panel d) of CD-1 female mice after one i.v. injection of DM1-SS-PEG-DBCO at various dosages. Time of injections are marked with arrows.

The maximum tolerable dose (MTD) of the two conjugates were also evaluated in mice (FIG. 15). DM-1-MAL-$PEG_{5k}$-DBCO was dissolved in PBS and i.v. injected to female nude mice on day 1, 5, and 9 with different doses. No significant body weight loss was observed in CD-1 mice suggesting an MTD about 10 mg/kg. The DM1-SS-PEG-DBCO was injected using PBS with only one time administration in CD-1 mice. No body weight decrease was observed under the highest dose used in the study (80 mg/kg) suggesting an MTD higher than 80 mg/kg.

Example 13. DBCO-Platinum Conjugates

Figure 16:
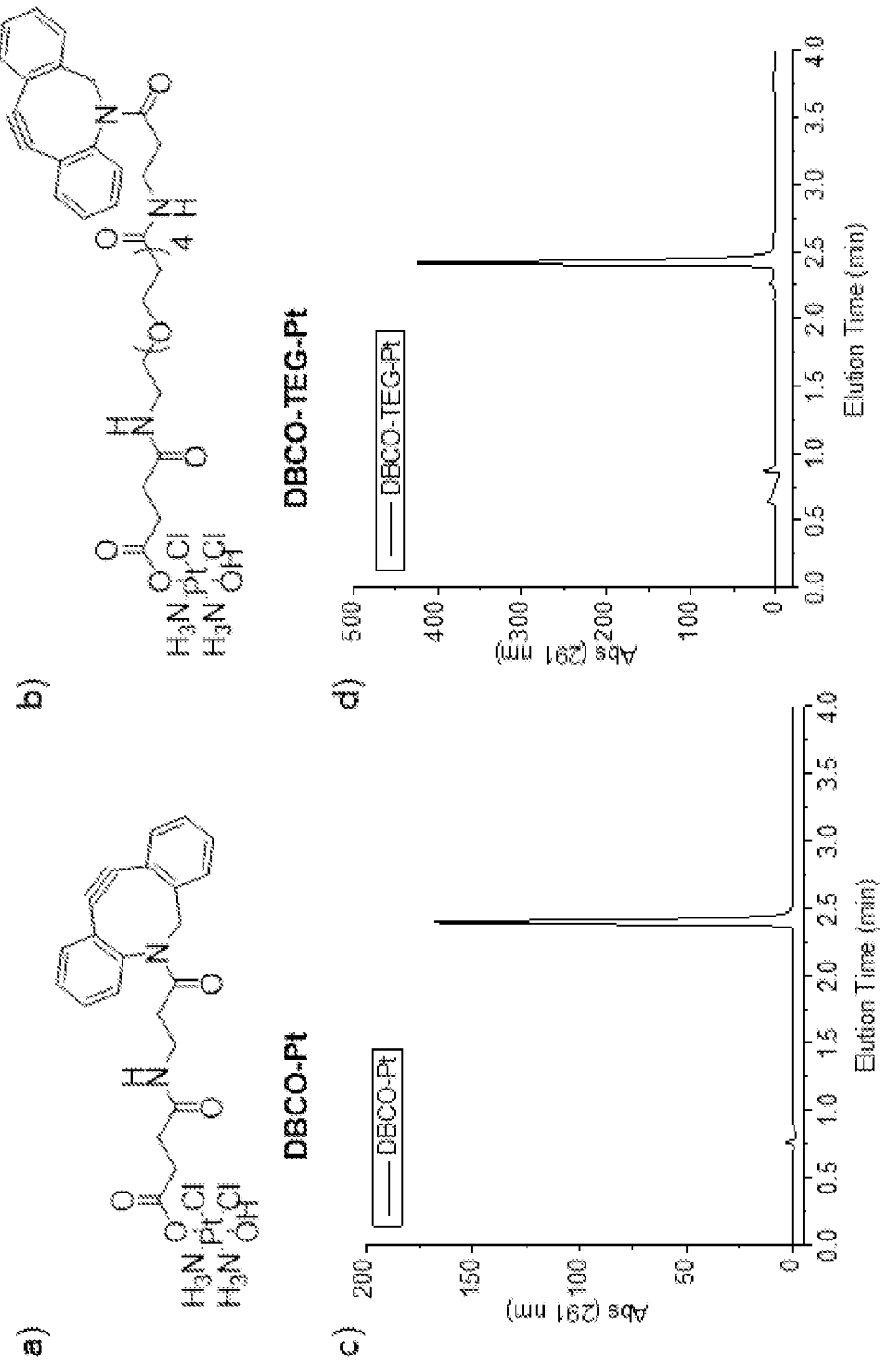
FIG. 16 consists of four panels showing chemical structures of DBCO-Pt (panel a) and DBCO-TEG-Pt (panel b). HPLC trace of DBCO-Pt (panel c) and DBCO-TEG-Pt (panel d); ($\lambda_{abs}$=291 nm).

Two DBCO-platinum conjugates were prepared, DBCO-Pt and DBCO-TEG-Pt. The Pt (IV) conjugates are known to be reduced to Pt (II)-cisplatin by intracellular reductase upon cell uptake.[14] A tetraethyleneglycol unit was incorporated in DBCO-TEG-Pt to improve the solubility of the conjugates (FIG. 16). The purity and identity of the conjugates were verified by reverse phase high performance liquid chromatography (RP-HPLC) (FIG. 16) and mass spectra.

Figure 17:
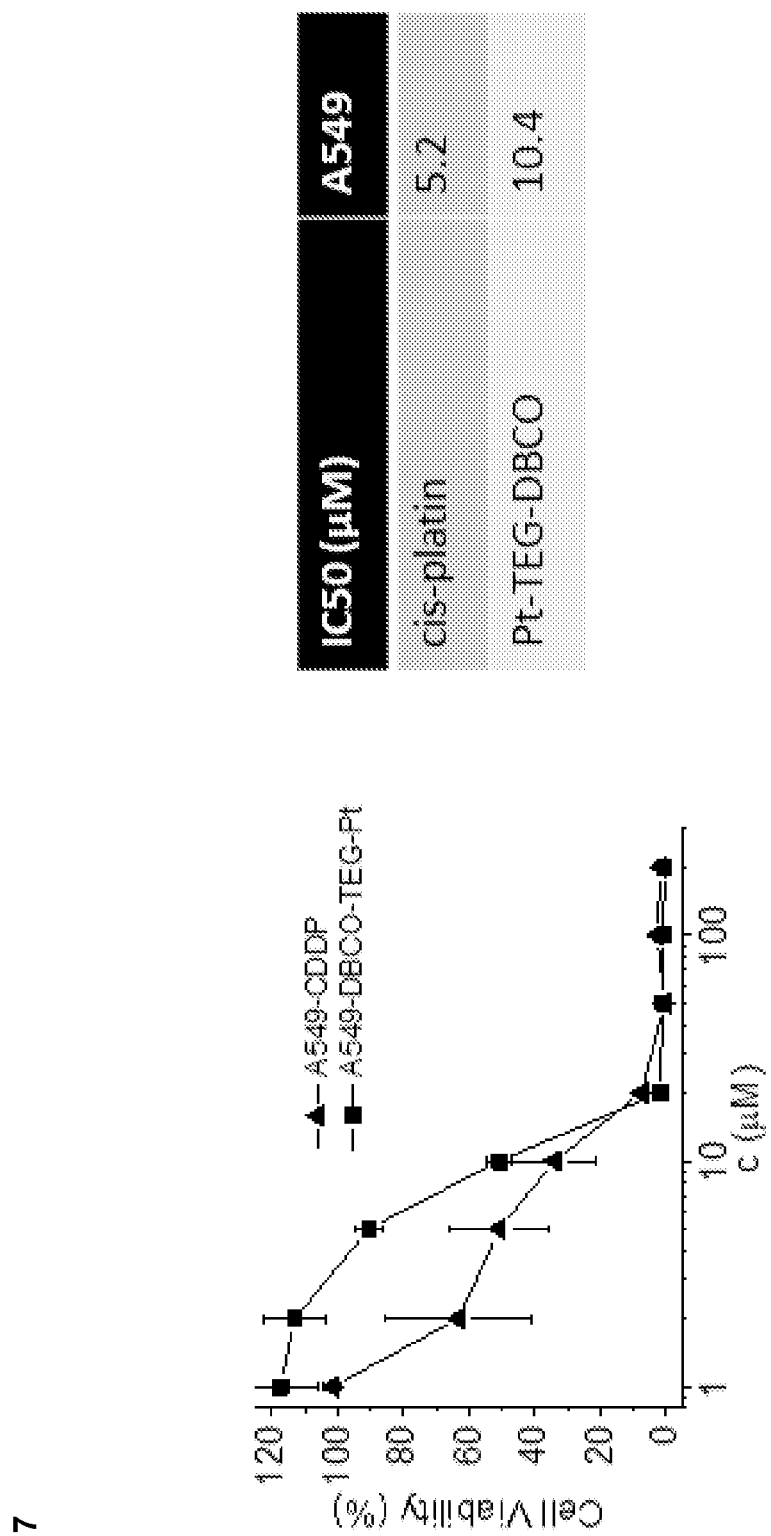
FIG. 17 shows a plot of the cytotoxicity and reports IC$_{50}$ values of DBCO-TEG-Pt in A549 non-small cell lung carcinoma. CDDP: cisplatin.
Figure 18:
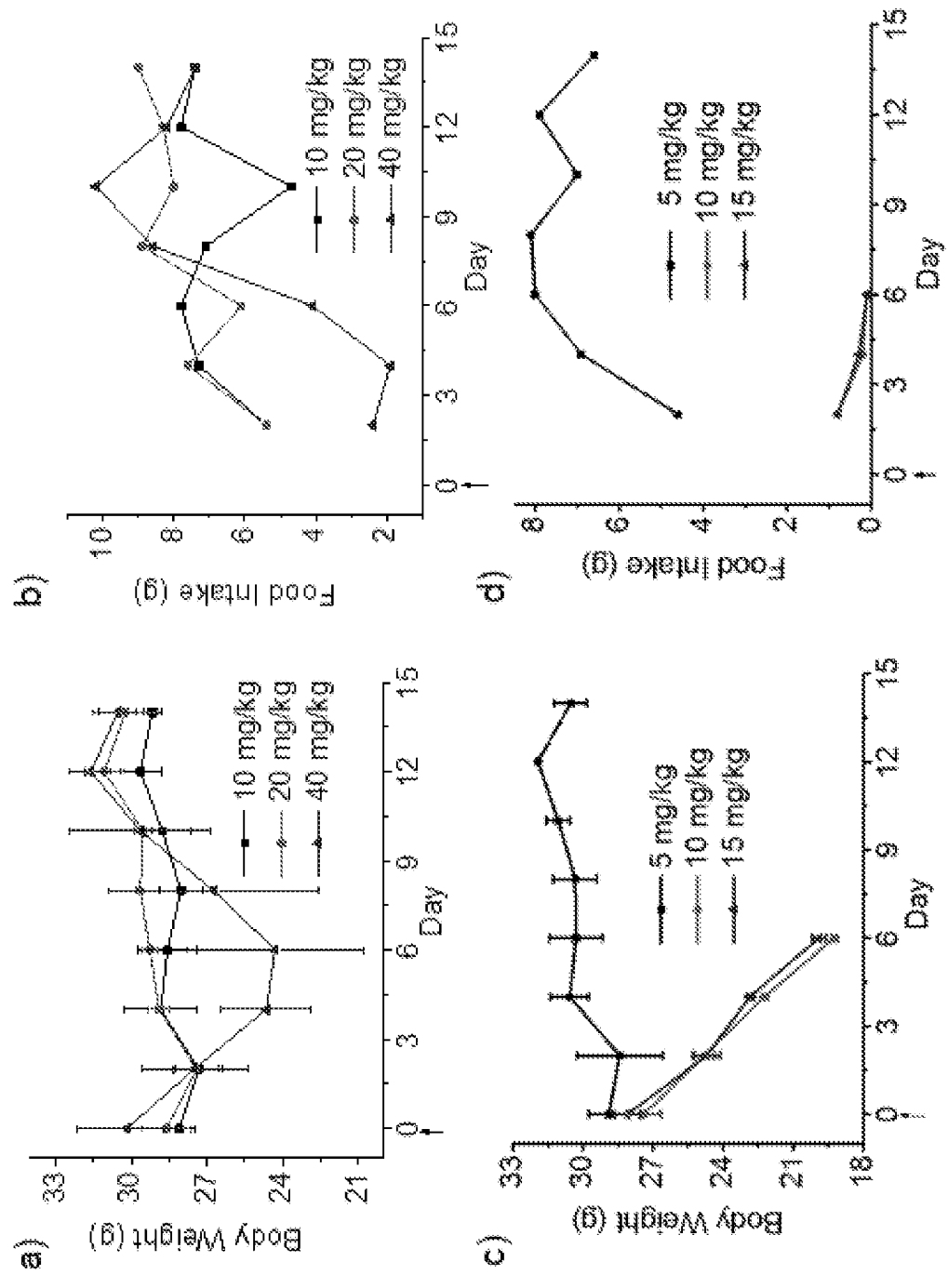
FIG. 18 consists of four panels showing body weight growth curves (panel a) and food intake curves (panel b) of CD-1 female mice after one i.v. injection of DBCO-TEG-Pt at various dosages; MTD: 40 mg/kg (equiv 12.8 mg/kg cisplatin); and body weight growth curves (panel c) and food intake curves (panel d) of CD-1 female mice after one i.v. injection of cis-platin at various dosages; MTD: 5 mg/kg.

The cytotoxicity of DBCO-TEG-Pt was evaluated by MTT assay in non-small cell lung carcinoma (A549) (FIG. 17). The IC50 of DBCO-TEG-Pt was 10 µM while the IC50 of the parental cisplatin was 5 M. The maximum tolerable dose (MTD) of DBCO-TEG-Pt was also evaluated in CD-1 mice (FIG. 18). DBCO-TEG-Pt was dissolved in DMSO-tween 80-PBS (5-10-85) formulation for i.v. injection and cisplatin was directly dissolved in PBS for the injection. MTD of cisplatin was about 5 mg/kg with a single injection on day 0 while the DBCO-TEG-Pt had an MTD of about 40 mg/kg (12.8 mg/kg equivalent cisplatin).

Example 14. DBCO-Paclitaxel Conjugates

Taxane drugs have been widely used in treatment of a variety of cancer patients and one of the most significant chemodrugs in clinical use. For breast cancer treatment, taxanes are recommended in preoperative/adjuvant combination, and monotherapy of recurrent/metastatic breast cancer.[15] Clinically used taxanes include paclitaxel, and docetaxel. Similar to many chemodrugs, taxane drugs showed excellent antitumor effect while the severe side effects prohibit their further use in both mono and combination regimen. Therefore, novel technology to improve the toxicology profile of taxanes while maintaining the therapeutic efficacy is highly desired with huge market potential. A successful example is Nab-paclitaxel (Abraxane®, nanoformulation of paclitaxel using albumin) that has a projected annual sale of 1 billion in 2017.

Figure 19:
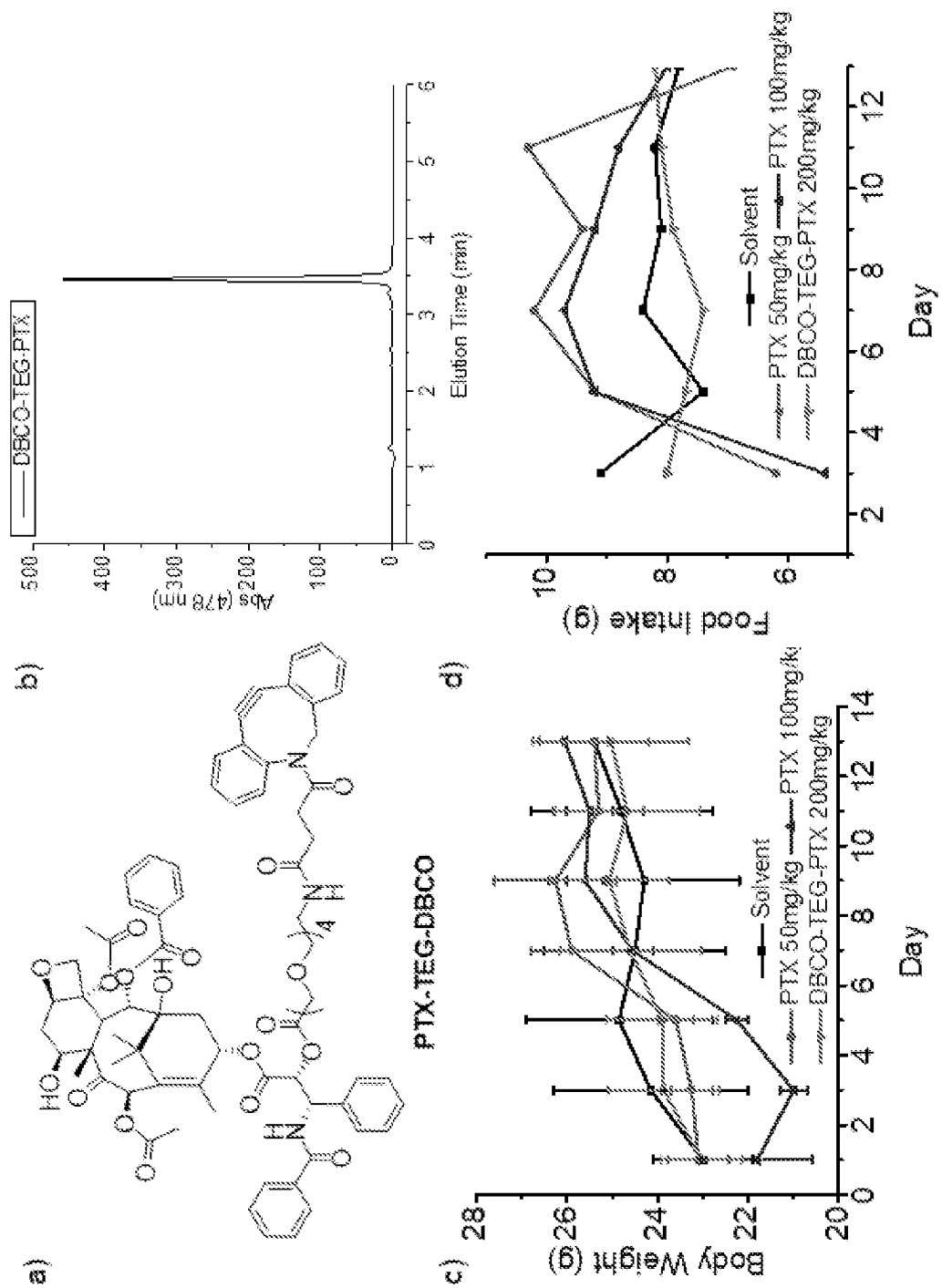
FIG. 19 consists of four panels showing: (panel a) chemical structure of PTX-TEG-DBCO; (panel b) HPLC trace of PTX-TEG-DBCO, ($\lambda_{abs}$=291 nm); body weight growth (panel c) and food intake (panel d) of CD-1 female mice after one i.v. injection of DBCO-TEG-PTX at various dosages.

A model DBCO-paclitaxel conjugate, PTX-TEG-DBCO was prepared through well-established reactions. (FIG. 19). The purity and identity of the conjugate was verified by RP-HPLC and ESI-MS (FIG. 19). PTX-TEG-DBCO can be dissolved in DMSO-tween 80-PBS (5-10-85) formulation for i.v. injection. The preliminary MTD study (FIG. 19) suggested that the MTD of PTX-TEG-DBCO is higher than 200 mg/kg (124 mg/kg equivalent PTX). Overall, the high MTD of the drug conjugates (higher than the maximal feasible dose in the formulation) suggested good biocompatibility of the prodrug.

REFERENCES CITED

1. Brandley, B. K. & Schnaar, R. L. Cell-surface carbohydrates in cell recognition and response. *Journal of Leukocyte Biology* 40, 97-111 (1986).
2. Stoolman, L. M. & Rosen, S. D. Possible role for cell-surface carbohydrate-binding molecules in lymphocyte recirculation. *The Journal of cell biology* 96, 722-729 (1983).
3. Dabelsteen, E. Cell surface carbohydrates as prognostic markers in human carcinomas. *The Journal of pathology* 179, 358-369 (1996).
4. Gorelik, E., Galili, U. & Raz, A. On the role of cell surface carbohydrates and their binding proteins (lectins) in tumor metastasis. *Cancer and Metastasis Reviews* 20, 245-277 (2001).
5. Fukuda, M. Possible roles of tumor-associated carbohydrate antigens. *Cancer research* 56, 2237-2244 (1996).
6. Prescher, J. A., Dube, D. H. & Bertozzi, C. R. Chemical remodelling of cell surfaces in living animals. *Nature* 430, 873-877 (2004).
7. Laughlin, S. T. & Bertozzi, C. R. Metabolic labeling of glycans with azido sugars and subsequent glycan-profiling and visualization via Staudinger ligation. *Nature protocols* 2, 2930-2944 (2007).
8. Saxon, E. et al. Investigating cellular metabolism of synthetic azidosugars with the Staudinger ligation. *Journal of the American Chemical Society* 124, 14893-14902 (2002).
9. Laughlin, S. T., Baskin, J. M., Amacher, S. L. & Bertozzi, C. R. In vivo imaging of membrane-associated glycans in developing zebrafish. *Science* 320, 664-667 (2008).
10. Chang, P. V. et al. Metabolic labeling of sialic acids in living animals with alkynyl sugars. *Angewandte Chemie International Edition* 48, 4030-4033 (2009).
11. Breidenbach, M. A. et al. Targeted metabolic labeling of yeast N-glycans with unnatural sugars. *Proceedings of the National Academy of Sciences* 107, 3988-3993 (2010).
12. Lambert, J. M.; Chari, R. V. "Ado-trastuzumab Emtansine (T-DM1): an antibody-drug conjugate (ADC) for HER2-positive breast cancer". *J. Med. Chem.* 2014, 57, 6949-6964.
13. Issell, B. F.; Crooke, S. T. "Maytansine". *Cancer Treat. Rev.* 1978, 5, 199-207.
14. Zheng, Y. R.; Suntharalingam, K.; Johnstone, T. C.; Yoo, H.; Lin, W.; Brooks, J. G.; Lippard, S. J. "Pt(IV) prodrugs designed to bind non-covalently to human serum albumin for drug delivery". *J Am Chem Soc* 2014, 136, 8790-8798.
15. "NCCN Clinical Practice Guidelines in Oncology (NCCN Guidelines)—Breast Cancer". 2017.
16. Wang, H.; Wang, R.; Cai, K.; He, H.; Liu, Y.; Yen, J.; Wang, Z.; Xu, M.; Sun, Y.; Zhou, X.; Yin, Q.; Tang, L.; Dobrucki, I. T.; Dobrucki, L. W.; Chaney, E. J.; Boppart, S. A.; Fan, T. M.; Lezmi, S.; Chen, X.; Yin, L.; Cheng, J. "Selective in vivo metabolic cell-labeling-mediated cancer targeting". *Nat. Chem. Biol.* 2017, 13, 415-424.
17. Dhar, S.; Daniel, W. L.; Giljohann, D. A.; Mirkin, C. A.; Lippard, S. J. "Polyvalent Oligonucleotide Gold Nanoparticle Conjugates as Delivery Vehicles for Platinum(IV) Warheads". *J. Am. Chem. Soc.* 2009, 131, 14652.

We claim:

1. A compound represented by formula (XI) or a pharmaceutically acceptable salt thereof:

K-Pol-L$^2$-D     (XI);

wherein:

K is

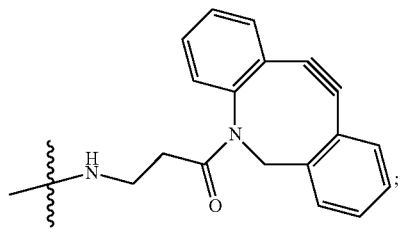 [SMILES: *NCCC(=O)N1Cc2ccccc2C#Cc2ccccc21]

Pol is a polyalkylene glycol;
L$^2$ is a trigger-responsive moiety comprising a disulfide bond; and
D is

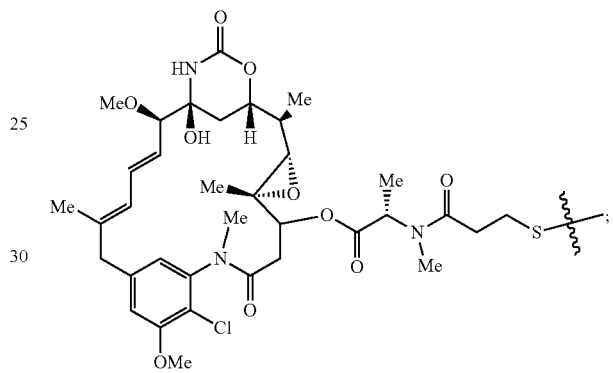

wherein the compound comprises a disulfide moiety.

2. The compound of claim 1 wherein Pol is:

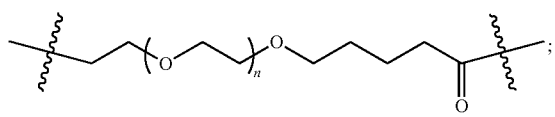

wherein n is 0-5000.

3. The compound of claim 1 wherein one end of the disulfide bond is a bond to the sulfur atom of the moiety:

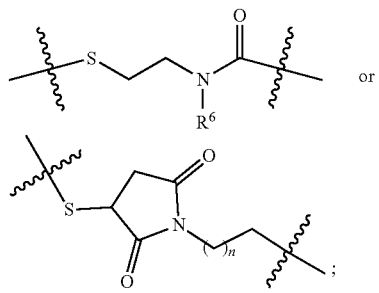

wherein
R$^6$ is H, tri((C$_1$-C$_6$)alkyl)silyl, or —C(O)((C$_1$-C$_6$)alkyl); or
n is 1 or 2.

4. The compound of claim 1 wherein one end of the disulfide bond is a bond via a sulfur atom to the moiety:

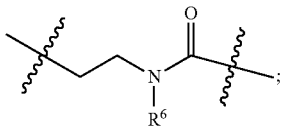

wherein $R^6$ is H, tri($(C_1$-$C_6)$alkyl)silyl, —C(O)($(C_1$-$C_6)$ alkyl), or —$(C_1$-$C_6)$alkyl.

5. The compound of claim 1 wherein one end of the disulfide bond is a bond via a sulfur atom to the moiety:

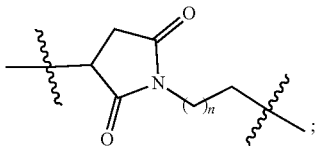

wherein n is 1 or 2.

6. The compound of claim 1 wherein the compound comprises:

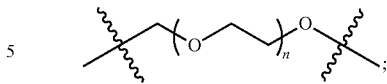

wherein n is 0-5000.

7. A pharmaceutical composition, comprising a compound of claim 1, and a pharmaceutically acceptable excipient or carrier.

8. The pharmaceutical composition of claim 7 wherein the compound is DM1-SS-PEG-DBCO and n is an integer from 1 to 5000.

9. A method of treating cancer, comprising administering to a subject in need thereof a therapeutically effective amount of a compound of claim 1, wherein the compound inhibits proliferation of breast cancer cells.

10. The method of claim 9 wherein the compound is DM1-SS-PEG-DBCO and n is an integer from 1 to 5000.

11. The compound DM1-MAL-PEG-DBCO:

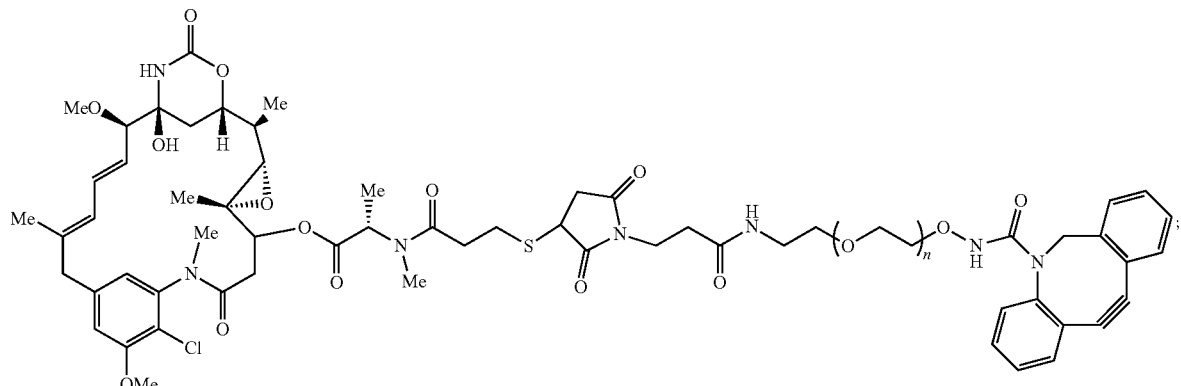

(DM1-MAL-PEG-DBCO)

wherein n is an integer from 1 to 5000.

12. The compound of claim 11 wherein n is an integer from 4 to 30.

13. A pharmaceutical composition comprising the compound of claim 11 and a pharmaceutically acceptable excipient or carrier.

14. A method of treating cancer, comprising administering to a subject in need thereof a therapeutically effective amount of a compound of claim 11, wherein the compound inhibits proliferation of breast cancer cells.

15. The compound DM1-SS-PEG-DBCO:

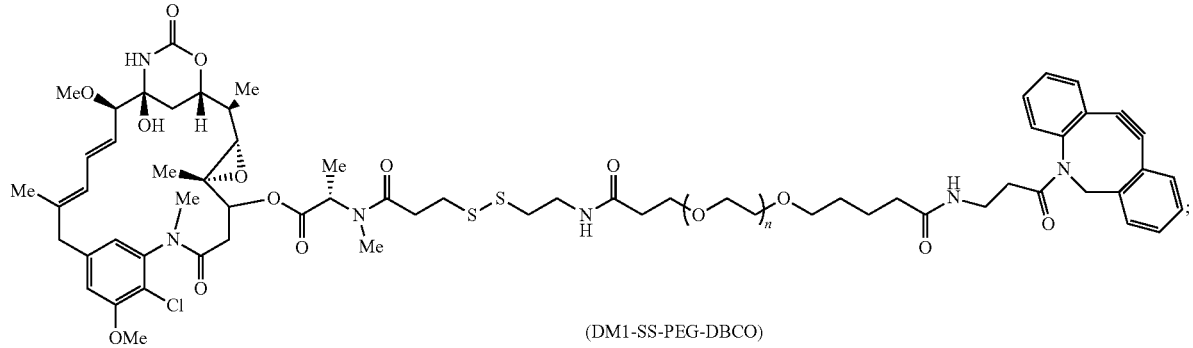

(DM1-SS-PEG-DBCO)

wherein n is an integer from 1 to 5000.

16. The compound of claim 15 wherein n is an integer from 4 to 30.

* * * * *